(12) United States Patent
Berger et al.

(10) Patent No.: US 12,122,806 B2
(45) Date of Patent: *Oct. 22, 2024

(54) ADENOVIRAL COAT PROTEIN DERIVED DELIVERY VEHICLES

(71) Applicants: THE EUROPEAN MOLECULAR BIOLOGY LABORATORY, Heidelberg (DE); CENTRE NATIONAL DE LA RECHERCHE SCIENTIFIQUE (CNRS), Paris (FR)

(72) Inventors: Imre Berger, Clifton Bristol (GB); Frédéric Garzoni, Rives (FR); Pascal Fender, Grenoble (FR)

(73) Assignees: THE EUROPEAN MOLECULAR BIOLOGY LABORATORY, Heidelberg (DE); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/590,444

(22) Filed: Feb. 1, 2022

(65) Prior Publication Data

US 2022/0162267 A1 May 26, 2022

Related U.S. Application Data

(62) Division of application No. 16/088,905, filed as application No. PCT/EP2017/057747 on Mar. 31, 2017, now Pat. No. 11,274,127.

(30) Foreign Application Priority Data

Mar. 31, 2016 (EP) ..................................... 16163372

(51) Int. Cl.
*C07K 14/005* (2006.01)
*A61K 39/12* (2006.01)
*C12N 7/00* (2006.01)

(52) U.S. Cl.
CPC ............ *C07K 14/005* (2013.01); *A61K 39/12* (2013.01); *C12N 7/00* (2013.01); *C12N 2710/10322* (2013.01); *C12N 2710/10323* (2013.01); *C12N 2710/10334* (2013.01)

(58) Field of Classification Search
CPC ........ C07K 14/005; A61K 39/12; C12N 7/00; C12N 2710/10322; C12N 2710/10323; C12N 2710/10334; C12N 2770/36122; C12N 2770/36134; A61P 35/00; A61P 37/02

See application file for complete search history.

(56) References Cited

U.S. PATENT DOCUMENTS 5,582,981 A  12/1996  Toole et al.
11,000,559 B2 *  5/2021  Champion ............ A61K 35/761

2014/0377294 A1 * 12/2014  Fueyo-Margareto .......................
                                                      A61K 39/001156
                                                      435/235.1
2018/0216081 A1 *  8/2018  Colloca .................. C12N 15/85
2020/0325179 A1  10/2020  Berger et al.

FOREIGN PATENT DOCUMENTS

| WO | 1997018317 | 5/1997 | |
| WO | 1997020575 | 6/1997 | |
| WO | 2001092549 A2 | 12/2001 | |
| WO | WO-2005075506 A1 * | 8/2005 | .......... C07K 14/005 |
| WO | 2007027860 A2 | 3/2007 | |
| WO | 2010117287 A2 | 10/2010 | |
| WO | 2010151159 A2 | 12/2010 | |
| WO | 2016118433 A1 | 7/2016 | |

OTHER PUBLICATIONS

Dehgan S, et al. Fiber protein [Human adenovirus 16]. GenBank: AET87329.1, Dep. Dec. 19, 2011. (Year: 2011).*

Li J, Lad S, Yang G, Luo Y, Iacobelli-Martinez M, Primus FJ, Reisfeld RA, Li E. Adenovirus fiber shaft contains a trimerization element that supports peptide fusion for targeted gene delivery. J Virol. Dec. 2006;80(24):12324-31. doi: 10.1128/JVI.01331-06. Epub Oct. 4, 2006. (Year: 2006).*

Wickham et al. Targeted adenovirus gene transfer to endothelial and smooth muscle cells by using bispecific antibodies. Journal of Virology, 1996, 70(10), 6831-6838.

Bal et al. Adenovirus type 7 penton. Eur J Biochem, 2000, 267, 6074-6081.

Fuschiotti et al. Structure of the Dodecahedral Penton Particle from Human Adenovirus Type 3. J Mol Biol, 2006, 356, 510-520.

(Continued)

*Primary Examiner* — Rachel B Gill
(74) *Attorney, Agent, or Firm* — Arrigo, Lee, Guttman & Mouta-Bellum LLP

(57) ABSTRACT

The present invention relates to new adenoviral coat protein based delivery vehicles. They are based on a modified penton base protomers that assemble into VLPs. Exposed areas of the penton base proteins can be modified to allow the VLP to specifically bind to any target and/or to comprise any desired peptide epitope. Additional cargo, for example drugs, proteins, or nucleic acids, can reversibly or irreversibly attached to the VLP via engineered fibre protein fragments. The present invention relates to such engineered penton base protomers, engineered proteins comprising an adenovirus fibre protein N-terminal fragment specifically binding to an adenovirus fibre protein binding cleft of a penton base protomer, VLPs comprising the engineered penton base protomers and optionally engineered proteins comprising an adenovirus fibre protein N-terminal fragment specifically binding to an adenovirus fibre protein binding cleft of a penton base protomer, nucleic encoding the engineered proteins, the VLPs as well as methods of producing the proteins and VLPs.

39 Claims, 14 Drawing Sheets

Figure 1:
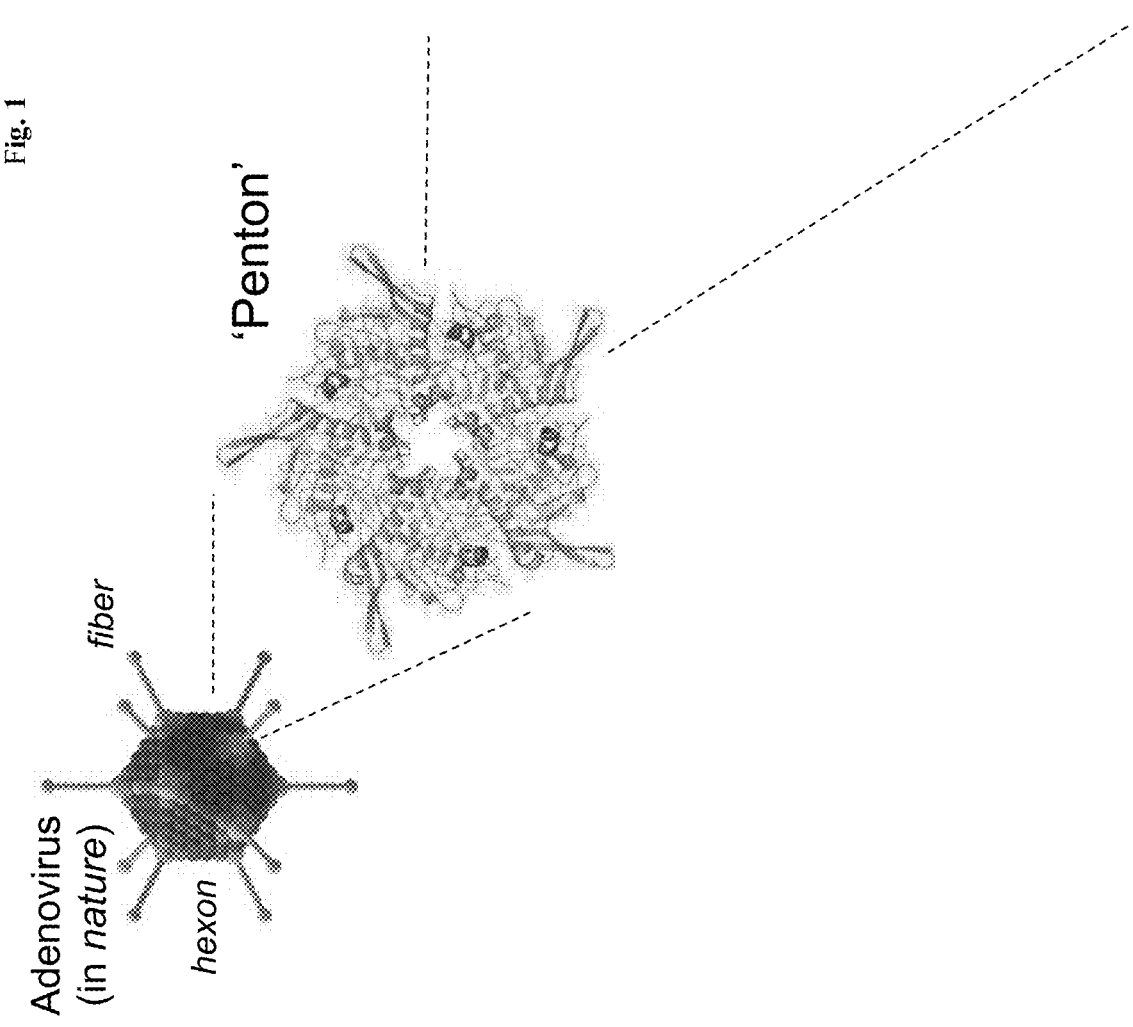

Specification includes a Sequence Listing.

(56) References Cited

OTHER PUBLICATIONS

Altschul et al., "Basic Local Alignment Search Tool," J. Mol. Biol., 215:403-410 (1990).
Altschul et al., "Gapped BLAST and PSI-BLAST: a new generation of protein database search programs," Nucleic Acids Research, 25(17):3389-3402 (1997).
Berger et al., "The MultiBac Protein Complex Production Platform at the EMBL," Journal of Visualized Experiments, 77 (e50159):1-8 (2013).
Brudno et al., "Glocal alignment: finding rearrangements during alignment," Bioinformatics, 19(1):i54-i62 (2003).
Partial European Search Report for EP 16 16 3372 dated Jun. 14, 2016 (5 pages).
Fender et al., "The impact of human adenovirus type 3 dodecahedron on host cells and its potential role in viral Infection," American Society for Microbiology, pp. 1-15 (2012).
Fitzgerald et al., "Protein complex expressing by using multigene baculoviral vectors," Nature Methods, 3(12):1021-1032 (2006).
Gubin et al., "Tumor neoantigens: building a framework for personalized cancer immunotherapy," The Journal of Clinical Investigation, 125(9):3413-3421 (2015).
International Search Report for PCT/EP2017/057747 dated Jun. 8, 2017 (7 pages).
Jayasena, Sumedha, "Aptamers: An Emerging Class of Molecules That Rival Antibodies in Diagnostics," Clinical Chemistry, 45(9):1628-1650 (1999).
Kam et al., "Early neutralizing IgG response to Chikungunya virus in infected patients targets a dominant linear epitope on the E2 glycoprotein," EMBO Molecular Medicine, 4:330-343 (2012).
Karlin et al., "Applications and statistics for multiple high-scoring segments in molecular sequences," Proc. Natl. Acad. Sci. USA, 90:5873-5877 (1993).
Klubman et al., "Mirror-image RNA that binds D-adenosine," Nature Biotechnology, 14:1112-1116 (1996).
Klug et al., "All you wanted to know about SELEX," Molecular Biology Reports, 20:97-107 (1994).
Nolte et al., "Mirror-design of L-oligonucleotide ligands binding to L-arginine," Nature Biotechnology, 14:1116-1119 (1996).
Shetty et al., "Engineering BioBrick vectors from BioBrick parts," Journal of Biological Engineering, 2(5):1-12 (2008).
Szolajska et al., "The Structural Basis for the Integrity of Adenovirus Ad3 Dodecahedron," PLOS one, 7(9):e46075 (2012).
Thompson, et al., "CLUSTAL W: improving the sensitivity of progressive multiple sequence alignment through sequence weighting, position-specific gap penalties and weight matrix choice," Nucleic Acids Research, 22(22):4673-4680 (1994).
Uhlmann et al., "Antisense Oligonucleotides: A New Therapeutic Principle," 90(4):1-42 (1990).
Wickham et al., "Targeting of adenovirus penton base to new receptors through replacement of its RGD motif with other receptor-specific peptide motifs," Gene Therapy, 2:750-756 (1995).
Strauss et al., "Hybridization with Radioactive Probes," Current Protocols in Molecular Biology, 6.3.1-6.3.6, pp. 1-6 (1993).
Zubieta et al., "The Structure of the Human Adenovirus 2 Penton," Molecular Cell, 17:121-135 (2005).
Vragniau C, Bufton JC, Garzoni F, Stermann E, Rabi F, et al. Synthetic self-assembling AD Domer platform for highly efficient vaccination by genetically encoded multiepitope display. Sci Adv. Sep. 25, 2019;5(9):eaaw2853. (Year: 2019).
Fender P, Ruigrok RW, Gout E, Buffet S, Chroboczek J. Adenovirus dodecahedron, a new vector for human gene transfer. Nat Biotechnol. Jan. 1997;15(1):52-6. (Year: 1997).
Rexroad J, Evans RK, Middaugh CR. Effect of pH and ionic strength on the physical stability of adenovirus type 5. J Pharm Sci. Feb. 2006;95(2):237-47. (Year: 2006).
Zochowska M, Paca A, Schoehn G, Andrieu JP, Chroboczek J, Dublet B, Szolajska E. Adenovirus dodecahedron, as a drug delivery vector. PLoS One. 2009;4(5):e5569. Epub May 15, 2009. (Year: 2009).

* cited by examiner

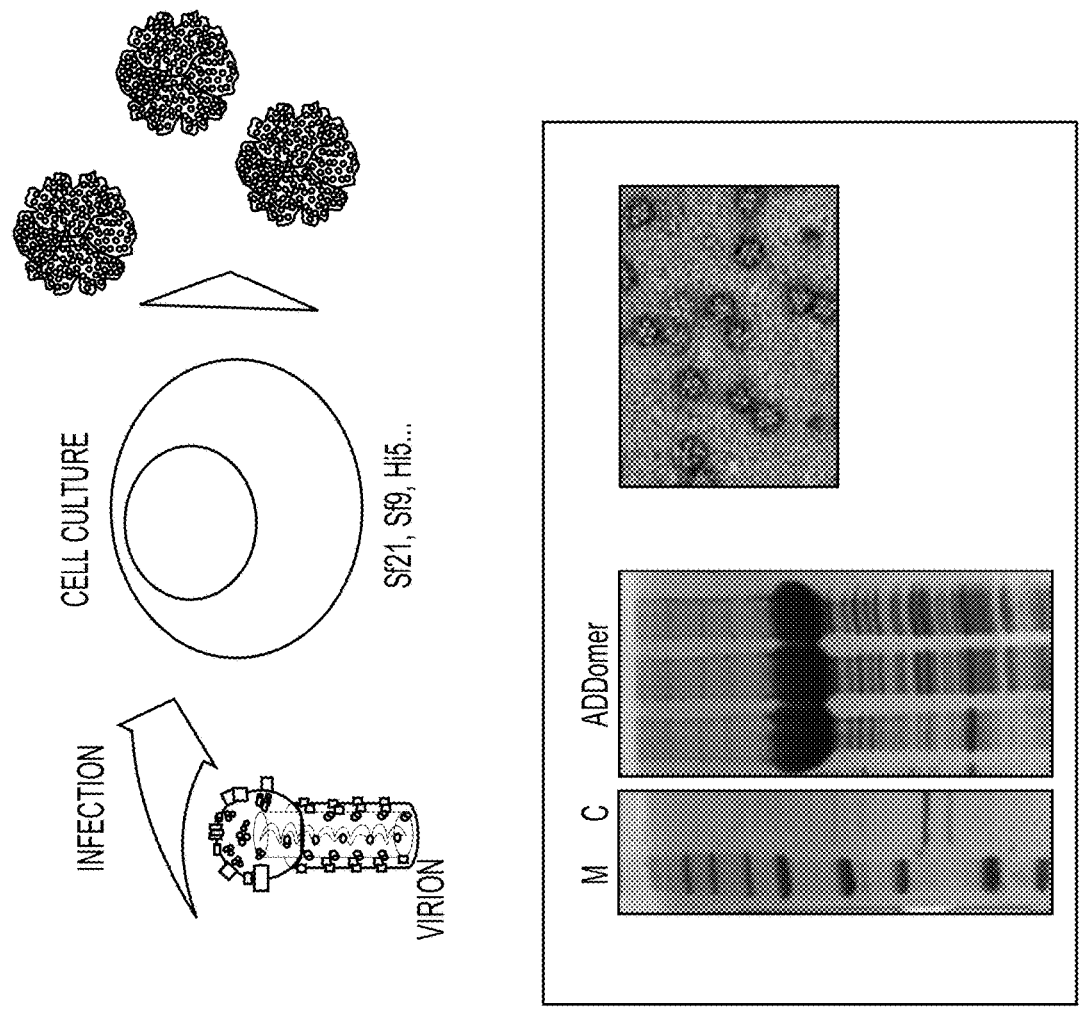
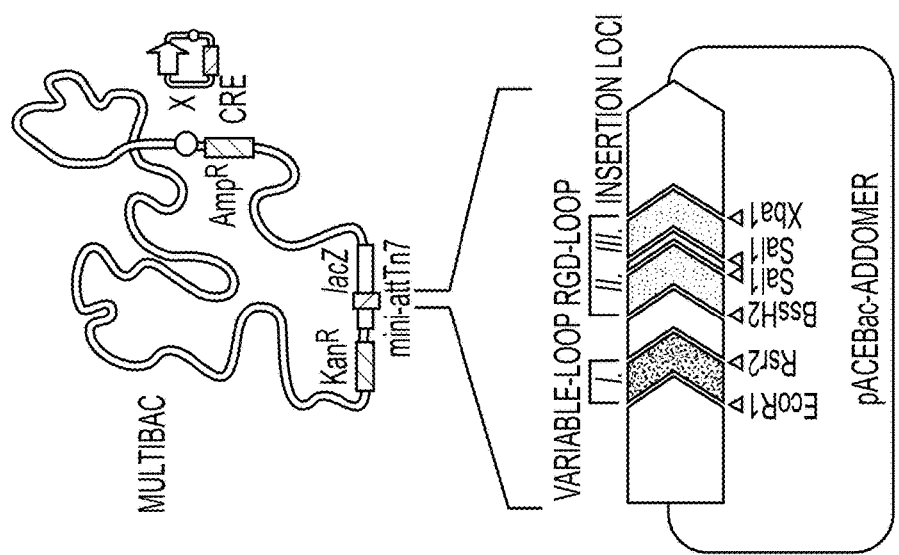
Fig. 4

ADENOVIRAL COAT PROTEIN DERIVED DELIVERY VEHICLES

CROSS-REFERENCE TO RELATED APPLICATIONS

This application is a divisional of U.S. application Ser. No. 16/088,905 filed Sep. 27, 2018, which is the U.S. Natl. Stage of International Appln. PCT/EP2017/057747 filed Mar. 31, 2017, which claims the benefit of EP Appln. 16163372.2 filed Mar. 31, 2016, all of which are incorporated herein by reference.

SEQUENCE LISTING

The instant application contains a Sequence Listing which has been submitted electronically in ASCII format and is hereby incorporated by reference in its entirety. Said ASCII copy, created on Aug. 25, 2023, is named E_0155_WOEPT1_SL.txt and is 176,643 bytes in size.

TECHNICAL FIELD OF THE INVENTION

The present invention relates to new adenoviral coat protein based delivery vehicles. They are based on a modified penton base protomers that assemble into VLPs. Exposed areas of the penton base proteins can be modified to allow the VLP to specifically bind to any target and/or to comprise any desired peptide epitope. Additional cargo, e.g. drugs, polypeptides, proteins, or nucleic acids, can be reversibly or irreversibly attached to the VLP via engineered fibre protein fragments. The present invention relates to such engineered penton base protomers, engineered proteins comprising a fibre protein fragment capable of binding to the penton base protomer, VLPs comprising the engineered penton base protomers and optionally engineered proteins comprising a fibre protein fragment, nucleic encoding the engineered proteins, the VLPs as well as methods of producing the proteins and VLPs.

BACKGROUND OF THE INVENTION

Infectious diseases continue to plague and decimate populations world-wide. Among the means at our disposal to counter this threat, vaccination has proven to be exceptionally powerful. Small-pox has been eradicated, measles, polio and tetanus constrained from the world by vaccination. Nonetheless, severe threats continue to challenge human health, notably also from emergent viruses that have adapted and emerged as new diseases or pathogenic strains with attributes facilitating pathogenicity.

Recent such examples are the severe threat posed by Chikungunya and Zika, insect-born viruses that is transmitted to humans by the bite of a mosquito. Both viruses are rapidly spreading to Asia and Europe, by means of its mosquito host, causing considerable alarm. Chikungunya and Zika disease can potentially incur severe costs for affected communities and economies, and a potent vaccination strategy to counter this emerging threat would be highly desirable. However, powerful vaccines are utterly lacking to date.

Ideally, a vaccine will be safe, non-replicative, efficient, and tunable. Moreover, it will be produced easily at industrial scale. Recombinant Virus Like Particles (VLPs) can be such ideal vaccines and therefore hold enormous promise. In this proposal, we will create such a VLP vaccine. We will make use of an amazingly versatile bio-similar multiprotein platform called ADDomer (Adenovirus dodecahedron derived multimer). ADDomer will serve to create vaccine candidates to combat infectious diseases caused by viruses (including but not limited to Chikungunya, Zika, others).

ADDomer is a synthetic scaffold derived from a virus-like particle (VLP) that in nature occurs during the human adenovirus serotype 3 (HAd3) replication cycle catalyzing internalization (Fender, P., et al. (2012) *J Virol* 86, 5380-5385. ADDomer is a designed bio-similar derived from this natural VLP, retaining the aptitude to autonomously self-assemble into a dodecahedron. ADDomer is uniquely suited to display multiple peptide and protein epitopes by means of fully flexible, solvent exposed loops. Engineering these loops does not destroy the global architecture of ADDomer particles. These loops offer convenient options to insert, by using methods from synthetic biology, multiple copies of highly immunogenic peptide epitopes, for example from viral pathogens. ADDomer is not limited to vaccine development against infectious diseases. A wide range of applications will potentially benefit from the ADDomer technology, including also cancer therapy. Moreover, ADDomer can not only display peptide epitopes. Proteins or protein domains can be likewise exposed by ADDomer, significantly broadening the scope of its application.

SUMMARY OF THE INVENTION

The present inventors have identified that certain regions in the penton base protomer are amenable to the introduction of heterologous peptide sequence without disrupting assembly of penton base protomers into penton subunits, which in turn can self-assemble into penton dodecamers forming virus like particles (VLPs) also referred to as ADDomers. The design is highly modular and enables rapid and flexible functionalization of extended loops for multipolypeptide display. The modularity is even further enhanced by using an adenovirus fibre protein fragment that specifically binds to the penton base protomer. The VLPs of the present invention are safe since they do not comprise genetic material. The penton base protomers can receive and display up to 180 foreign polypeptide motifs including antigens, neutralizing polypeptides, oncoepitope polypeptides, single chain antibodies, and nanobodies.

Accordingly, in a first aspect the present invention relates to an engineered polypeptide comprising an adenovirus penton base protomer, wherein said penton base protomer comprises a first RGD-loop, a second RGD-loop, a variable loop (V loop), adenovirus fibre protein binding cleft and/or a N-terminal domain and comprises one or more of the following:

(i) at least one target specific binding domain in the first, the second or both the first and the second RGD-loops, and/or in the V loop; and/or (ii) one or more non-adenoviral polypeptides, in the first, the second or both the first and the second RGD-loops and/or in the V loop; and/or (iii) a non-adenoviral polypeptide at the N- and/or C-terminus of the penton base protomer; and/or (iv) at least one heterologous coupling residue in the first, the second, or both the first and the second RGD-loops, in the V loop and/or in the N-terminal domain of the penton base protomer, wherein the N-terminus of the N-terminal domain within the penton base protomer is defined as follows:

$$X_1\text{-G-R-N-S-I-R} \quad \text{(SEQ ID NO: 44)}$$

and the C-terminus of the N-terminal domain within the penton base protomer is defined as follows:

$$D\text{-}X_2\text{-R-S-R-G,} \quad \text{(SEQ ID NO: 45)}$$

wherein
$X_1$ is selected from the group consisting of G and E, and $X_2$ is selected from the group consisting of D and E; and/or
  (v) a drug or polypeptide covalently or non-covalently coupled to one or more amino acids of the first, the second or both the first and the second RGD-loops and/or one or more amino acids of the V loop of the penton base protomer; and/or
  (vi) at least one heterologous coupling residue in the adenovirus fibre protein binding cleft of the penton base protomer and wherein the engineered polypeptide of the first aspect is preferably capable of assembling into VLPs.

In a second aspect the present invention relates to an engineered polypeptide comprising at least one adenovirus fibre protein N-terminal fragment specifically binding to an adenovirus fibre protein binding cleft of a penton base protomer and:
  (i) a non-adenoviral polypeptide; and/or
  (ii) is covalently or non-covalently coupled to a drug or label.

In a third aspect the present invention relates to a nucleic acid encoding the engineered polypeptide comprising an adenovirus penton base protomer of the invention and/or the engineered polypeptide of the invention comprising an adenovirus penton base protomer binding fibre protein fragment.

In a fourth aspect the present invention relates to an expression vector comprising the nucleic acid of the invention.

In a fifth aspect the present invention relates to a cloning vector encoding:
  (i) a polypeptide comprising an adenovirus penton base protomer, wherein said penton base protomer comprises a first RGD-loop, a second RGD-loop, a variable loop and/or a binding site for adenovirus fibre protein adapted for introducing nucleic acids encoding non-adenoviral polypeptides into the nucleic acids encoding the first RGD-loop, the second RGD-loop and/or the variable loop; or
  (ii) polypeptide comprising an adenovirus penton base protomer binding fibre protein fragment adapted for introducing nucleic acids encoding non-adenoviral polypeptides a the C- and/or N-terminus.

In a sixth aspect the present invention relates to a recombinant host cell comprising the expression vector of the invention or the cloning vector of the invention.

In a seventh aspect the present invention relates to a pentamer comprising five engineered polypeptides comprising adenovirus penton base protomer of the invention.

In an eight aspect the present invention relates to a virus-like particle (VLP) comprising 12 pentamers of the invention.

In a ninth aspect the present invention relates to a VLP comprising 12 pentamers each comprising five adenovirus penton base protomers and at least one engineered polypeptide of the invention comprising an adenovirus penton base protomer binding fibre protein fragment.

In a tenth aspect the present invention relates to a method for producing the engineered polypeptide comprising an adenovirus penton base protomer of the invention and/or the engineered polypeptide of the invention comprising an adenovirus penton base protomer binding fibre protein fragment, comprising the steps of:
  (a) providing a recombinant host cell of the invention;
  (b) expressing the engineered polypeptide; and
  (c) purifying the engineered polypeptide.

In an eleventh aspect the method for producing a VLP of the invention comprising the steps of the method of the tenth aspect of the invention and the further step of allowing the engineered polypeptides to assemble into a VLP.

In a twelfth aspect the present invention relates to a method for producing a VLP of the invention comprising disease and/or patient specific non-adenoviral polypeptides, comprising the steps of:
  (a) providing a cloning vector of the invention;
  (b) determining the amino acid sequence of disease or patient specific non-adenoviral polypeptides;
  (c) inserting nucleic acids encoding at least one of said non-adenoviral polypeptides into nucleic acids encoding the first RGD-loop, the second RGD-loop and/or the variable loop of the adenovirus penton base protomer, and/or at nucleic acid position preceding or subsequent to nucleic acids encoding the N- or C-terminus of the engineered polypeptide comprising an adenovirus penton base protomer binding fibre protein fragment;
  (d) expressing the engineered adenovirus penton base protomer in a host cell, optionally together with the engineered polypeptide comprising an adenovirus penton base protomer binding fibre protein fragment; and
  (e) purifying said VLP optionally comprising an adenovirus penton base protomer binding fibre protein fragment, or said engineered polypeptide comprising an adenovirus penton base protomer binding fibre protein fragment.

In a thirteenth aspect the present invention relates to a method for producing a VLP of the invention comprising disease and/or patient specific non-adenoviral polypeptides, comprising the steps of:
  (a) providing a cloning vector of the invention;
  (b) determining the amino acid sequence of disease or patient specific non-adenoviral polypeptides;
  (c) inserting nucleic acids encoding at least one of said non-adenoviral polypeptides at nucleic acid position preceding or subsequent to nucleic acids encoding the N- or C-terminus of the engineered polypeptide comprising an adenovirus penton base protomer binding fibre protein fragment;
  (d) expressing the engineered polypeptide comprising an adenovirus penton base protomer binding fibre protein fragment in a host cell, optionally together with an adenovirus penton base protomer; and
  (e1) purifying said engineered polypeptide comprising an adenovirus penton base protomer binding fibre protein fragment and admixing with adenovirus penton base protomers or engineered adenovirus penton base protomers of the invention; or
  (e2) purifying said VLP in case that the adenovirus penton base protomer was co-expressed.

In a fourteenth aspect the present invention relates to a method for producing a VLP of the invention comprising disease and/or patient specific non-adenoviral polypeptides, comprising the steps of:
(a) determining the amino acid sequence of disease or patient specific non-adenoviral polypeptides;
(b) synthetizing an engineered polypeptide of the invention comprising an adenovirus penton base protomer binding fibre protein fragment and at least one of said non-adenoviral polypeptides; and
(c) admixing said engineered polypeptide with adenovirus penton base protomers or engineered adenovirus penton base protomers of the invention with pentamers of the invention or with VLPs of the invention.

In a fifteenth aspect the present invention relates to a VLP producible by a method of producing a VLP of the invention.

In a sixteenth aspect the present invention relates to a pharmaceutical composition comprising the engineered polypeptide comprising an adenovirus penton base protomer of the invention and/or the engineered polypeptide of the invention comprising an adenovirus penton base protomer binding fibre protein fragment, the nucleic acid encoding one or more of the engineered proteins of the invention, the expression vector of the invention or the VLP of the invention, and a pharmaceutically acceptable carrier and/or suitable excipient(s).

In a seventeenth aspect the present invention relates to an engineered polypeptide comprising an adenovirus penton base protomer of the invention and/or the engineered polypeptide of the invention comprising an adenovirus penton base protomer binding fibre protein fragment, the nucleic acid encoding one or more of the engineered proteins of the invention, the expression vector of the invention or the VLP of the invention for treating and/or preventing an infectious disease, an immune disease or cancer.

FIGURES

FIG. 1: Shows the synthetic self-assembling multimeric scaffolds of the invention also referred to as VLPs. 5 protomers form one penton subunit and 12 pentons spontaneously self-assemble into large superstructure which is alternatively termed a VLP or ADDomer.

Figure 2:
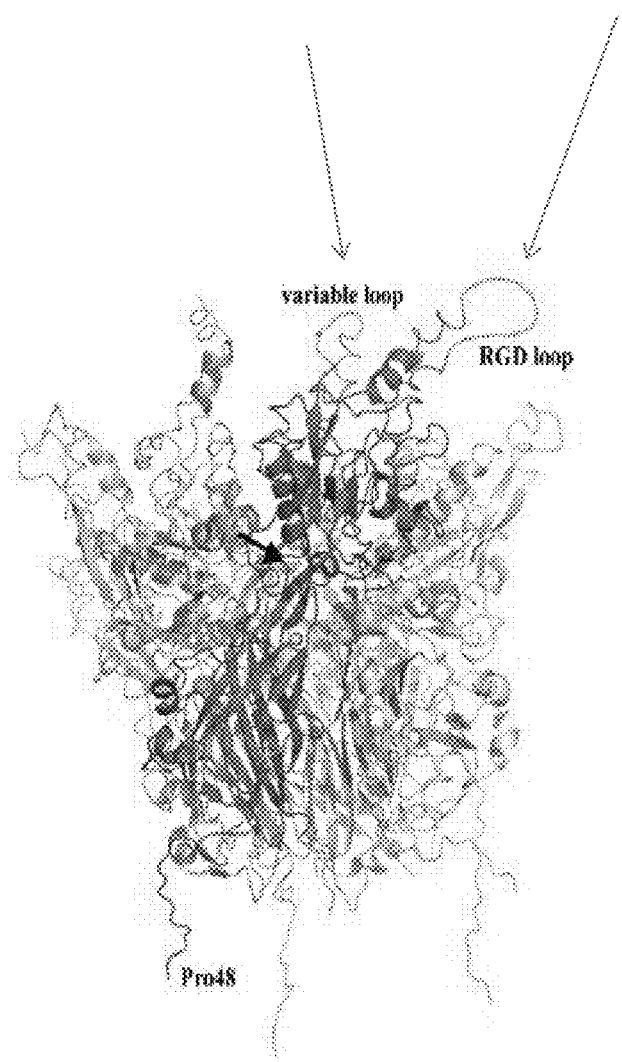

FIG. 2: Shows a side view of penton. The penton protomer contains two highly heteromoiphic RGD-loops and one Variable loop (V loop) of unconserved, widely varied length and sequence. In this respect the present inventors determined them to be similar to antibody CDRs and suitable for introducing binding sites that allow the resulting VLP to bind to any desired target. It is suitable for display of multiple epitopes and can display up to 180 epitopes per VLP.

Figure 3:
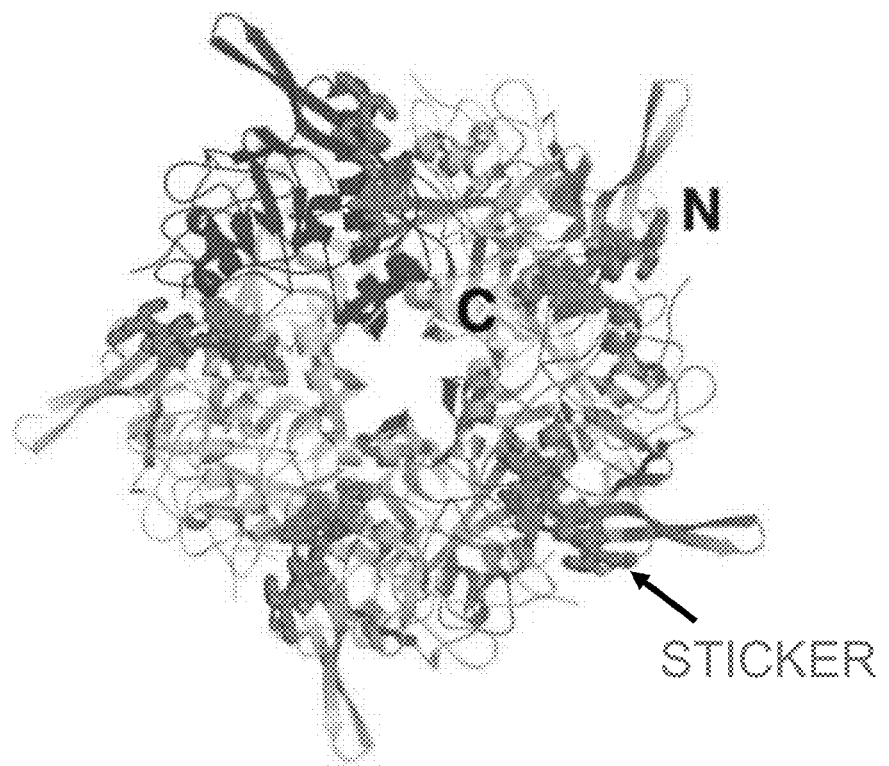

FIG. 3: The penton base protomer comprises a region—a sticky patch—that interacts with adenovirus fibre protein. This sticky patch can bind with subnanomolar affinity to fragments of adenoviral fibre—also referred to as "STICKER". It is preferred that these fibre fragments are multimerized to increase binding affinity. The STICKER$_n$-tag (n is preferably 2 to 4) can be fused to the C- and/or N-terminus of a protein to be attached to the VLP or can be covalently or non-covalently coupled to any other cargo. The STICKER$_n$-tag, thus provides the ability to display on the surface of the VLP peptides, proteins, nucleic acids, liposomes and any other cargo to be delivered by the VLP. An ADDomer has 12 sites for binding to a STICKER-tagged cargo. In one embodiment the sticky patch on the penton base protomer is modified to comprise a coupling residue, preferably a Cys and the STICKER$_n$-tag is also modified to comprise a Cys in a way that under non-reducing conditions the Cys in the sticky patch and the STICKER$_n$-tag can form a covalent bond, which will be severed under reducing conditions.

FIG. 4: Shows diagrammatically the process of producing the ADDomers. The ADDomers are produced with high yield, are simple to purify and are exceptionally stable. The pACEBac-ADDOMER vector has three regions encoding the first and second RGD loop as well as the V loop that can easily be replaced with any desired peptide chain, e.g. a peptide conferring specific binding activities and/or an antigenic epitope.

Figure 5:
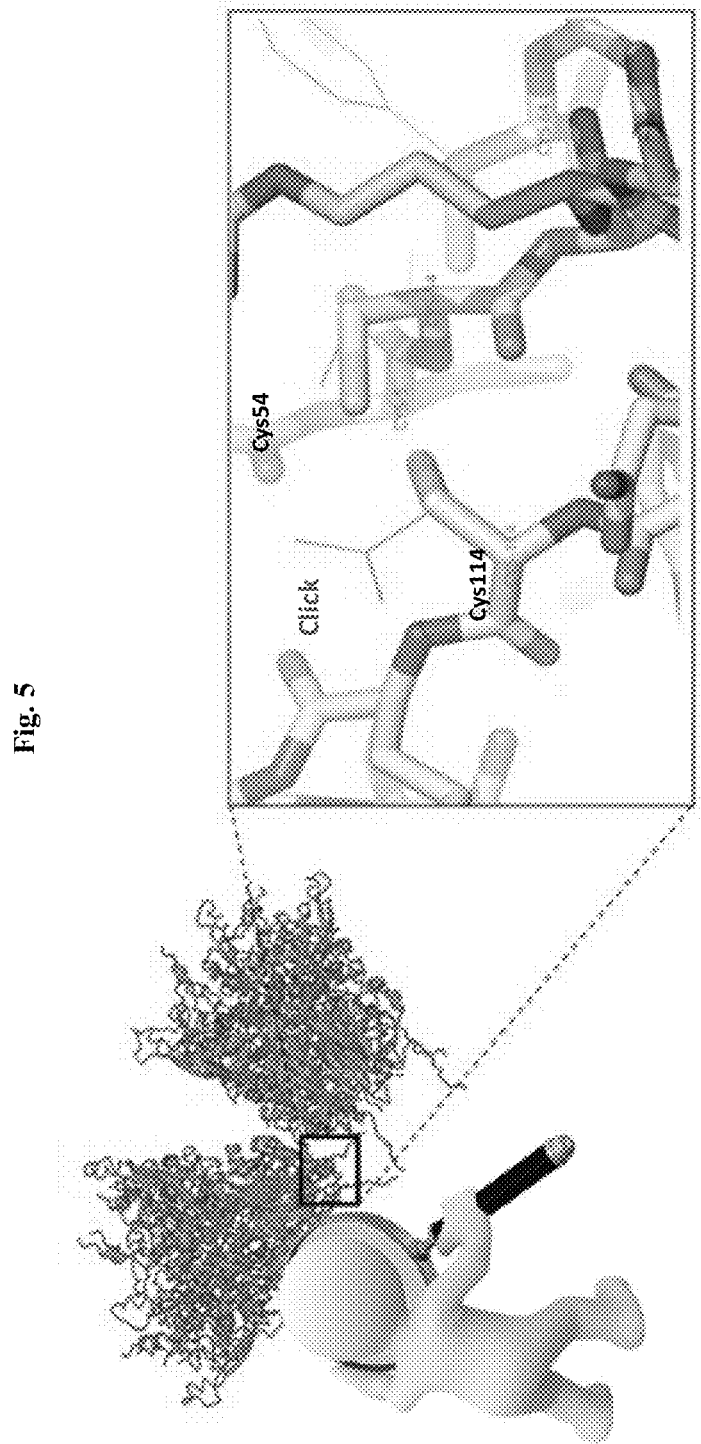

FIG. 5: The penton base protomer comprises a region that interacts with the neighboring protomer when assembling into dodecahedron, known as "strand swapping". Mutation of relevant amino acids residues to cysteines can give rise to stabilization of the VLP super-structure by covalent disulfide bond formation, making the ADDomer thermostable. A schematic representing strand swapping residues mutated to cysteine is shown.

Figure 6:
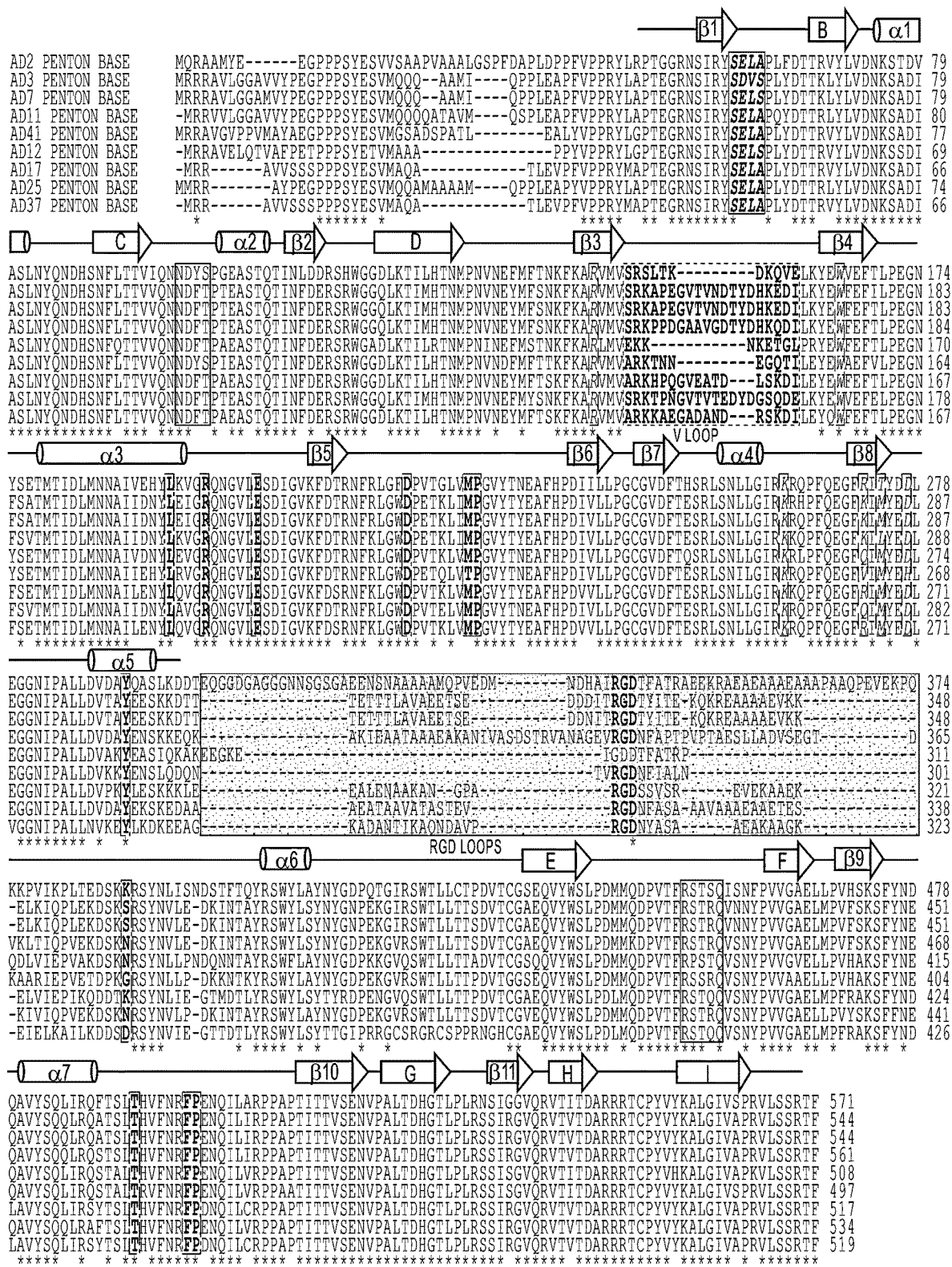

FIG. 6: The sequences indicated are highly conserved throughout the species. The alignment shows wild-type penton base sequences from different natural serotypes. Sequences shown are: Subgroup C Ad2, accession number P03276 (SEQ ID NO:79); subgroup B Ad3, S41389 (SEQ ID NO:80); subgroup B Ad7, AAR89958 (SEQ ID NO:81); subgroup B Ad11, AAP49205 (SEQ ID NO:82); subgroup F Ad41, AAF14179 (SEQ ID NO:83); subgroup A Ad12, P36716 (SEQ ID NO:84); subgroup D Ad17, NP_049379 (SEQ ID NO:85); subgroup E Ad25, NP 478405 (SEQ ID NO:86); and subgroup D Ad37, CAC82544 (SEQ ID NO:87) were aligned. The V loop is shown in the indicated box; the RGD-loops are shown in the indicated box. Those amino acid residues of the penton base protomer that bind to fibre are highlighted. They are all conserved amongst the serotypes.

Figure 7:
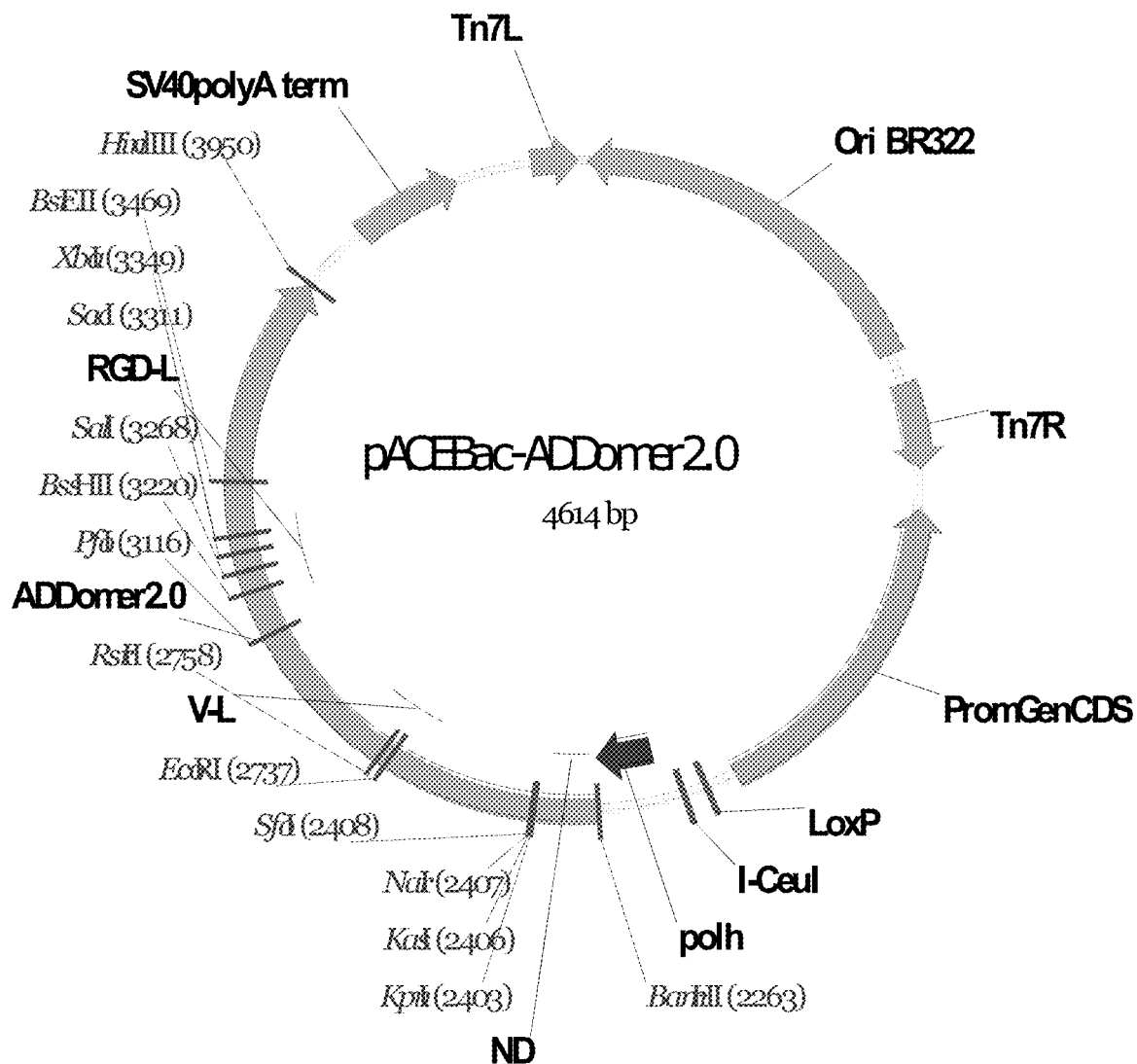
Figure 8:
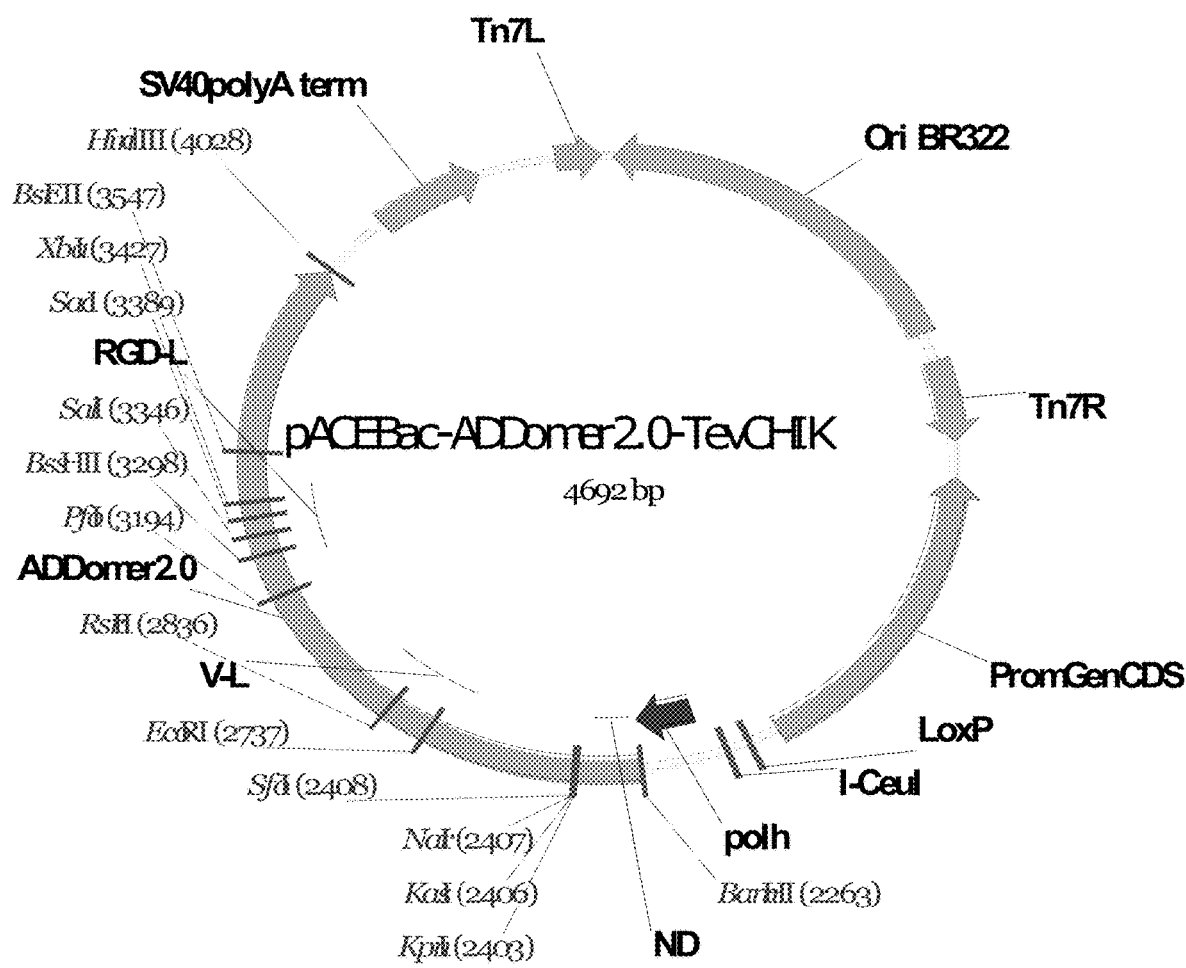

FIGS. 7 and 8: The structure of two preferred cloning vectors of the present invention is shown. The nucleic acid sequences of the cloning vectors are respectively provided in SEQ ID NO: 61 and 62.

Figure 9:
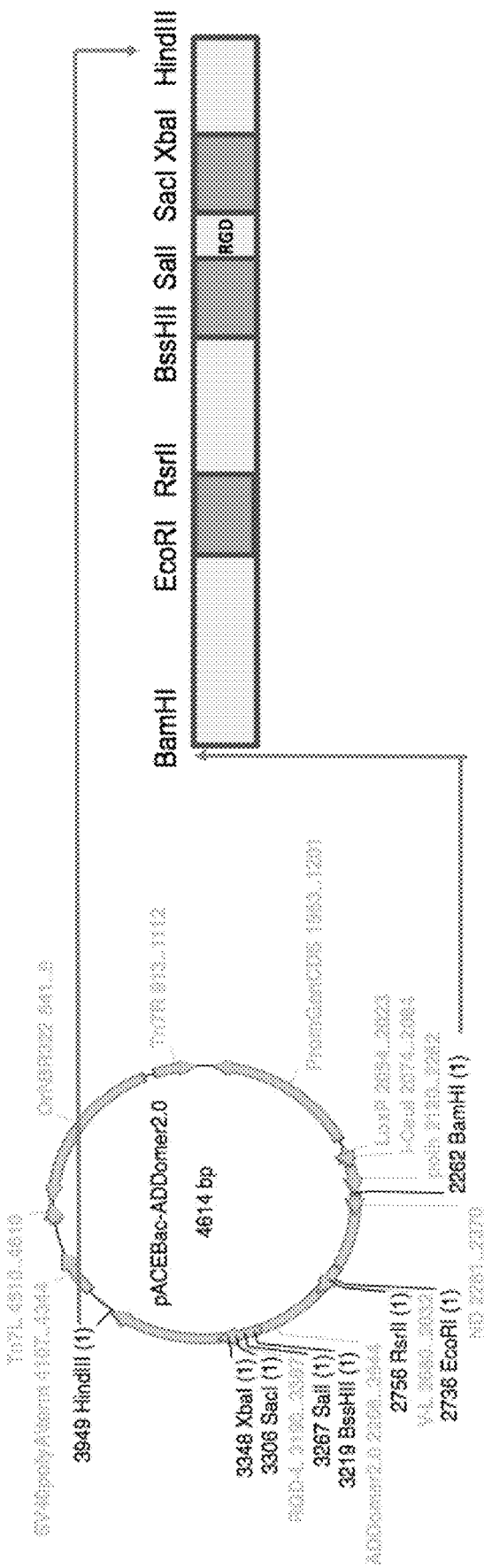

FIG. 9: Plug&Play expression cassette and baculovirus transfer plasmid. The gene encoding ADDomer was designed in order to insert the "epitopes of interest" at three distinct loci (in dark grey) flanked by unique restriction sites. This cassette was inserted in BamHI/HindIII of the pACE-Bac plasmid. BioBrick insertion using either ECoRI/RsrII, BssHII/SalI or SacI/XbaI of the epitope of interest can be easily done in construct pACEBac-ADDomer2.0.

Figure 10:
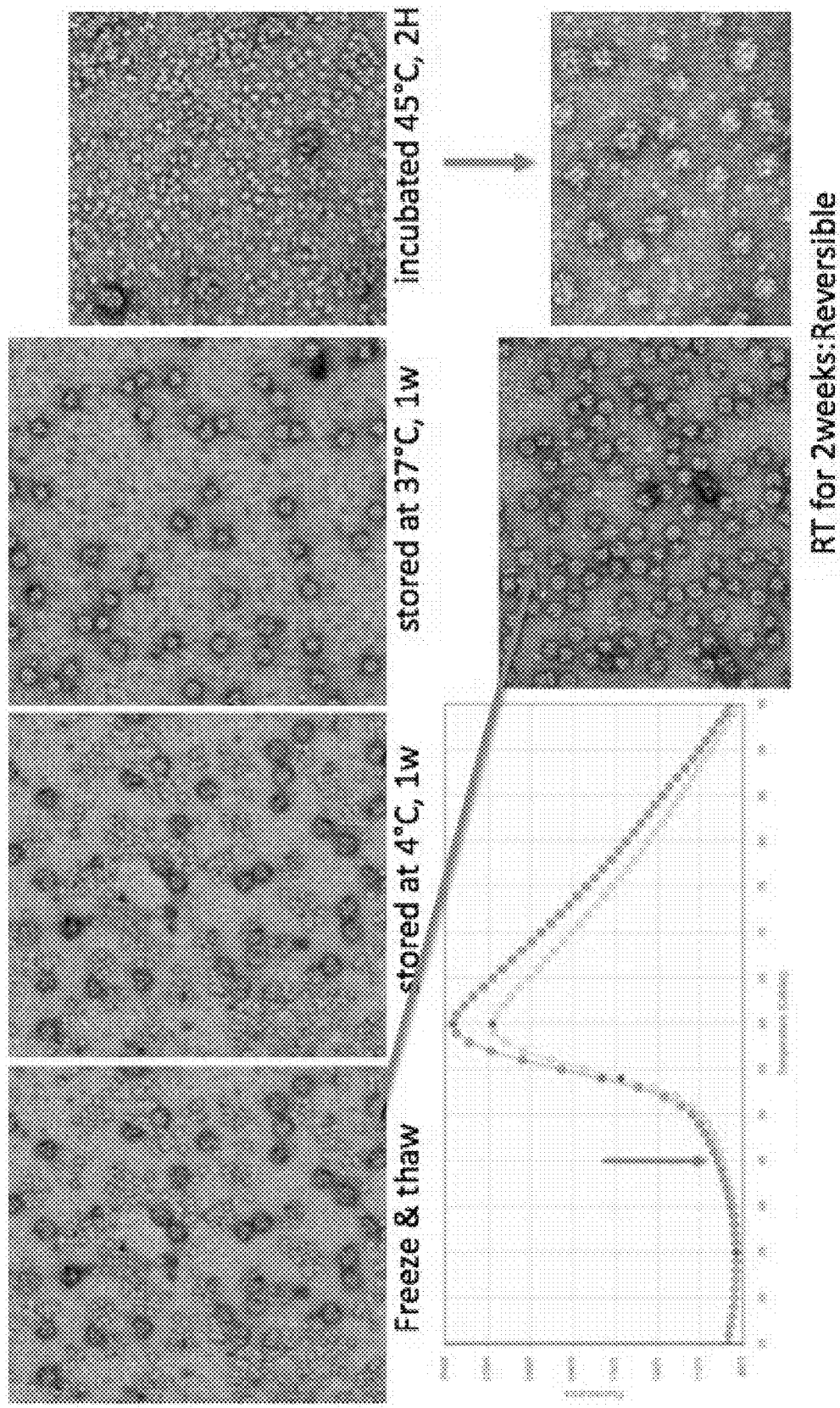

FIG. 10: ADDomer2.0 thermostability. Purified ADDomer was stored at different temperatures followed by electron microscopy. Storage at room temperature or 37° C. resulted in full preservation of the particle. Dissociation in building blocks (pentamer) was observed only for temperature above 45° C. Thermal shift assay (TSA) confirmed stability up to 37° C., an onset of minor dissociation above 45° C., and a total denaturation only by incubation at 60° C.

Figure 11:
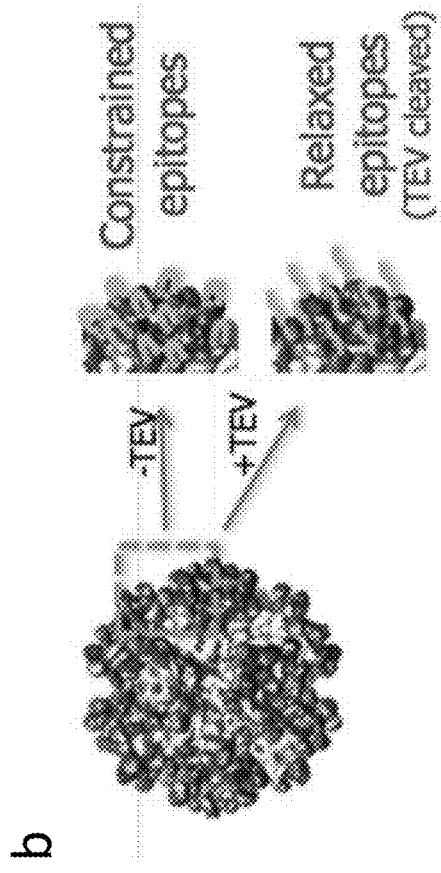

FIG. 11: Chikungunya epitope insertion and mode of epitope display. (a) The amino acids sequence incorporated in a display loop of ADDomer2.0 is shown on top (SEQ ID NO: 78). The major Chikungunya neutralizing epitope (highlighted in dark grey) was inserted. The N-terminus of the peptide contained extra amino acids encoding for a TEV cleavage site (highlighted in light grey). (b) The possibilities of epitope display are explained schematically. Expression results in ADDomer-TevCHIK, in which both ends of the peptide were linked to the ADDomer scaffold ('constrained epitopes'). Incubation with TEV protease released the N-terminus of the peptide in a 'nature-like' configuration ('relaxed epitopes'), while fully maintaining the integrity of the (now multiply nicked) ADDomer VLP. (c) Cleavage was monitored over time by SDS-PAGE analysis showing that intact ADDomer (around 60 kDa) is efficiently cleaved in two bands around 43 and 17 kDa as expected (left). Despite cleavage, electron microscopy confirmed that ADDomer scaffold was not destroyed (right).

Figure 12:
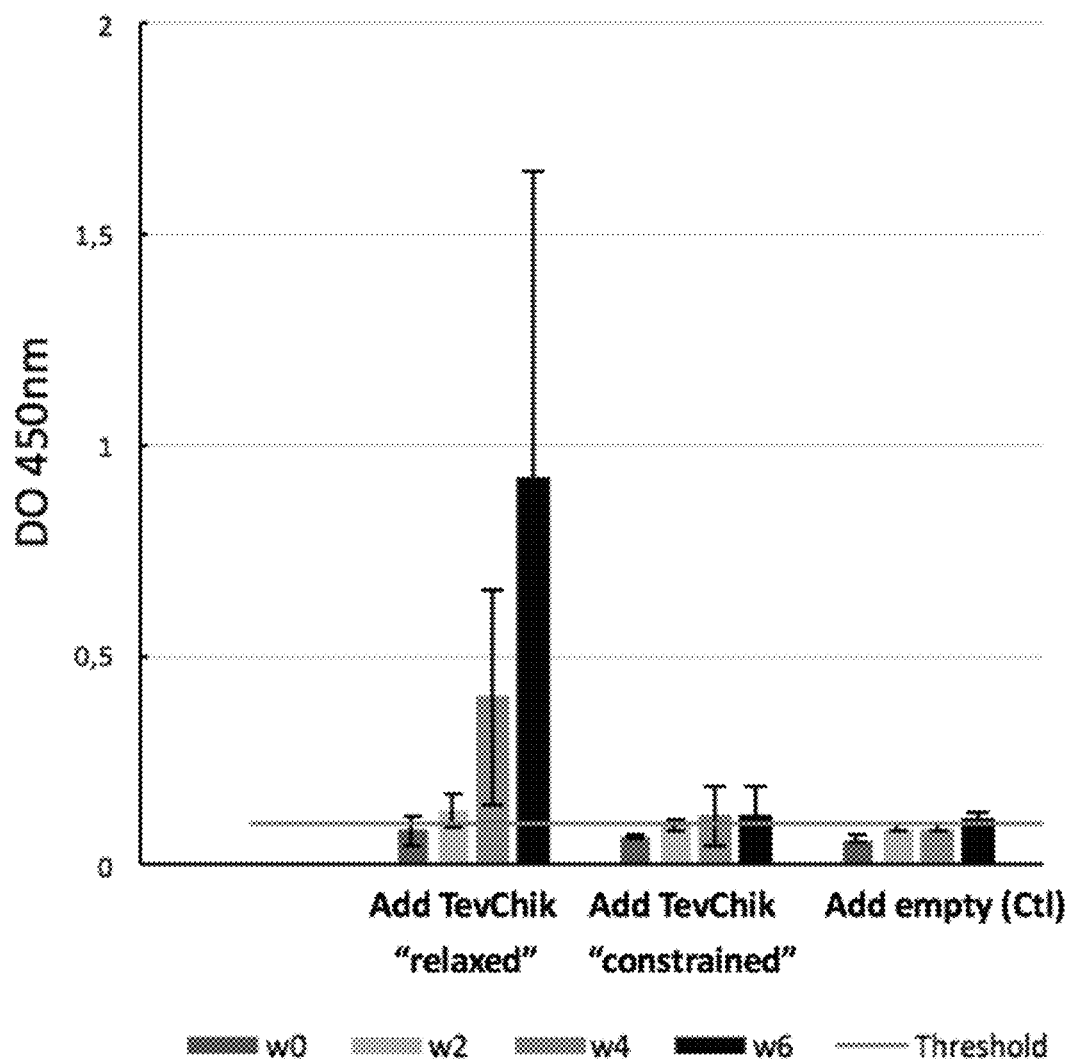

FIG. 12: ELISA of CHIK epitope recognition by mouse sera. Three groups of eight mice were injected at w2 and w4 with 10 mg of either ADDomer scaffold only (no antigenic epitope in epitope presenting loops), ADDomer-TevCHIK-$^{exp}$ (exposed "nature-like" CHIK antigenic epitope in epitope presenting loops, free N-terminal end as in the live Chikungunya glycoprotein, C-terminal end covalently attached to scaffold) or ADDomer-TevCHIK$^{constr}$ ("constrained" CHIK antigenic epitope in epitope presenting loop, N- and C-terminal ends attached to ADDomer scaffold. Sera were collected every two weeks and tested for CHIK antigenic epitope recognition (dilution 1/100). ADDomer-Tev-CHIK$^{exp}$ with exposed, nature-like' epitope efficiently elicits response.

Figure 13:
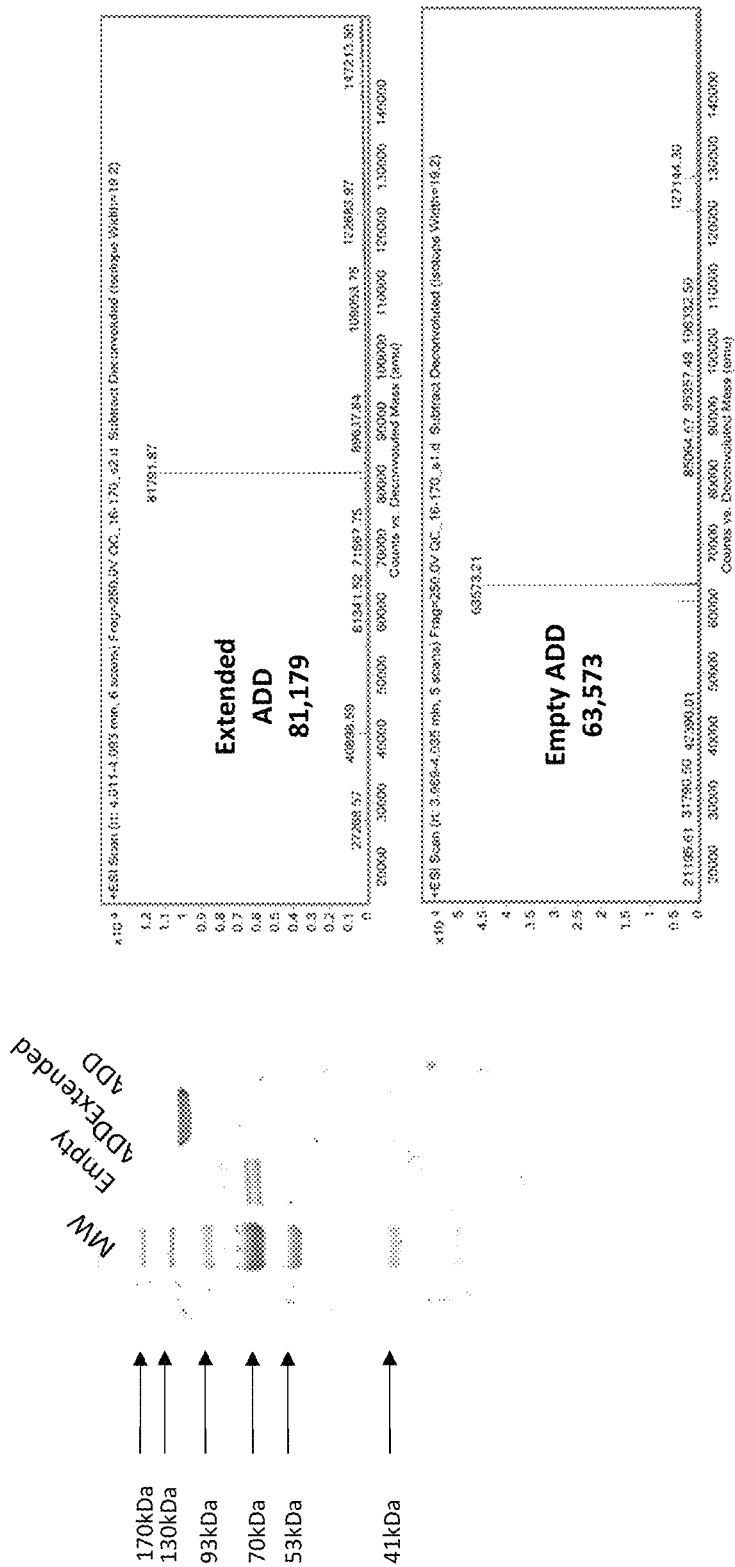

FIG. 13: ADDomer with massively extended epitope presenting loop. A linear epitope encompassing 200 amino acids was inserted into the epitope presenting loops of the ADDomer scaffold and compared to ADDomer scaffold only (without insertion). SDS-PAGE gel evidences the insertion as reflected by the shift to higher molecular weight (left). Mass spectroscopy analysis confirmed the molecular weights (63,573 Da for the ADDomer scaffold without insertion; 81,179 Da for the "extended" ADDomer comprising the extra 200 amino acid insertion in the epitope presenting loops.

FIG. 14: Covalent coupling of "STICKER" peptide to ADDomer containing targeted cystein mutations. Wild-type ADDomer (wt) and ADDomer with one cysteine mutation (K363C, Q476C or A477C, respectively) were incubated with STICKER peptides (C20 (SEQ ID NO: 77) and C9 (SEQ ID NO: 75), respectively). SDS-PAGE analysis was performed under reducing (+bMeSH) and non-reducing (-bMeSH) conditions and transferred to a PVDF membrane. ADDomer (dark grey) and STICKER peptide (light grey) were visualized by binding of labelled antibody and Avidin binding, respectively, evidencing STICKER binding to cysteine-mutant ADDomer by specific disulfide bond formation (marked by white circle in lower panel)

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Definitions

To practice the present invention, unless otherwise indicated, conventional methods of chemistry, biochemistry, and recombinant DNA techniques are employed which are explained in the literature in the field (cf., e.g., *Molecular Cloning: A Laboratory Manual,* 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

The terms "polynucleotide" and "nucleic acid" are used interchangeably herein and are understood as a polymeric or oligomeric macromolecule made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention referred to nucleic acid molecules include but are not limited to ribonucleic acid (RNA), deoxyribonucleic acid (DNA), and mixtures thereof such as e.g. RNA-DNA hybrids. The nucleic acids, can e.g. be synthesized chemically, e.g. in accordance with the phosphotriester method (see, for example, Uhlmann, E. & Peyman, A. (1990) Chemical Reviews, 90, 543-584). "Aptamers" are nucleic acids which bind with high affinity to a polypeptide. Aptamers can be isolated by selection methods such as SELEmir146-a (see e.g. Jayasena (1999) Clin. Chem., 45, 1628-50; Klug and Famulok (1994) M. Mol. Biol. Rep., 20, 97-107; U.S. Pat. No. 5,582,981) from a large pool of different single-stranded RNA molecules. Aptamers can also be synthesized and selected in their mirror-image form, for example as the L-ribonucleotide (Nolte et al. (1996) Nat. Biotechnol., 14, 1116-9; Klussmann et al. (1996) Nat. Biotechnol., 14, 1112-5). Forms which have been isolated in this way enjoy the advantage that they are not degraded by naturally occurring ribonucleases and, therefore, possess greater stability.

The terms "protein" and "polypeptide" are used interchangeably herein and refer to any peptide-bond-linked chain of amino acids, regardless of length or post-translational modification. Proteins usable in the present invention (including protein derivatives, protein variants, protein fragments, protein segments, protein epitopes and protein domains) can be further modified by chemical modification. This means such a chemically modified polypeptide comprises other chemical groups than the 20 naturally occurring amino acids. Examples of such other chemical groups include without limitation glycosylated amino acids and phosphorylated amino acids. Chemical modifications of a polypeptide may provide advantageous properties as compared to the parent polypeptide, e.g. one or more of enhanced stability, increased biological half-life, or increased water solubility.

The term "penton base protein" or "penton base protomer" as used in the context of the present invention refers to an adenoviral protein that assembles into the so called "penton protein". Each penton protein comprises five penton base proteins. The penton protein is one of three proteins forming the adenoviruses coat. The other proteins are hexon and fibre. The structure of an assembled adenovirus is shown in FIG. 1 upper left corner. Penton base proteins that are used in the present invention originate from adenovirus specific to any mammalian species. Preferably the adenovirus is a human or non-human great ape adenovirus, preferably Chimpanzee (Pan), Gorilla (Gorilla) and orangutans (Pongo), more preferably Bonobo (*Pan paniscus*) and common Chimpanzee (*Pan troglodytes*). It is understood by the skilled person that the penton base proteins of different adenovirus will vary in their amino acid sequence all such naturally occurring variants are encompassed by the term "penton base protein". Additionally, the term encompasses artificial variants that comprise insertion, deletions and/or mutations of the naturally occurring penton base protein sequence. These mutations are in addition to the modifications of the N-terminal domain, V loop, first RGD, second RGD loop and/or sticky patch region described in more detail below. Any such artificial variants are comprised in as long as the artificially modified penton base protein assembles into penton subunits and 12 of these assemble into VLPs. Preferably, the artificial variants have at least 75%, more preferably at least 80%, more preferably at least 85%, more preferably at least 90%, more preferably at least 92%, more preferably 94%, more preferably 96%, and more preferably 98% sequence identity to a naturally occurring penton base protomer outside the N-terminal domain, the V loop, the first RGD, and the second RGD loop as defined below. Preferred penton base proteins are those indicated in SEQ ID NOs: 1 to 14. The penton base proteins as defined above are the basis for the engineered penton base proteins of the present invention. Thus, the engineered penton base proteins differ in sequence from naturally occurring penton base proteins by amino acid insertions, deletions and mutations as outlined in more detail below.

The phrase that the "engineered polypeptide is capable of assembling into VLPs" or "assembles into a VLP" as used interchangeably in the context of the present invention refers to the ability of five penton base protomers to self-assemble into a penton protein and subsequently of twelve penton proteins to self-assemble into a small spherically shaped particle, i.e. a virus-like particle (VLP). The ability to assemble and to maintain the penton protein or preferably the VLP structure can be ascertained by methods known in the art and described herein, in particular by electron microscopy (EM). Preferred conditions at which the capability to assemble into VLPs is assessed is 20° C. and physiologic buffer conditions. In a further preferred embodiment the term encompasses engineered polypeptides that not only assemble into VLPs but maintain the spherical shape at temperatures above 20° C., preferably at temperatures above 30° C., preferably at temperatures above 40° C., more preferably above 45° C. and even more preferably above 50° C. The integrity of the spherical shape can be assessed by EM, preferably under physiological buffer conditions.

The term "first RGD-loop" as used in the context of the present invention refers to a polypeptide sequence of between 10 to 40 amino acids that is located N-terminally to the "RGD motif" comprised in the penton protomer (see FIG. 6). This polypeptide sequence is highly divergent between different adenoviruses. Accordingly, it cannot be defined by homology but can be defined by the sequence that is located N-terminally of its N-terminal end. Its C-terminal end within the penton protomer is determined by the RGD motif.

The term "second RGD-loop" as used in the context of the present invention refers to a polypeptide sequence of between 10 to 35 amino acids that is located C-terminally to the "RGD motif" comprised in the penton protomer (see FIG. 6). This polypeptide sequence is highly divergent between different adenoviruses. Accordingly, it cannot be defined by sequence homology. Its N-terminal end within the penton protomer is determined by the RGD motif. Its C-terminal end within the protomer can be defined by the sequence that is located C-terminally of its C-terminal end, which is conserved among different adenoviruses.

The term "RGD motif" as used in the context of the present invention refers to a three amino acid long polypeptide composed of arginine, glycine and aspartic acid. This motif was originally identified in fibronectin as mediating binding to integrins. The RGD-motif is also present in many other receptors and mediates both cell-substrate and cell-cell interactions. The RGD-motif in the penton protomers of the engineered polypeptides of the present invention may be intact or may be mutated in a way that the penton protomer does no longer bind to integrins.

The term "variable loop" as used in the context of the present invention corresponds to a sequence located between the beta sheet sheet b3 and the beta sheet b4 of the adenovirus penton base. Both the length and the aminoacids composition of this loop are are very variable amongst serotypes. The sequences corresponding to variable loops are highlighted in FIG. 6.

The term "N-terminal domain" as used in the context of the present invention refers to a highly conserved region in the N-terminus of the penton base protomer. This part of the protein comprises the a1 and a2 helices, the B1 and B2 sheets as well as the B and C domain (see FIG. 6). It is involved in the interaction between penton base protomers and, thus suitable for the introduction of moieties, e.g. coupling residues that stabilize the interaction between the penton base protomers.

The term "adenovirus fibre protein binding cleft" as used in the context of the present invention refers to a fold of a penton base protomer forming the interaction surface with the adenovirus fibre protein. As can be seen in FIG. 6 the binding cleft is formed by several non-contiguous stretches of polypeptide sequence which are conserved among different adenoviruses.

The term "target specific binding domain" as used throughout the specification refers to a polypeptide which facilitates specific binding to a target. The binding of such a target specific binding domain is considered specific to a given target if it binds with the highest affinity to the respective target and only with lower affinity, e.g. at least 10-fold lower, preferably at least 100-fold lower affinity to other targets even to targets with a related amino acid sequence.

The term "target" as used in the present invention refers to a natural existing cellular or molecular structure towards which molecules have a certain binding affinity or to which molecules specifically bind. A target may comprise one or more epitopes. An antigen is a preferred example of a target.

The term "antigen" as used in the context of the present invention to refer to any structure recognized by molecules of the immune response, e.g. antibodies, T cell receptors (TCRs) and the like. An antigen may be foreign or toxic to the body or may be a cellular protein that is associated with a particular disease. Antigens are recognized by highly variable antigen receptors (B-cell receptor or T-cell receptor) of the adaptive immune system and may elicit a humoral or cellular immune response. Antigens that elicit such a response are also referred to as immunogen. A fraction of the proteins inside cells, irrespective of whether they are foreign or cellular, are processed into smaller peptides and presented to by the major histocompatibility complex (MHC). A cellular immune response is elicited, if the small peptide fragment is bound by a T-cell receptor. Cell surface antigens can be selected from the group of cytokine receptors, integrins, cell adhesion molecules, cell type-specific cell surface antigen, tissue-specific cell surface antigen, cell surface-expressed tumor-associated antigen, cluster of differentiation antigens, or carbohydrates.

The term "specific binding" as used in the context of the present invention to mean that a binding moiety (e.g. an antibody) binds stronger to a target, such as an epitope, for which it is specific compared to the binding to another target if it binds to the first target with a dissociation constant ($K_d$) which is lower than the dissociation constant for the second target. Targets can be recognized by their ligands which bind with a certain affinity to their targets and thus, the ligand binding to its respective target results in a biological effect. Preferably, the binding is both specific and occurs with a high affinity, preferably with $K_d$ of less than $10^{-7}$, $10^{-8}$, $10^{-9}$, $10^{-10}$ M or less. Such affinity is preferably measured at 37° C. Suitable assays include surface plasmon resonance measurements (e.g. Biacore), quartz crystal microbalance measurements (e.g. Attana), and competition assays.

The term "antibodies" as used in the context of the present invention are glycoproteins belonging to the immunoglobulin superfamily; the terms antibody and immunoglobulin are often used interchangeably. An antibody refers to a protein molecule produced by plasma cells and is used by the immune system to identify and neutralize foreign objects such as bacteria and viruses. The antibody recognizes a unique part of the foreign target, its antigen.

The term "antibody fragment" as used herein, refers to one or more fragments of an antibody that retain the ability to specifically bind to an antigen. Examples of binding fragments encompassed within the term "antibody fragment" include a fragment antigen binding (Fab) fragment, a Fab' fragment, a F(ab')$_2$ fragment, a heavy chain antibody, a single-domain antibody (sdAb), a single-chain fragment variable (scFv), a fragment variable (Fv), a $V_H$ domain, a $V_L$ domain, a single domain antibody, a nanobody, an IgNAR (immunoglobulin new antigen receptor), a di-scFv, a bispecific T-cell engager (BITEs), a dual affinity re-targeting (DART) molecule, a triple body, a diabody, a single-chain diabody, an alternative scaffold protein, and a fusion protein thereof.

The term "diabody" as used within this specification refers to a fusion protein or a bivalent antibody which can bind different antigens. A diabody is composed of two single protein chains which comprise fragments of an antibody, namely variable fragments. Diabodies comprise a heavy chain variable domain ($V_H$) connected to a light-chain variable domain ($V_L$) on the same polypeptide chain ($V_H$-$V_L$, or $V_L$-$V_H$). By using a short peptide connecting the two variable domains, the domains are forced to pair with the complementary domain of another chain and thus, create two antigen-binding sites. Diabodies can target the same (monospecific) or different antigens (bispecific).

The term "single domain antibody" as used in the context of the present invention refers to antibody fragments consisting of a single, monomeric variable domain of an antibody. Simply, they only comprise the monomeric heavy chain variable regions of heavy chain antibodies produced by camelids or cartilaginous fish. Due to their different origins they are also referred to VHH or VNAR (variable new antigen receptor)-fragments. Alternatively, single-domain antibodies can be obtained by monomerization of variable domains of conventional mouse or human antibodies by the use of genetic engineering. They show a molecular mass of approximately 12-15 kDa and thus, are the smallest antibody fragments capable of antigen recognition. Further examples include nanobodies or nanoantibodies.

The term "antibody mimetic" as used within the context of the present specification refers to compounds which can specifically bind antigens, similar to an antibody, but are not structurally related to antibodies. Usually, antibody mimetics are artificial peptides or proteins with a molar mass of about 3 to 20 kDa which comprise one, two or more exposed domains specifically binding to an antigen. Examples include inter alia the LACI-D1 (lipoprotein-associated coagulation inhibitor); affilins, e.g. human-γ B crystalline or human ubiquitin; cystatin; Sac7D from *Sulfolobus acidocaldarius*; lipocalin and anticalins derived from lipocalins; DARPins (designed ankyrin repeat domains); SH3 domain of Fyn; Kunits domain of protease inhibitors; monobodies, e.g. the $10^{th}$ type III domain of fibronectin; adnectins: knottins (cysteine knot miniproteins); atrimers; evibodies, e.g. CTLA4-based binders, affibodies, e.g. three-helix bundle from Z-domain of protein A from *Staphylococcus aureus*; Trans-bodies, e.g. human transferrin; tetranectins, e.g. monomeric or trimeric human C-type lectin domain; microbodies, e.g. trypsin-inhibitor-II; affilins; armadillo repeat proteins. Nucleic acids and small molecules are sometimes considered antibody mimetics as well (aptamers), but not artificial antibodies, antibody fragments and fusion proteins composed from these. Common advantages over antibodies are better solubility, tissue penetration, stability towards heat and enzymes, and comparatively low production costs.

As used herein, the term "$K_d$" (usually measured in "mol/L", sometimes abbreviated as "M") is intended to refer to the dissociation equilibrium constant of the particular interaction between a binding moiety (e.g. an antibody or fragment thereof) and a target molecule (e.g. an antigen or epitope thereof). Methods for determining $K_d$ include, without limitation, ELISA and surface plasmon resonance assays.

The term an "epitope", also known as antigenic determinant, as used in the context of the present invention is the part of a macromolecule that is recognized by the immune system, specifically by antibodies, B cells, or T cells. As used herein, an "epitope" is the part of a macromolecule capable of binding to an antibody (e.g. an antibody or antigen-binding fragment thereof) as described herein. Epitopes usually consist of chemically active surface groupings of molecules such as amino acids or sugar side chains and usually have specific three-dimensional structural characteristics, as well as specific charge characteristics. Conformational and non-conformational epitopes can be distinguished in that the binding to the former but not the latter is lost in the presence of denaturing solvents.

As used herein, a "conformational epitope" refers to an epitope of a linear macromolecule (e.g. a polypeptide) that is formed by the three-dimensional structure of said macromolecule. In the context of the present application, a "conformational epitope" is a "discontinuous epitope", i.e. the conformational epitope on the macromolecule (e.g. a polypeptide) which is formed from at least two separate regions in the primary sequence of the macromolecule (e.g. the amino acid sequence of a polypeptide). In other words, an epitope is considered to be a "conformational epitope" in the context of the present invention, if the epitope consists of at least two separate regions in the primary sequence to which an antibody of the invention (or an antigen-binding fragment thereof) binds simultaneously, wherein these at least two separate regions are interrupted by one or more regions in the primary sequence to which an antibody of the invention (or an antigen-binding fragment thereof) does not bind. Preferably, such a "conformational epitope" is present on a polypeptide, and the two separate regions in the primary sequence are two separate amino acid sequences to which an antibody of the invention (or an antigen-binding fragment thereof) binds, wherein these at least two separate amino acid sequences are interrupted by one more amino acid sequences in the primary sequence to which an antibody of the invention (or an antigen-binding fragment thereof) does not bind. Preferably, the interrupting amino acid sequence is a contiguous amino acid sequence comprising two or more amino acids to which the antibody (or the antigen-binding fragment thereof) does not bind. The at least two separate amino acid sequences to which an antibody of the invention (or an antigen-binding fragment thereof) binds are not particularly limited with regard to their length. Such a separate amino acid sequence may consists of only one amino acid as long as the total number of amino acids within said at least two separate amino acid sequences is sufficiently large to effect specific binding between the antibody (or the antigen-binding fragment thereof) and the conformational epitope.

The term "adenovirus fibre protein" as used in the context of the present invention refers to an adenoviral protein that non-covalently binds to a penton protomer and aids in attachment of the adenovirus to the host cell.

The term "sequence identity" is used throughout the specification with regard to polypeptide and polynucleotide sequence comparisons. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise. For example, a polypeptide sequence consisting of 200 amino acids compared to a reference 300 amino acid long polypeptide sequence may exhibit a maximum percentage of sequence identity of 66.6% (200/300) while a sequence with a length of 150 amino acids may exhibit a maximum percentage of sequence identity of 50% (150/300). If 15 out of those 150 amino acids are different from the respective amino acids of the 300 amino acid long reference sequence, the level of sequence identity decreases to 45%. The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, hmmer. wustl. edu/) or with the CLUSTAL algorithm (Thompson, J. D., Higgins, D. G. & Gibson, T. J. (1994) Nucleic Acids Res. 22, 4673-80) available e.g. on ebi. ac. uk/Tools/clustalw/or on ebi.ac.uk/Tools/clustalw2/index.html or on npsa-pbil. ibcp. fr/cgi-bin/npsa_automat.pl?page=/NPSA/npsa_clustalw.html. Preferred parameters used are the default parameters as they are set on bi. ac. uk/Tools/clustalw/or ebi. ac. uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST polynucleotide searches are performed with the BLASTN program, score=100, word length=12. BLAST protein searches are performed with the BLASTP program, score=50, word length=3. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:I54-162) or Markov random fields. When percentages of sequence identity are referred to in the present application, these percentages are calculated in relation to the full length of the longer sequence, if not specifically indicated otherwise. "Hybridization" can also be used as a measure of sequence identity or homology between two nucleic acid sequences. A nucleic acid sequence encoding F, N, or M2-1, or a portion of any of these can be used as a hybridization probe according to standard hybridization techniques. Hybridization conditions are known to those skilled in the art and can be found, for example, in Current Protocols in Molecular Biology, John Wiley & Sons, N. Y., 6.3.1-6.3.6, 1991. "Moderate hybridization conditions" are defined as equivalent to hybridization in 2× sodium chloride/sodium citrate (SSC) at 30° C., followed by a wash in 1×SSC, 0.1% SDS at 50° C. "Highly stringent conditions" are defined as equivalent to hybridization in 6× sodium chloride/sodium citrate (SSC) at 45° C., followed by a wash in 0.2×SSC, 0.1% SDS at 65° C.

The term "coupling residue" as used in the context of the present invention refers to a natural or non-naturally occurring amino acid that has a side chain, capable of forming a covalent bond. Coupling residues can be inserted into a polypeptide of the present invention. If the coupling residue is a naturally occurring amino acid that is encoded by DNA the insertion of a coupling residue merely requires the modification of the DNA that is directing expression of the polypeptide of the invention, e.g. insertion of a codon that encodes such amino acid or mutation of an existing codon. Preferred examples of naturally occurring amino acids that are coupling residues within the meaning of this term are Asp, Glu, Lys and Cys. Cys is particularly preferred since it will form a disulfide bond with another Cys depending on the redox-status of the environment. In particular the latter allows the formation of a stable interconnection between two separate polypeptides.

The term "label" as used in the context of the present invention refers to any kind of compound being suitable for diagnostic purposes. Preferred compounds are selected from a fluorescent dye, a radioisotope and a contrast agent. A contrast agent is a dye or other substance that helps to show abnormal areas inside the body. In one embodiment the term label refers to a compound that comprises a chelating agent which forms a complex with divalent or trivalent metal cations. Preferred radioisotopes/fluorescence emitting isotopes are selected from the group consisting of alpha radiation emitting isotopes, gamma radiation emitting isotopes, Auger electron emitting isotopes, X-ray emitting isotopes, fluorescence emitting isotopes, such as 18F, $^{51}$Cr, $^{67}$Ga, $^{68}$Ga, $^{111}$In, $^{99m}$Tc, $^{140}$La, $^{175}$Yb, $^{153}$Sm, $^{166}$Ho, $^{88}$Y, $^{90}$Y, $^{149}$Pm, $^{177}$Lu, $^{47}$Sc, $^{142}$Pr, $^{159}$Gd, $^{212}$Bi, $^{72}$As, $^{72}$Se, $^{97}$Ru, $^{109}$Pd, $^{105}$Rh, $^{101m15}$Rh, $^{119}$Sb, $^{128}$Ba, $^{123}$I, $^{124}$I, $^{131}$I, $^{197}$Hg, $^{211}$At, $^{169}$Eu, $^{203}$Pb, $^{212}$Pb, $^{64}$Cu, $^{67}$Cu, $^{188}$Re, $^{186}$Re, $^{198}$Au and $^{199}$Ag. Preferred fluorescent dyes are selected from the following classes of dyes: Xanthens (e.g. Fluorescein), Acridines (e.g. Acridine Yellow), Oxazines (e.g. Oxazine 1), Cynines (e.g. Cy7/Cy 3), Styryl dyes (e.g. Dye-28), Coumarines (e.g. Alexa Fluor 350), Porphines (e.g. Chlorophyll B), Metal-Ligand-Complexes (e.g. PtOEPK), Fluorescent proteins (e.g APC, R-Phycoerythrin), Nanocrystals (e.g QuantumDot 705), Perylenes (e.g. Lumogen Red F300) and Phtalocyanines (e.g. IRDYE™700DX) as well as conjugates and combinations of these classes of dyes. Preferred contrast agents are selected from paramagnetic agents, e.g. Gd, Eu, W and Mn, preferably complexed with a chelating agent. Further options are supramagnetic iron (Fe) complexes and particles, compounds containing atoms of high atomic number, i.e. iodine for computer tomography (CT), microbubbles and carriers such as liposomes that contain these contrast agents.

The term "drug" is to be understood in the context of the present invention in its broadest sense to refer to any compound that elicits a prophylactic, therapeutic or palliative effect in a patient. Preferably, it is a small molecule, e.g. with a molecular size of below 500 D.

A "linker" in the context of the present invention refers to any chemical moiety that is flexible and sterically separates two chemical moieties, e.g. an engineered polypeptide of the first aspect of the invention from a drug or label. Preferred linkers are moieties with have a length to width ratio of at least 10:1, preferably of at least 20:1, more preferably of at least 50:1. Preferably, linkers are linear molecules. It is preferred that the two moieties linked by a linker are covalently or non-covalently, preferably covalently attached to the respective ends of the linker.

A "peptide linker" in the context of the present invention refers to an amino acid sequence, i.e. polypeptide, which sterically separates two parts within the engineered polypeptides of the present invention. Typically such linker consists of between 1 and 100, preferably 3 to 50 more preferably 5 to 20 amino acids. Thus, such linkers have a minimum length of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids, and a maximum length of at least 100, 95, 90, 85, 80, 75, 70, 65, 60, 55, 50, 45, 40, 35, 34, 33, 32, 31, 30, 29, 28, 27, 26, 25, 24, 23, 22, 21, 20, 19, 18, 17, 16, or 15 amino acids or less. Peptide linkers may also provide flexibility among the two parts that are linked together. Such flexibility is generally increased, if the amino acids are small. Accordingly, flexible peptide linkers comprise an increased content of small amino acids, in particular of glycins and/or alanines, and/or hydrophilic amino acids such as serines, threonines, asparagines and glutamines. Preferably, more than 20%, 30%, 40%, 50%, 60% or more of the amino acids of the peptide linker are small amino acids.

The terms "preparation" and "composition" are intended to include the formulation of the active compound, e.g. the VLPs of the present invention with a carrier and/or excipient.

"Pharmaceutically acceptable" means approved by a regulatory agency of the Federal or a state government or listed in the U.S. Pharmacopeia or other generally recognized pharmacopeia for use in animals, and more particularly in humans.

The term "carrier", as used herein, refers to a pharmacologically inactive substance such as but not limited to a diluent, excipient, surfactants, stabilizers, physiological buffer solutions or vehicles with which the therapeutically active ingredient is administered. Such pharmaceutical carriers can be liquid or solid. Liquid carrier include but are not limited to sterile liquids, such as saline solutions in water and oils, including but not limited to those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

Suitable pharmaceutical "excipients" include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like.

"Surfactants" include anionic, cationic, and non-ionic surfactants such as but not limited to sodium deoxycholate, sodium dodecylsulfate, Triton X-100, and polysorbates such as polysorbate 20, polysorbate 40, polysorbate 60, polysorbate 65 and polysorbate 80.

"Stabilizers" include but are not limited to mannitol, sucrose, trehalose, albumin, as well as protease and/or nuclease antagonists.

"Physiological buffer solution" that may be used in the context of the present invention include but are not limited to sodium chloride solution, demineralized water, as well as suitable organic or inorganic buffer solutions such as but not limited to phosphate buffer, citrate buffer, tris buffer (tris (hydroxymethyl)aminomethane), HEPES buffer ([4 (2 hydroxyethyl)piperazino]ethanesulphonic acid) or MOPS buffer (3 morpholino-1 propanesulphonic acid). The choice of the respective buffer in general depends on the desired buffer molarity. Phosphate buffer are suitable, for example, for injection and infusion solutions.

The term "adjuvant" refers to agents that augment, stimulate, activate, potentiate, or modulate the immune response to the active ingredient of the composition at either the cellular or humoral level, e.g. immunologic adjuvants stimulate the response of the immune system to the actual antigen, but have no immunological effect themselves. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g polyarginine or polylysine).

An "effective amount" or "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Embodiments

The present invention provides inter alia the following advantages over the prior art: (i) an easily modified scaffold for antigen and/or target specific binding domain insertion/presentation, which can be tailored to the need of a patient or easily adapted to the changing surface antigens of viruses, (ii) a stable composition that can be used for, e.g. vaccination even under adverse storage conditions, e.g. high heat, (iii) an extremely high density vehicle for presenting one or multiple antigens, (iv) the use of a fibre (STICKER) protein to add further antigens or other activities on the fly.

Accordingly, in a first aspect the present invention relates to an engineered polypeptide comprising, essentially consisting or consists of an adenovirus penton base protomer, wherein said penton base protomer comprises a first RGD-loop, a second RGD-loop, a variable loop (V loop), adenovirus fibre protein binding cleft and/or a N-terminal domain, and comprises one or more of the following:
  (i) at least one target specific binding domain in the first, the second or both the first and the second RGD-loops, and/or in the V loop; and/or
  (ii) one or more non-adenoviral polypeptides in the first, the second or both the first and the second RGD-loops and/or in the V loop; and/or
  (iii) a non-adenoviral polypeptide at the N- and/or C-terminus of the penton base protomer; and/or
  (iv) at least one heterologous coupling residue in the first, the second, or both the first and the second RGD-loops, in the V loop and/or in the N-terminal domain of the penton base protomer, wherein the N-terminus of the N-terminal domain within the penton base protomer is defined as follows:

$$X_1\text{-}G\text{-}R\text{-}N\text{-}S\text{-}I\text{-}R \quad (\text{SEQ ID NO: 44})$$

and the C-terminus of the N-terminal domain within the penton base protomer is defined as follows:

$$D\text{-}X_2\text{-}R\text{-}S\text{-}R\text{-}G, \quad (\text{SEQ ID NO: 45})$$

wherein
$X_1$ is selected from the group consisting of G and E, preferably E, and
$X_2$ is selected from the group consisting of D and E, preferably E; and/or
  (v) a drug, label and/or polypeptide covalently or non-covalently coupled to one or more amino acids of the first, the second or both the first and the second RGD-loops and/or one or more amino acids of the V loop of the penton base protomer; and/or
  (vi) at least one heterologous coupling residue in the adenovirus fibre protein binding cleft of the penton base protomer and wherein the engineered polypeptide is preferably capable of assembling into VLPs.

If in one of above embodiments a residue or group of residues, e.g. a target specific binding domain, one or more non-adenoviral polypeptides or at least one heterologous coupling residue, is indicated to be comprised in a certain region of the penton base protein this residue or group of residues may be inserted within the respectively indicated region of the penton base protein, i.e. may be an addition, or it may be inserted and additional at least one or all of the amino acids forming the respectively indicated first RGD-loop, second RGD-loops and/or in V loop may be deleted without affecting the capability to assemble into VLPs.

A preferred embodiment of the engineered polypeptide of the first aspect of the invention comprises, essentially consists or consists of an adenovirus penton base protomer, wherein said penton base protomer comprises a first RGD-loop, a second RGD-loop, a variable loop (V loop), adenovirus fibre protein binding cleft and/or a N-terminal domain, and comprises one or more non-adenoviral polypeptides in the first, the second or both the first and the second RGD-loops and/or in the V loop; and optionally further comprises one or more of the following:
  (i) comprising at least one target specific binding domain in the first, the second or both the first and the second RGD-loops, and/or in the V loop; and/or
  (ii) a non-adenoviral polypeptide at the N- and/or C-terminus of the penton base protomer; and/or
  (iii) at least one heterologous coupling residue in the first, the second, or both the first and the second RGD-loops, in the V loop and/or in the N-terminal domain of the penton base protomer, wherein the N-terminus of the N-terminal domain within the penton base protomer is defined as follows:

$$X_1\text{-}G\text{-}R\text{-}N\text{-}S\text{-}I\text{-}R \quad (\text{SEQ ID NO: 44})$$

and the C-terminus of the N-terminal domain within the penton base protomer is defined as follows:

$$D\text{-}X_2\text{-}R\text{-}S\text{-}R\text{-}G, \quad (\text{SEQ ID NO: 45})$$

wherein
$X_1$ is selected from the group consisting of G and E, preferably E, and
$X_2$ is selected from the group consisting of D and E, preferably E; and/or
  (iv) a drug, label and/or polypeptide covalently or non-covalently coupled to one or more amino acids of the first, the second or both the first and the second RGD-loops and/or one or more amino acids of the V loop of the penton base protomer; and/or
  (vi at least one heterologous coupling residue in the adenovirus fibre protein binding cleft of the penton base protomer and wherein the engineered polypeptide is preferably capable of assembling into VLPs.

The at least one target specific binding domain in the first, the second or both the first and the second RGD-loops, and/or in the V loop provides the penton base protomer and accordingly the assembled VLP with the ability to specifically bind to a target structure, e.g. a cellular receptor on the surface of a cell. It is a surprising discovery of the present inventors that these parts of the penton base protomer can comprise a target specific binding domain of considerable length without disrupting penton or VLP formation. Additionally, the target specific binding domain comprised in these regions is free to interact with and bind to targets. The one or more target specific binding domains may be inserted at any point in the respective loops, i.e. without removing any of the loop amino acids. Alternatively, all or part of the respective loop amino acids may be replaced by the amino acids of the target specific binding domain. The target specific binding domain may be flanked N- and/or C-terminally by peptide linkers.

If the penton base protomer comprises more than one target specific binding domain, it is preferred that these are comprised in different loops of the penton base protomer, e.g. in the first and second RGD-loop, in the first RGD-loop and the V-loop, or the second RGD-loop and the V-loop. If the penton base protomer comprises more than one target specific binding domain it is also preferred that they bind to different targets, e.g. to a target on a first type of cell and to a different target on a second type of cell. Such dual or multiple specificities can be used to bring together cells that do not normally or not frequently enough interact with each other. Examples of such cells are tumor cells and cells of the immune system, in particular cytotoxic T cells.

In an alternative embodiment (ii) that can be combined with one or more of the other alternative embodiments outlined above the first, the second or both the first and the second RGD-loops and/or in the V loop comprise a non-adenoviral polypeptide. This embodiment is also based on the surprising observation that polypeptides inserted into one or more of these regions of the penton base protomer are sufficiently exposed to be recognized by cells of the immune system and, thus to elicit an immune response. The term "non-adenoviral" polypeptide refers to a polypeptide that has no sequence identity to any polypeptide present in an adenovirus, in particular in naturally occurring adenovirus penton base protomers over a length of at least 5 amino acids. Preferably, the non-adenoviral polypeptide has no sequence identity to any polypeptide present in adenovirus over a stretch of at least 10, preferably at least 15 amino acids. The one or more non-adenoviral polypeptides may be inserted in each case independently at any point in the respective loops, i.e. without removing any of the loop amino acids. Alternatively, all or part of the respective loop amino acids may be replaced by the amino acids of the target specific binding domain. The non-adenoviral polypeptide comprised in one or more of the loops may be flanked N- and/or C-terminally by peptide linkers. This may be preferred to increase exposure of the non-adenoviral polypeptide on the surface of the VLP. If at least one non-adenoviral polypeptide is inserted into each loop than each penton base protomer comprises at least three identical or different non-adenoviral polypeptides on its surface. Once assembled into VLPs at least 180 non-adenoviral polypeptides may be displayed at the surface of the VLPs of the present invention.

The present inventors have surprisingly found that long amino acid sequences of 50 or more, 100 or more, 150 or more, 200 or more, 250 or more or 300 or more amino acids may be introduced into the first, the second or both the first and the second RGD-loops, and/or in the V loop without disrupting the penton base protomers ability to assemble into penton proteins and subsequently into VLPs. Thus, in the embodiment indicated under (i) and/or (ii) amino acid sequences of above indicated length may be inserted (with or without deletion of some of the amino acids with the respective loops).

If the alternative embodiments indicated under (i) and (ii) are combined, it is further preferred that the non-adenoviral protein is inserted into a different loop than the target specific binding domain.

The present inventors have observed that polypeptides positioned at either N- and/or C-terminus of the penton base protomer do not interfere with penton and subsequently VLP assembly and are surface exposed in an assembled VLP. Thus, in a further alternative embodiment (iii) a non-adenoviral polypeptide may be linked with or without intervening peptide linker to the N- and/or C-terminus of the penton base protomer. Accordingly, if combined with the first and/or second embodiment a penton base protomer may comprise non-adenoviral polypeptides in one or more of the loops, preferably all three loops and at the N-terminus, C-terminus or N- and C-terminus. It is preferred that this alternative embodiment is combined with at least one of the other alternative embodiments (i), (iii), (iv), (v) and/or (vi).

The observations of the present inventors relating to the possibility to insert heterologous peptide sequence into the V-loop, the first RGD-loop and/or the second RGD-loop (with or without concomitant deletion of all or part of the respectively indicated loop) led to a further alternative embodiment (iv) that may be combined with one or more of the previously discussed alternative embodiments. In this embodiment at least one heterologous coupling residue is introduced in the first, the second, or both the first and the second RGD-loops and/or in the V loop. By the insertion of one or more coupling residues it becomes possible to covalently couple further molecules to the loops. It is, for example envisioned that a VLP is first assembled from the engineered polypeptide of the first aspect comprising one or more coupling residue in one or more of the loops and that subsequently a polypeptide also comprising a coupling residue is coupled covalently to the VLP. Using this strategy it is possible to "decorate" the surface of the VLP with polypeptides. Such VLPs may be used to elicit a humoral and/or cellular immune response against such polypeptides.

Furthermore, the present inventors have identified a region within the penton base protomer referred to as the "N-terminal domain of the penton base protomer". This domain is involved in the interaction between the penton base protomers within penton and also in the interaction among pentons forming a VLP. The insertion of coupling residues into this region allows the formation of covalent bonds between two or more penton base protomers within the same or separate pentons. The formation of such covalent bonds stabilizes the penton as well as the assembled VLP. The N-terminal domain is highly conserved among different adenovirus species. It is, therefore possible to further delineate the N-terminal and C-terminal end of this domain within the penton base protomer. Thus, it is preferred that one or more the coupling residues are comprised in the N-terminal domain. The coupling residue may replace an existing amino acid or may be inserted in addition to the amino acids forming the N-terminal domain. It is preferred that the one or more coupling residue replace a residue within the N-terminal domain. The N-terminus of the N-terminal domain within the penton base protomer is preferably defined as follows:

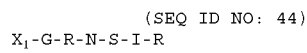
(SEQ ID NO: 44)
X₁-G-R-N-S-I-R and the C-terminus of the N-terminal domain within the penton base protomer is preferably defined as follows:

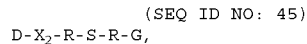
(SEQ ID NO: 45)
D-X₂-R-S-R-G, wherein

X₁ is selected from the group consisting of G and E, preferably E, and

X₂ is selected from the group consisting of D and E.

Accordingly, in this alternative embodiment (iv) one or more coupling residues are comprised within the amino acid sequence of the penton base protomer comprised in the engineered polypeptide of the present invention delimited by above N- and C-terminal region. It will be understood by the skilled person that it is also possible in this embodiment to replace one or more amino acid residues within SEQ ID NO: 44 or 45. The coupling residue may be positioned anywhere within the N-terminal domain in as long as it does not interfere with assembly of penton or VLP.

A preferred protomer amino acid sequence that can be modified according to alternatives (i) to (vi) of the first embodiment is SEQ ID NO: 64 (the encoding nucleotide sequence is indicated in SEQ ID NO: 63). It is preferred that the insertions of at least one target specific binding domain according to embodiment (i), and/or the insertion of one or more non-adenoviral peptides according to embodiment (ii), and/or the insertion of at least one heterologous coupling residue according to embodiment (iv), and/or the covalent or non-covalent coupling of the drug or polypeptide to one or more amino acids of the first, the second or both the first and the second RGD-loops and/or one or more amino acids of the V loop according to embodiment (v) occurs in the first RGD-loop between amino acids 312 to 339 of SEQ ID NO: 64 and/or in the second RGD-loop between amino acids 343 to 367 of SEQ ID NO: 64 and/or in the V loop between amino acids 150 to 178 of SEQ ID NO: 64. Such insertion(s) may delete all or part of the respectively indicated amino acids belonging to the first and second RGD loop and the V loop.

Preferably, there has to be a PAIR of coupling residues, preferably mutations to cysteines to enable disulfide bond formation. The resulting stabilized VLP contains up to 120 disulfide bonds and is hyperstable at 37° C. and even at 42° C., at least for several months. In a particularly preferred embodiment the coupling residues are located at amino acid position 51 and 54 with reference to SEQ ID NO: 64, i.e. a preferred penton base protomer amino acid sequence based on human Ad B3 or at analogous positions of a penton base protomer of another adenovirus, or at amino acid position 54 and 114 with reference to SEQ ID NO: 64 or at analogous positions of a penton base protomer of another adenovirus.

It has been further discovered that a coupling residue at amino acid position 53 (with reference to SEQ ID NO: 1) can form a covalent bond with a coupling residue at amino acid position 543 (with reference to SEQ ID NO: 64) or at analogous positions of a penton base protomer of another adenovirus. The latter residue is outside the N-terminal domain. Thus, if a coupling residue is inserted at position 53 it is preferred that a second coupling residue is positioned at amino acid 541 with reference to SEQ ID NO: 64 or at analogous positions of a penton base protomer of another adenovirus. With reference to FIG. 6 and by including further penton base proteins in the alignment the skilled person can easily determine those residues in the respective penton base protomer that occupies an analogous position as amino acids. 51, 53, 54, 114 and 541 of SEQ ID NO: 64.

It is preferred in this embodiment of the engineered polypeptide of the present invention that the penton base protomer comprises the following sequences:

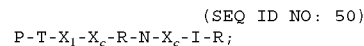
(SEQ ID NO: 50)
P-T-X₁-X_c-R-N-X_c-I-R;

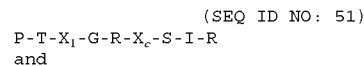
(SEQ ID NO: 51)
P-T-X₁-G-R-X_c-S-I-R
and

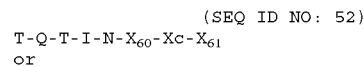
(SEQ ID NO: 52)
T-Q-T-I-N-X₆₀-Xc-X₆₁
or

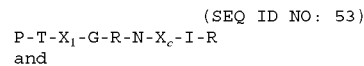
(SEQ ID NO: 53)
P-T-X₁-G-R-N-X_c-I-R
and

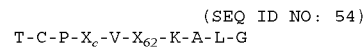
(SEQ ID NO: 54)
T-C-P-X_c-V-X₆₂-K-A-L-G wherein

X₁ is selected from the group consisting of G and E, preferably E

X_e in each case is a coupling residue, preferably C; D, E, and K, most preferably C;

X₆₀ is selected from the group consisting of F, I, and L, preferably F and L, most preferably F, X₆₁ is selected from the group consisting of D and E, preferably E; and X₆₂ is selected from the group consisting of H and Y, preferably Y.

Particularly, preferred stabilized penton base protomers comprise or consist of the amino acid sequences according to SEQ ID NO: 65 to 67. It is further preferred that these amino acid sequences comprise one or more of the modifications according to alternative embodiments (i), (ii), (iii), (iv) in as far as this alternative embodiment is not relating to the N-terminal domain, (v) or (vi) of the first aspect of the invention described above.

It is preferred that the insertions of at least one target specific binding domain according to embodiment (i), and/or the insertion of one or more non-adenoviral peptides according to embodiment (ii), and/or the insertion of at least one heterologous coupling residue according to embodiment (iv), and/or the covalent or non-covalent coupling of the drug or polypeptide to one or more amino acids of the first, the second or both the first and the second RGD-loops and/or one or more amino acids of the V loop according to embodiment (v) occurs in the first RGD-loop occurs between amino acids 312 to 339 of SEQ ID NO: 65 to 67 and/or that the insertion into the second RGD-loop occurs between amino acids 343 to 367 of SEQ ID NO: 65 to 67 and/or that the insertion into the V loop occurs between amino acids 150 to 178 of SEQ ID NO: 65 to 67. Such insertion(s) may delete all or part of the respectively indicated amino acids belonging to the first and second RGD loop and the V loop.

The thermal stabilization of penton and VLPs formed by the engineered proteins of the present invention is desirable also in the context of any of the other alternative embodiments of the engineered protein of the present invention. Accordingly, the alternative embodiment mentioned under (iv) above in relation to the N-terminal domain is preferably combined with one or more alternative embodiments (i), (ii), (iii), (iv) in as far as this alternative embodiment is not relating to the N-terminal domain, (v) or (vi). It is also preferred that the alternative embodiments mentioned under (iv) and (vi) are present in the engineered penton base protomer and are combined with one or more of (i), (ii), (iii), (iv) in as far as this alternative embodiment is not relating to the N-terminal domain, or (v).

In a further alternative embodiment (v) of the first aspect of the invention that may be combined with one or more of the other alternative embodiments of the first aspect of the invention a drug, label and/or polypeptide is covalently or non-covalently coupled to one or more amino acids of the first, the second or both the first and the second RGD-loops and/or one or more amino acids of the V loop of the penton base protomer. Again this embodiment is based on the observation that the coupling of moieties to these regions does not interfere with penton and VLP assembly and leads to decoration of the VLP with these moieties. In a preferred embodiment the drug or label is attached to the penton base protomer through a linker, preferably a peptide linker, that is cleavable under physiologic condition, e.g. a protease thereby releasing the drug from the VLP at the site of action. In this preferred embodiment the linker, preferably peptide linker comprises an endopeptidase cleavage site.

In a preferred embodiment a fragment of adenoviral fibre is used to non-covalently attach a moiety, e.g. a polypeptide, drug, or label etc. to the penton base protomer, the assembled penton and/or the assembled VLP. This interaction is mediated via the adenovirus fibre protein binding cleft of the penton base protomer that is present in the engineered polypeptide of the first aspect of the invention. In a preferred embodiment described below the fibre fragment comprises a heterologous coupling residue for covalent attachment of the fibre fragment to the penton base protomer. Since a coupling residue requires a counter-part, i.e. a residue with which it can form a covalent bond, it is a further preferred alternative embodiment (vi) of the engineered protein of the first aspect of the invention that at least one heterologous coupling residue is comprised in the adenovirus fibre protein binding cleft of the penton base protomer. The coupling residue in the binding cleft and the fibre protein fragment are positioned in such as to allow formation of a covalent bond once the fibre protein fragment is bound in the cleft of the penton base protomer.

Each penton base protomer interacts with one adenovirus fibre protein via the highly conserved region referred to herein as the "adenovirus fibre protein binding cleft of the penton base protomer". This interaction is used to indirectly attach a further moiety, preferably a polypeptide, a drug or label to the penton base protomer and to present upon assembly of 60 penton base protomers of the present invention up to 60 further moieties on the surface of the assembled VLP. Accordingly, in a second aspect the present invention relates to an engineered polypeptide comprising, essentially consisting or consisting of at least one adenovirus fibre protein N-terminal fragment specifically binding to an adenovirus fibre protein binding cleft of a penton base protomer and:
(i) a non-adenoviral peptide, and/or
(ii) is covalently or non-covalently coupled to a drug or label.

The at least one adenovirus fibre protein N-terminal fragment specifically binding to an adenovirus fibre protein binding cleft of a penton base protomer comprised in the engineered polypeptide of the second aspect of the invention is throughout this specification also referred to as STICKER.

Surprisingly, a relatively small N-terminal fragment of adenovirus fibre protein was sufficient to specifically bind to a penton base protomer. The smaller the fibre fragment the bigger the moiety that can be attached to the penton base protomer. Furthermore, the reduction of the length of the adenoviral fibre fragment reduces the likelihood that a new immune response is elicited against adenovirus fibre and/or that fibre bound to VLPs are cleared by pre-existing anti-fibre antibody. It is, thus preferred that the fibre fragment has a length of 50 contiguous amino acids or less of N-terminal fibre sequence. It is more preferred that the length of the fragment is 40 amino acids or less, 35 amino acids or less, 30 amino acids or less, 25 amino acids or less or 20 amino acids or less. The minimal fibre amino acid sequence required for specific binding to the binding cleft of the penton base protomer is F-N-P-V-Y-P-Y (amino acids 2-8 of SEQ ID NO:43). This minimal sequence is preferably flanked by other adenovirus fiber, preferably Ad3 amino acid sequence on both sides. This small fragment can be used for extending the versatility and/or the number or exposed epitope on the VLP surface. Alternatively, addition of the STICKER tag to any protein or epitope sequence enables their binding to the VLP surface. This is done by in vitro incubation of the STICKER containing protein with the VLP or by co-expression of both components in a baculovirus system.

It is preferred that the engineered polypeptide does not comprise any further fibre amino acid sequence contiguous with STICKER. More preferably the polypeptide of the second aspect of the invention does not comprise any other adenovirus proteins or polypeptides other than STICKER.

It has been surprisingly found that STICKER can be attached N- and/or C-terminally without interfering with its binding to a penton base protomer. Preferably, STICKER is attached to the N-terminus of a non-adenoviral polypeptide. This polypeptide can be any polypeptide for which it is desired to attach it to the surface of the VLPs of the present invention. The size of the polypeptide that is attached to STICKER is not particularly limited. It can be any size that still allows specific binding to the fibre protein binding cleft of a penton base protomer. The engineered polypeptide may further comprise a peptide linker between the non-adenoviral polypeptide and STICKER. This may be required, if the non-adenoviral polypeptide has a size that prevents 60 of such polypeptides to bind via STICKER to the assembled VLP. A peptide linker may also be advantageous in situations in which the N- and/or C-terminus to which STICKER is attached is buried within the polypeptide.

The majority of the human population has been exposed to human Ad5 and have memory B cells capable of mounting an immune response against human Ad5. Accordingly, if human Ad5 based protomers and/or fibre are comprised in the engineered proteins of the first and second aspect of the invention, the resulting VLPs are more likely to be cleared from the circulation by a pre-existing immunity. Thus, in a preferred embodiment the adenoviral proteins comprised in the engineered polypeptide according to the first and/or second aspect of the invention is based on adenovirus penton and fibre proteins, respectively, from human or non-human great ape adenoviruses, preferably from Chimpanzee (Pan) adenoviruses, Gorilla (Gorilla) adenoviruses and orangutans (Pongo) adenoviruses, more preferably Bonobo (*Pan paniscus*) and common Chimpanzee (*Pan troglodytes*).

It is particularly preferred that the engineered polypeptide comprising an adenovirus penton base protomer and the engineered polypeptide comprising at least one adenovirus penton base protomer binding fibre protein fragment are based on penton and fibre proteins, respectively, of adenovirus selected from the group consisting of hAd3, hAd4, hAd5, hAd7, hAd11, hAd26, hAd35 and hAd49, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82, PanAd1, PanAd2, PanAd3, ChAd55, ChAd73, ChAd83, ChAd146, and ChAd147 described in WO 2005/071093 and WO 2010/086189.

The engineered polypeptide of the first aspect of the invention is preferably based on the wild-type penton base protomer of SEQ ID NO: 1 to 14, i.e. SEQ ID NO: 1 to 14 reflects the sequence of the protein prior to modification according to alternative embodiments (i) to (vi) outlined above. It will be understood by the skilled person that the insertion of a target specific binding domain into the V-loop, first and/or second RGD loop will alter the sequence in that part of SEQ ID NO: 1 to 14. Similarly, the replacement of amino acids with coupling residues will also alter the amino acid sequence.

The modifications according to (i) and (ii) above require the modification of one or both of the RGD loops and/or the V loop. In a preferred embodiment of the engineered polypeptide of the invention the region to be modified are defined by consensus sequences common to the majority of adenoviruses. Thus, these consensus sequences are based on the alignment of several preferred penton base protomer amino acid sequences from adenoviral species and are, suitable to determine the N- and C-terminus respectively, of the part of the penton base protein to modify according to embodiment (i) or (ii) noted above. Preferably, the N-terminus of the first RGD-loop within the penton base protomer is defined as follows:

(SEQ ID NO: 15)
$X_3-X_4-X_5-X_6-X_7-X_8-X_9-X_{10}-X_{11}$ wherein
$X_3$ is selected from the group consisting of D, E and N, and is preferably D;
$X_4$ is selected from the group consisting of V, L, and I, and is preferably V;
$X_5$ is any amino acid, is preferably selected from the group consisting of A, D, E, K, S, and T, and is more preferably T;
$X_6$ is any amino acid, is preferably selected from the group consisting of A, D, E, and K, and is more preferably A;
$X_7$ is selected from the group consisting of F, Y, and W, and is preferably Y;
$X_8$ is selected from the group consisting of A, D, E, N, and Q, is preferably E or Q, and is more preferably E;
$X_9$ is any amino acid, preferably selected from the group consisting of A, D, E, N, and K, and is more preferably E;
$X_{10}$ is selected from the group consisting of S or T, and is preferably S; and
$X_{11}$ is any amino acid and constitutes the N-terminal amino acid of the first RGD loop; and/or the following sequence defines the C-terminus of the first RGD-loop and at the same time the N-terminus of the second RGD-loop within the penton base protomer:

(SEQ ID NO: 16)
$X_{12}-X_{13}-X_{14}-X_{15}-X_{16}$ wherein
$X_{12}$ is any amino acid and constitutes the C-terminal amino acid of the first RGD loop;
$X_{13}$ is R;
$X_{14}$ is G;
$X_{15}$ is D; and
$X_{16}$ is any amino acid and the N-terminal amino acid of the second RGD loop;
and/or
the following sequence constitutes the C-terminus of the second RGD-loop within the penton base protomer:

(SEQ ID NO: 17)
$X_{15}-X_{16}-X_{17}-X_{18}-X_{19}-X_{20}-X_{21}-X_{22}$;

wherein
$X_{17}$ is any amino acid and constitutes the C-terminal amino acid of the second RGD loop;
$X_{18}$ is selected from the group consisting of I, L and V, and is preferably I;
$X_{19}$ is selected from the group consisting of D, E, K, N, Q, and V, is preferably Q or K, and is more preferably Q;
$X_{20}$ is selected from the group consisting of C, G and P, and is preferably P;
$X_{21}$ is selected from the group consisting of I, L and V, is preferably L or V and is more preferably L;
$X_{22}$. is selected from the group consisting of D, E, S and T, is preferably E or T and is more preferably E;
$X_{23}$ is selected from the group consisting of D, E, K, S and T, is preferably E, K or T, and is more preferably K; and
$X_{24}$ is selected from the group consisting of D and E, and is preferably D.

Similarly, the following sequence defines the N-terminus of the V loop of a penton base protomer:

(SEQ ID NO: 18)
$X_{25}-X_{26}-X_{27}-X_{28}-X_{29}-X_{30}-X_{31}-X_{32}$.

wherein
$X_{25}$ is selected from the group consisting of F, Y, and W, and is preferably F;
$X_{26}$ is selected from the group consisting of H, K and R, and is preferably K;
$X_{27}$ is selected from the group consisting of A, V, I, and L, and is preferably A;
$X_{28}$ is selected from the group consisting of H, K, and R, and is preferably R;
$X_{29}$, is selected from the group consisting of A, V, I, and L, and is preferably V;
$X_{30}$ is selected from the group consisting of A, V, I, L and M, and is preferably M;
$X_{31}$ is selected from the group consisting of A, V, I, and L, and is preferably V; and
$X_{32}$ is any amino acid and constitutes the N-terminal amino acid of the V-loop;
and/or
the following sequence defines the C-terminus of the V loop $X_{33}-X_{34}-X_{35}-X_{36}-X_{37}-X_{38}-X_{39}$ (SEQ ID NO: 19)

wherein $X_{33}$ is any amino acid and constitutes the C-terminal amino acid of the V-loop;

$X_{34}$ is selected from the group consisting of F, Y, and W, and is preferably Y;

$X_{35}$ is selected from the group consisting of D, E, S and T, is preferably E or T and is more preferably E;

$X_{36}$ is selected from the group consisting of F, Y, and W, and is preferably W;

$X_{37}$ is selected from the group consisting of A, F, V, Y, and W, is preferably F or V and is more preferably F;

$X_{38}$ is selected from the group consisting of D, E, S, and T, is preferably D, and E and is more preferably E; and $X_{39}$ is selected from the group consisting of F, Y, and W, and is preferably F.

$X_{32}$ is the N-terminal amino acid and $X_{33}$ is the C-terminal amino acid of the V loop. One or more or all amino acid of the V-loop may be replaced by the inserted target specific binding domain and/or the non-adenoviral polypeptide.

It has been set out above that the part of the penton base protomer specifically binding to STICKER is a non-contiguous epitope. Thus, preferably one or more of the following non-contiguous peptides within the penton base protomer form the adenovirus fibre protein binding cleft (bold amino acids interact directly with fibre)

$M-T-I-D-L-M-N-A-I-X_{40}-X_{41}-X_{42}-Y-\mathbf{L}-X_{43}-X_{44}-G-\mathbf{R}-Q-X_{45}-G-V-L-\mathbf{E}-S;$ (SEQ ID NO: 20)

$W-\mathbf{D}-P-X_{46}-T-X_{47}-\mathbf{X_{48}}-\mathbf{P}-G;$ (SEQ ID NO: 46)

$X_{49}-V-X_{50}-X_{51}-\mathbf{Y}-X_{52}-X_{53};$ (SEQ ID NO: 47)

$X_{54}-\mathbf{X_{55}}-R-S-Y;$ (SEQ ID NO: 48)

and/or $L-T-X_{56}-V-F-N-R-\mathbf{F}-P-X_{57}$ (SEQ ID NO: 49)

wherein $X_{40}$ is selected from the group consisting of V, I, and L;

$X_{41}$ is selected from the group consisting of E, and D;

$X_{42}$ is selected from the group consisting of H, N and Q, preferably H, and N;

$X_{43}$ is selected from the group consisting of K, E, R, Q, and A;

$X_{44}$ is selected from the group consisting of V, L, and I, preferably V, and I;

$X_{45}$ is selected from the group consisting of H, N and Q, preferably H, and N;

$X_{46}$ is selected from the group consisting of V, I, L, E, or D, preferably V, and E;

$X_{47}$ is selected from the group consisting of V, L, and I, preferably V, and I;

$X_{48}$ is selected from the group consisting of M, T and S, preferably M and T;

$X_{49}$ is selected from the group consisting of D, E, N, and Q, preferably D and N;

$X_{50}$ is any amino acid, preferably selected from the group consisting of A, D, P, K and T;

$X_{51}$ is selected from the group consisting of A, D, E, K and R, preferably A, E, and K;

$X_{52}$ is selected from the group consisting of D, E, L, I, Q, and N, preferably, E, L, and Q;

$X_{53}$ is selected from the group consisting of A, D, E, K, N, Q, and R, preferably A, E, N and K;

$X_{54}$ is selected from the group consisting of K, R, S, and T, preferably K, S and T;

$X_{55}$ is selected from the group consisting of A, D, E, G, K, N, Q, R, S, and T, preferably D, G, K, N, and S;

$X_{56}$ is selected from the group consisting of H, K, and R, preferably H and R; and $X_{57}$ is selected from the group consisting of D and E.

In a preferred embodiment of the engineered polypeptide of the invention of each other the amino acid sequence of $X_3$ to $X_{10}$ is independently selected from the group consisting of DVTAYEES (SEQ ID NO: 21), DVDAYENS (SEQ ID NO: 22), DVAEYEKS (SEQ ID NO: 23), DVEAYEKS (SEQ ID NO: 24), DVDAYEKS (SEQ ID NO: 25), DVSKYEAS (SEQ ID NO: 26), NVKAYEDS (SEQ ID NO: 27), DVKKYENS (SEQ ID NO: 28), DVDAYQAS (SEQ ID NO: 29), and DVDAYQAS (SEQ ID NO: 30), the amino acid sequence of $X_{18}$ to $X_{24}$ is selected from the group consisting of IQPLEKD (SEQ ID NO: 31), IQPVEKD (SEQ ID NO: 32), IKPLEKD (SEQ ID NO: 33), IVPLTKD (SEQ ID NO: 34), IEPVETD (SEQ ID NO: 35) and IKPLTED (SEQ ID NO: 36), the amino acid sequence of $X_{25}$ to $X_{31}$ is selected from the group consisting of FKARVMV (SEQ ID NO: 37), FRAKLMV (SEQ ID NO: 38), and FRAKVMV (SEQ ID NO: 39), the amino acid sequence of $X_{33}$ to $X_{39}$ is selected from the group consisting of YEWFEF (SEQ ID NO: 40), YEWVEF (SEQ ID NO: 41), and YEWAEF (SEQ ID NO: 42).

It has been surprisingly found that large heterologous polypeptides can be inserted and or replace the first and/or second RGD loop without disrupting assembly of penton and subsequently the VLPs of the invention.

In a preferred embodiment of the engineered polypeptide of the invention each of the target specific binding domain of the first RGD loop independently of each other has a length of between 5 to 300 amino acids, preferably between 6 to 200 amino acids; the target specific binding domain of the second RGD loop has a length of between 5 to 300 amino acids, preferably between 10 to 200 amino acid; and/or the target specific binding domain in the V loop has a length of between 5 to 300 amino acids, preferably between 10 to 200 amino acid.

In one alternative the target bound by the target specific binding domain is a moiety present on the surface of a cell or in the extracellular matrix. The specificity of the target specific binding domain is chosen, if the VLPs are targeted to a specific cell type in order to deliver its payload, e.g. drug or label. In an alternative preferred embodiment of the engineered polypeptide of the invention the at least one target specific binding domain is capable of specifically binding to an immunogenic peptide, pathogen neutralizing peptide, viral peptide, bacterial peptide, immune-modulating peptide, cancer peptide, to the surface of a cell, preferably a cellular receptor, a low molecular weight tag, preferably biotin or chitin. This provides an alternative and rapid way of binding various peptides to the surface of the VLPs.

In a preferred embodiment of the engineered polypeptide of the first or second aspect of the invention the non-adenoviral polypeptide or the polypeptide inserted or attached is selected from the group consisting of immunogenic peptides, pathogen neutralizing peptides, viral peptides, bacterial peptides, immune-modulating peptides, and cancer peptides. Particularly preferred are viral peptides of Dengue HAKKQDVVVLGSQEGAM (SEQ ID NO: 55), Chikungunya STKDNFNVYKATRPYLAH (SEQ ID NO: 56) and of Zika virus STKDNFNVYKATRPLAH (SEQ ID NO: 57). Examples of the engineered polypeptide of the second aspect of the invention comprising STICKER and a Chikungunya peptide are AKRARLST-SFNPVPYEDESSTKDNFNVYKATRPYLAH (SEQ ID NO: 58), AKRARLSTSFNPVPYEDECSSTKDNFN-VYKATRPYLAH (SEQ ID NO: 59) and AKRARL-STCFNPVPYEDESSTKDNFNVYKATRPYLAH (SEQ ID NO: 60). The latter two examples comprise a coupling residue, i.e. Cys to form a covalent bond to a corresponding coupling residue in the binding cleft for fibre of the penton base protomer.

Preferred examples of target specific binding domains are antibodies, single chain antibodies, antibody fragments, nanobodies, light or heavy chains, variable light or variable heavy chains, diabodies, or antibody mimetics. Preferred antibody fragments comprise a fragment antigen binding (Fab) fragment, a Fab' fragment, a F(ab')$_2$ fragment, a heavy chain antibody, a single-domain antibody (sdAb), a single-chain fragment variable (scFv), a fragment variable (Fv), a $V_H$ domain, a $V_L$ domain, a single domain antibody, a nanobody, an IgNAR (immunoglobulin new antigen receptor), a di-scFv, a bispecific T-cell engager (BITEs), a dual affinity re-targeting (DART) molecule, a triple body, a diabody, a single-chain diabody, an alternative scaffold protein, and a fusion protein thereof.

If a non-adenoviral peptide or the peptide is inserted into the first RGD loop they preferably have a length of between 5 to 60 amino acids, preferably of between 6 to 45 amino acids. If the non-adenoviral peptide or the peptide is inserted into the second RGD loop they can have a length of between 5 to 50 amino acids, preferably between 10 to 36 amino acids. If the non-adenoviral peptide or the peptide is inserted into the second V loop they can have a length of between 5 to 30 amino acids, preferably between 10 to 21 amino acids.

In a preferred embodiment of the engineered polypeptide of the first or second aspect invention the non-adenoviral polypeptide or the polypeptide comprises a protease cleavage site, preferably a sequence specific endopeptidase cleavage site, more preferably a TEV cleavage site. A preferred example of such a TEV cleavage site is ENLYFQG (SEQ ID NO: 60). Such a cleavage site allows cleavage of the polypeptide of the first aspect of the invention once assembled into penton or VLP. Some antigens require exposure of the free N- and/or C-terminus to elicit an immune response. Thus, if penton proteins or VLPs have been assembled treatment of those with a protease will expose the N- and/or C-terminal sequence of such antigens, if the cleavage site is positioned at the N- and/or C-terminal end of such a non-adenoviral polypeptide. Quite surprisingly the present inventors have found such cleavage does not disrupt the assembled penton or VLP. This is extremely useful in situations in which the a strong antigen specific immune response requires the exposure of free N- and/or C-terminii of the antigen. Alternatively, the cleavage sit can be comprised in an engineered polypeptide of the first and/or second aspect of the invention to facilitate purification of the engineered polypeptide, e.g. it can be placed at the N- or C-terminus of the respective engineered polypeptide separating the penton or fibre comprising part of the engineered polypeptide from an affinity tag, e.g. biotin, chitin binding protein, Myc-taq. Such an affinity tag allows immobilization of the engineered polypeptide on a suitable affinity matrix and release of purified engineered polypeptide from the matrix.

In a preferred embodiment of the engineered polypeptide of the first or second aspect of the invention the coupling residue is selected from the group comprising Lys, Cys, Asp, and Glu, preferably Cys.

In a preferred embodiment of the engineered polypeptide of the first or second aspect of the invention the drug is selected from the group of chemotherapeutic drug, antipathogenic drug, immune modulating drug, and anti-inflammatory drug.

In a preferred embodiment of the engineered polypeptide of the second aspect of the invention the fibre protein fragment comprises, consists essentially of or consists of:

$$X_{58}\text{-F-N-P-V-Y-P-Y-}X_{59} \quad (\text{SEQ ID NO: 43})$$

wherein $X_{58}$ is selected from the group consisting of S, D and T, preferably S or D, and is more preferably S; and $X_{59}$ is selected from the group consisting of E, D and G, is preferably E or D, and is more preferably E.

Preferably, the fibre protein fragment has a length between 9 to 20 contiguous amino acids of fibre.

It is further preferred that the engineered polypeptide of the second aspect of the invention comprises 2, 3, 4, 5, 6, 7, or 8 repeats of the fragment of the fibre protein. The multimerization increases binding affinity. It has been observed by the present inventors that 2 or 3, preferably consecutive repeats are suitable to mediate binding to the fibre binding cleft on the penton base protomer with sub-nanomolar affinities. Preferably, the multimers are arranged in a head-to-tail orientation.

As has been set out above, it is preferred according to alternative embodiment (vi) that one or more coupling residues are comprised in the binding cleft of the penton base protomer. To facilitate formation of covalent bonds between these one or more coupling residues in the penton base protomer and coupling residues comprised in the engineered polypeptide of the second aspect of the invention. In a preferred embodiment of the engineered polypeptide of the second aspect of the invention the at least one coupling residue is inserted into and/or positioned at the N- and/or C-terminus of the fibre protein fragment, preferably inserted into and/or positioned at the N- and/or C-terminus of SEQ ID NO: 43 or attached to an amino acid of the fibre protein fragment. As has been set out above coupling residues have to form covalent bonds with corresponding coupling residues. Once two polypeptides interact it is preferred that the coupling residue of the one polypeptide is sterically close to the coupling residue in the other polypeptide.

In a preferred embodiment of alternative embodiment (vi) the coupling residue is positioned in the penton base protomer comprised in the engineered polypeptide of the first aspect of the invention at amino acid position 476 and/or 477 (with reference to the amino acid sequence of SEQ ID NO: 64) or at an analogous amino acid position of a penton base protomer of another adenovirus. The analogous position in another adenovirus penton base protomer can be determined by aligning the sequence according to SEQ ID NO: 64 with other adenoviral penton base protomer sequences with a standard alignment tool, like, e.g. CLUSTAL. The skilled person can easily determine the amino acid that occupies an analogous position to amino acids 476 or 477 in another adenovirus penton protein. It is preferred that the engineered protein according to the first aspect of the invention and according to alternative embodiment (iv) comprises the sequence $$\text{KSFX}_{64}\text{NX}_{c1}\text{X}_{c2}\text{AVY} \quad \text{(SEQ ID NO: 68)}$$

wherein
$X_{64}$ is selected from the group consisting of Y and F, preferably Y;
$X_{c1}$ is selected from the group consisting of D, E and a coupling residue, preferably Cys;
$X_{c2}$ is selected from the group consisting of L, Q and a coupling residue, preferably Cys; and wherein at least one, preferably both $X_{c1}$ and $X_{c2}$ are a coupling residue, preferably Cys.

If the coupling residue in the penton base protomer is positioned at either amino acid position 476 and/or 477 or at an analogous amino acid position of a penton base protomer of another adenovirus than it is preferred that a corresponding coupling reside of the engineered polypeptide of the second aspect of the invention comprises a coupling residue at the C-terminus of the STICKER part of the polypeptide. It is preferred that the coupling residue is located in STICKER as shown in below sequence:

$$X_{58}\text{-F-N-P-V-Y-P-Y-}X_{59}\text{-}(X_{63})_n\text{-}X_c \quad \text{(SEQ ID NO: 69)}$$

wherein
$X_{58}$ is selected from the group consisting of S, D and T, preferably S or D, and is more preferably S; and
$X_{59}$ is selected from the group consisting of E, D and G, is preferably E or D, and is more preferably E;
$X_{63}$ is in each case independently any amino acid, preferably those naturally occurring in fibre proteins at this or these positions;
$X_c$ is a coupling residue, preferably C, D, E, and K, most preferably C; and
n is an integer between 0 to 10, i.e. 0, 1, 2, 3, 4, 5, 6, 7, 8, 9, or 10, preferably between 1 and 5, more preferably 2.

Thus, the engineered protein of the second aspect of the invention comprises in a preferred embodiment a STICKER polypeptide according to SEQ ID NO: 69. A particularly preferred STICKER polypeptide that may be comprised in the engineered protein of the second aspect of the invention is $$\text{A-K-R-A-R-L-S-T-}X_{58}\text{-F-N-P-V-Y-P-Y-}X_{59}\text{-D-E-}X_c \quad \text{(SEQ ID NO: 76)}$$

wherein
$X_{58}$ is selected from the group consisting of S, D and T, preferably S or D, and is more preferably S;
$X_{59}$ is selected from the group consisting of E, D and G, is preferably E or D, and is more preferably E; and
$X_c$ is a coupling residue, preferably C, D, E, and K, most preferably C.

In a particularly preferred embodiment the STICKER polypeptide comprises the coupling residue Cys at position 20 and consists of the following amino acid sequence:

$$\text{A-K-R-A-R-L-S-T-S-F-N-P-V-Y-P-Y-E-D-E-C} \quad \text{(SEQ ID NO: 77)}$$

In an alternative preferred embodiment of alternative embodiment (vi) the coupling residue is positioned in the penton base protomer comprised in the engineered polypeptide of the first aspect of the invention at Lys376 of the penton base protomer according to SEQ ID NO: 64 or an analogous position of a penton base protomer of another adenovirus. The engineered protein of the first aspect preferably comprises the following sequence:

$$X_c\text{-}X_{65}\text{-R-S-Y-N} \quad \text{(SEQ ID NO: 73)}$$

wherein
$X_c$ is a coupling residue, preferably C, D, E, and K, most preferably C; and
$X_{65}$ is any amino acid, is preferably selected from the group consisting of D, E, G, K, N, or S, more preferably S or N.

If the coupling residue is comprised at this position it is preferred that the engineered polypeptide of the second aspect of the present invention comprises a corresponding coupling residue as indicated in below amino acid sequence:

$$X_c\text{-F-N-P-V-Y-P-Y-}X_{59} \quad \text{(SEQ ID NO: 70)}$$

wherein
$X_{59}$ is selected from the group consisting of E, D and G, is preferably E or D, and is more preferably E; and/or
$X_c$ is a coupling residue preferably C, D, E, and K, most preferably C.

Accordingly, the engineered protein of the second aspect of the invention comprises in a preferred embodiment a STICKER polypeptide according to SEQ ID NO: 70. A particularly preferred STICKER polypeptide that may be comprised in the engineered protein of the second aspect of the invention is $$\text{A-K-R-A-R-L-S-T-}X_c\text{-F-N-P-V-Y-P-Y-}X_{59}\text{-D-E-S} \quad \text{(SEQ ID NO: 74)}$$

wherein
$X_c$ is a coupling residue, preferably C, D, E, and K, most preferably C; and
$X_{59}$ is selected from the group consisting of E, D and G, is preferably E or D, and is more preferably E.

In a particularly preferred embodiment the STICKER polypeptide comprises the coupling residue Cys at position 9 and consists of the following amino acid sequence:

$$\text{A-K-R-A-R-L-S-T-C-F-N-P-V-Y-P-Y-E-D-E-S} \quad \text{(SEQ ID NO: 75)}$$

In some embodiments of the engineered polypeptide of the first-aspect of the invention it is desired that the RGD motif positioned between the first and second RGD loop is intact to facilitate binding of the penton base protomer, penton or the VLP to certain cellular and extracellular structures present in a patient. Alternatively, if such targeting is not desired in a particular application of the engineered polypeptide of the first aspect of the invention, the RGD motif may be mutated in such that it loses its ability to bind to integrin.

In a third aspect the present invention relates to a nucleic acid encoding the engineered polypeptide of the first aspect of the invention and/or the engineered polypeptide of the second aspect of the invention.

In a fourth aspect the present invention relates to an expression vector comprising the nucleic acid of the invention. Expression vectors comprise plasmids as well as viral vectors and contain a coding sequence encoding the engineered protein of the first and/or second aspect of the invention and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

It has been realized in the art that immunization against diseases that rapidly change their antigenic epitopes, e.g. influenza, or that are characterized by a patient specific epitope mixture require rapid adaption or individualization of the vaccine. The VLPs of the present invention can be rapidly adapted to present the respectively desired antigens. Accordingly, the present invention relates in a fifth aspect to a cloning vector amenable to rapid insertion of nucleic acid segments into the first and/or second RGD-loop or V-loop, which encode one or more desired antigen. The cloning vector of this aspect of the invention comprises:

(i) a polypeptide comprising an adenovirus penton base protomer, wherein said penton base protomer comprises a first RGD-loop, a second RGD-loop, a variable loop and/or a binding site for adenovirus fibre protein adapted for introducing nucleic acids encoding non-adenoviral peptides into the nucleic acids encoding the first RGD-loop, the second RGD-loop and/or the variable loop; or (ii) polypeptide comprising an adenovirus penton base protomer binding fibre protein fragment adapted for introducing nucleic acids encoding non-adenoviral peptides a the C- and/or N-terminus.

In a preferred embodiment cloning vector of the present invention the adaptation comprises one or more restriction enzyme sites, preferably BamHI, KpnI, KasI, NarI, SfdI, EcoRI and RsrII, PfoI, BssHII, SalI, SacI, XbaI, BstEII, and HindIII. The nucleic acid sequence of preferred examples of such a cloning vector is provided in SEQ ID NO: 61 and 62. The structure of these vectors termed pACEBac-ADDOmer1.0 and pACEBac-ADDOmer2.0 is provided in FIGS. 7 and 8. The sequence of the cloning vector pACEBac-ADDOmer2.0 comprising the preferred Chikungunya virus antigenic epitope is provided in SEQ ID NO: 71 and 72.

In a sixth aspect the present invention relates to a recombinant host cell comprising the expression vector of the present invention or the cloning vector of the present invention. The expression vector of the present invention or the cloning vector of the present invention may be found inside the host cell (i) freely dispersed as such, or (ii) integrated into the host cell genome or mitochondrial DNA. The recombinant host cell is used for expression of the engineered polypeptides of the invention. The term "recombinant host cell" includes the progeny of the original cell which has been transformed, transfected, or infected with the polynucleotide or the recombinant vector of the invention. A recombinant host cell may be a bacterial cell such as an *E. coli* cell, a yeast cell such as *Saccharomyces cerevisiae* or *Pichia pastoris*, a plant cell, an insect cell such as SF9 or Hi5 cells, or a mammalian cell. Preferred examples of mammalian cells are Chinese hamster ovary (CHO) cells, green African monkey kidney (COS) cells, human embryonic kidney (HEK293) cells, HELA cells, and the like.

The engineered polypeptides of the first aspect of the present invention are capable in spite of their modification according to alternative embodiments (i) to (vi) in comparison to the respective wild-type penton base protomers to assembe into a penton subunit, i.e. to form a pentamer. Whether a given engineered protein of the first aspect of the invention assembles into pentamers can be easily assessed by methods well known to the skilled person that comprise non-denaturing polyacrylamide gel electrophoresis, size exclusion chromatography, mass spectroscopy or the like. Thus, in a seventh aspect the present invention relates to a pentamer comprising five engineered polypeptides comprising adenovirus penton base protomer of the invention. This pentamer may additionally comprise between 1 and engineered polypeptides of the second aspect of the present invention.

The pentamers assembled from the engineered polypeptides of the first aspect of the present invention are further capable of assembly into a VLP. Accordingly, in an eight aspect the present invention relates to a virus-like particle (VLP) comprising 12 pentamers of the present invention. The VLP is stable and the most suitable composition for administration to a patient. Preferably, the VLP is assembled and/or stored under non-reducing conditions to allow the formation of covalent bonds between coupling residues in the penton base protomers.

In a preferred embodiment the VLP of the present invention further comprises at least one engineered polypeptide of the second aspect of the invention, preferably up to 60 engineered polypeptide of the second aspect of the invention. In the latter embodiment all fibre protein binding clefts of the penton base proteins of the engineered polypeptide of the first aspect of the invention are occupied by engineered proteins of the second aspect of the invention. It is preferred that the VLPs of the present invention comprise an engineered protein of the first aspect of the invention comprising the modification according to alternative (vi), preferably combined with a modification according to alternative (i), (ii), (iii), (iv), and/or (v) and an engineered protein of the second aspect of the invention comprising at least one coupling residue, preferably the at least one coupling residue in inserted into and/or positioned at the N- and/or C-terminus of the fibre protein fragment, preferably inserted into and/or positioned at the N- and/or C-terminus of SEQ ID NO: 43 or attached to an amino acid of the fibre protein fragment. Preferably, the engineered protein of the first aspect of the invention comprises KSF$X_{64}$N$X_{c1}$$X_{c2}$AVY (SEQ ID NO: 68), wherein $X_{64}$, $X_{c1}$, and $X_{c2}$ have the meaning outlined above and the engineered protein of the second aspect of the invention comprises $X_{58}$-F-N-P-V-Y-P-Y-$X_{59}$-$(X_{63})_n$-$X_c$ (SEQ ID NO: 69), wherein $X_{58}$, $X_{59}$, $X_{63}$, $X_c$, and n have the meaning outlined above. In an alternative preferred embodiment the engineered protein of the first aspect of the invention comprises the following sequence $X_c$-$X_{65}$-R-S-Y-N (SEQ ID NO: 73), wherein $X_c$ and $X_{65}$ have the meaning outlined above and the engineered protein of the second aspect of the invention comprises $X_c$-F-N-P-V-Y-P-Y-$X_{59}$ (SEQ ID NO: 70), wherein $X_c$ and $X_{59}$ have the meaning outlined above.

Preferably, the VLPs which comprise coupling residues to covalently couple the engineered polypeptide of the first aspect of the invention to the engineered polypeptide second present invention is assembled and/or stored under non-reducing conditions to allow the formation of covalent bonds between coupling residues in the penton base protomers and the STICKER polypeptide comprised in the engineered polypeptide of the second aspect of the invention.

It is also envisioned that VLPs consisting of or comprising wild-type penton base protomers are used to provide a vehicle and that these are decorated with different non-adenoviral polypeptides by using the engineered polypeptide of the second aspect of the invention. Due to the short length that the engineered polypeptide of the second aspect of the invention has in preferred embodiments, it can be synthesized, e.g. by solid state chemistry within less than a day. Thus, in a ninth aspect the present invention relates to a VLP comprising 12 pentamers each comprising five adenovirus penton base protomers and at least one engineered polypeptide of the second aspect of the invention. It is preferred that all fibre protein binding clefts of the penton base protomers are occupied and, thus that these VLPs comprise 60 engineered polypeptides of the second aspect of the invention.

In a tenth aspect the present invention relates to a method for producing an engineered polypeptide of the first or second aspect of the present invention, comprising the steps of:
(a) providing a recombinant host cell of the present invention;
(b) expressing the engineered polypeptide; and
(c) purifying the engineered polypeptide.

In an eleventh aspect the method for producing a VLP of the invention comprising the steps of the method of the tenth aspect of the invention and the further step of allowing the engineered polypeptides to assemble into a VLP.

The method of the tenth aspect of the present invention further comprising the step of incubating the VLP with a protease, preferably a sequence specific endopeptidase cleavage site, more preferably TEV.

In a twelfth aspect the present invention relates to a method for producing a VLP of the invention comprising disease and/or patient specific non-adenoviral peptides, comprising the steps of:
(a) providing a cloning vector of the invention;
(b) determining the amino acid sequence of disease or patient specific non-adenoviral peptides;
(c) inserting nucleic acids encoding at least one of said non-adenoviral peptides into nucleic acids encoding the first RGD-loop, the second RGD-loop and/or the variable loop of the adenovirus penton base protomer, and/or at nucleic acid position preceding or subsequent to nucleic acids encoding the N- or C-terminus of the engineered polypeptide comprising an adenovirus penton base protomer binding fibre protein fragment;
(d) expressing the engineered adenovirus penton base protomer in a host cell, optionally together with the engineered polypeptide comprising an adenovirus penton base protomer binding fibre protein fragment; and
(e) purifying said VLP optionally comprising an adenovirus penton base protomer binding fibre protein fragment, or said engineered polypeptide comprising an adenovirus penton base protomer binding fibre protein fragment.

In a thirteenth aspect the present invention relates to a method for producing a VLP of the invention comprising disease and/or patient specific non-adenoviral peptides, comprising the steps of:
(a) providing a cloning vector of the invention;
(b) determining the amino acid sequence of disease or patient specific non-adenoviral peptides;
(c) inserting nucleic acids encoding at least one of said non-adenoviral peptides at nucleic acid position preceding or subsequent to nucleic acids encoding the N- or C-terminus of the engineered polypeptide comprising an adenovirus penton base protomer binding fibre protein fragment;
(d) expressing the engineered polypeptide comprising an adenovirus penton base protomer binding fibre protein fragment in a host cell, optionally together with an adenovirus penton base protomer; and
(e1) purifying said engineered polypeptide comprising an adenovirus penton base protomer binding fibre protein fragment and admixing with adenovirus penton base protomers or engineered adenovirus penton base protomers of the invention; or
(e2) purifying said VLP in case that the adenovirus penton base protomer was co-expressed.

In a fourteenth aspect the present invention relates to a method for producing a VLP of the invention comprising disease and/or patient specific non-adenoviral peptides, comprising the steps of:
(a) determining the amino acid sequence of disease or patient specific non-adenoviral peptides;
(b) synthesizing an engineered polypeptide of the invention comprising an adenovirus penton base protomer binding fibre protein fragment and at least one of said non-adenoviral peptides; and
(c) admixing said engineered polypeptide with adenovirus penton base protomers or engineered adenovirus penton base protomers of the invention with pentamers of the invention or with VLPs of the invention.

In a fifteenth aspect the present invention relates to a VLP producible by a method of producing a VLP of the invention.

In a sixteenth aspect the present invention relates to a pharmaceutical composition comprising the engineered polypeptide comprising an adenovirus penton base protomer of the invention and/or engineered polypeptide comprising an adenovirus penton base protomer binding fibre protein fragment of the invention, the nucleic acid encoding one or more of the engineered proteins of the invention, the expression vector of the invention or the VLP of the invention, and a pharmaceutically acceptable carrier and/or suitable excipient(s). Preferably, such composition is a pharmaceutical composition. In preferred embodiments the pharmaceutical composition further comprises a pharmaceutically acceptable carrier and/or excipient and optionally one or more additional active substances. Preferably, the composition of the fifth aspect contains a therapeutically effective amount of the compound, preferably in purified form, together with a suitable amount of carrier and/or excipient so as to provide the form for proper administration to the patient. The formulation should suit the mode of administration.

The pharmaceutical compositions can take the form of solutions, suspensions, emulsion, tablets, pills, capsules, powders, sustained-release formulations and the like. The pharmaceutical composition can be formulated as a suppository, with traditional binders and carriers such as triglycerides.

For preparing pharmaceutical compositions of the present invention, pharmaceutically acceptable carriers can be either solid or liquid. Solid form compositions include powders, tablets, pills, capsules, lozenges, cachets, suppositories, and dispersible granules. A solid excipient can be one or more substances, which may also act as diluents, flavouring agents, binders, preservatives, tablet disintegrating agents, or an encapsulating material. In powders, the excipient is preferably a finely divided solid, which is in a mixture with the finely divided inhibitor of the present invention. In tablets, the active ingredient is mixed with the carrier having the necessary binding properties in suitable proportions and compacted in the shape and size desired. Suitable excipients are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. For preparing suppositories, a low melting wax, such as a mixture of fatty acid glycerides or cocoa butter, is first melted and the active component is dispersed homogeneously therein, as by stirring. The molten homogeneous mixture is then poured into convenient sized moulds, allowed to cool, and thereby to solidify. Tablets, powders, capsules, pills, cachets, and lozenges can be used as solid dosage forms suitable for oral administration.

Liquid form compositions include solutions, suspensions, and emulsions, for example, water, saline solutions, aqueous dextrose, glycerol solutions or water/propylene glycol solutions. For parenteral injections (e.g. intravenous, intraarterial, intraosseous infusion, intramuscular, subcutaneous, intraperitoneal, intradermal, and intrathecal injections), liquid preparations can be formulated in solution in, e.g. aqueous polyethylene glycol solution. A saline solution is a preferred carrier when the pharmaceutical composition is administered intravenously.

Preferably, the pharmaceutical composition is in unit dosage form. In such form the composition may be subdivided into unit doses containing appropriate quantities of the active component. The unit dosage form can be a packaged composition, the package containing discrete quantities of the composition, such as packaged tablets, capsules, and powders in vials or ampoules. Also, the unit dosage form can be a capsule, an injection vial, a tablet, a cachet, or a lozenge itself, or it can be the appropriate number of any of these in packaged form.

The composition, if desired, can also contain minor amounts of wetting or emulsifying agents, or pH buffering agents.

Furthermore, such pharmaceutical composition may also comprise other pharmacologically active substance such as but not limited to adjuvants and/or additional active ingredients. Adjuvants in the context of the present invention include but are not limited to inorganic adjuvants, organic adjuvants, oil-based adjuvants, cytokines, particulate adjuvants, virosomes, bacterial adjuvants, synthetic adjuvants, or synthetic polynucleotides adjuvants.

In a seventeenth aspect the present invention relates to an engineered polypeptide comprising an adenovirus penton base protomer of the invention and/or engineered polypeptide of the invention comprising an adenovirus penton base protomer binding fibre protein fragment, the nucleic acid encoding one or more of the engineered proteins of the invention, the expression vector of the invention or the VLP of the invention for treating and/or preventing an infectious disease, an immune disease or cancer.

EXAMPLES

ADDomers were designed and produced in very high yields (tens of grams per liter expression culture). A generic three-step protocol was established to purify ADDomer to homogeneity (see below). In a proof-of-concept project, it was experimentally established that highly immunogenic Chikungunya epitopes can be inserted into the functionalized loops of ADDomer, without perturbing particle formation or decreasing yield noticeably. ADDomers containing Chikungunya epitopes were purified to homogeneity and cell-based and animal studies were initiated to establish their potency as vaccine candidates. The ADDomers were validated with a range of techniques including electron microscopy, evidencing homogenously structured, discrete multimers (dodecahedra). Cysteine-disulfide chemistry was implemented to even further increase the already remarkable thermostability of ADDomer (elimination of cold chain requirement). Moreover, ADDomers were preparaed which contain not only peptide epitopes but also protein domains and entire proteins including high-affiny binders (nanobodies DARPins, antibody fragments) and are establishing efficient protocols to manufacture these in large scale. Triggered by the recent emergence of Zika virus, ADDomer-based Zika vaccine candidates were designed, and also ADDomers to potentially combat more than one disease simultaneously (combo vaccine). Cell-based and animal experiments to validate these are performed.

In the following, experiments and protocols are described to produce and validate ADDomer VLPs and ADDomer VLP vaccines.

1. ADDomer Design

The atomic structure of naturally occurring dodecamer species (e.g. derived from Adenovirus Ad3 serotype) has been determined by X-ray crystallography (Szolajska E et al., PLoS One. 2012; 7(9):e46075 and Zubieta C et al., Mol. Cell 2005: 17(1):121-35). Careful inspection of the atomic structures revealed the presence of extended loop structures. More precisely, one variable loop (denominated V-loop) and two regions in the so-called RGD-loop of the wild-type dodecahedron were indentified as potential sites of functionalization. Comparison of a number of dodecahedron protomers revealed a wide variability of the V-loop and the two RGD-loop regions throughout the species, both in length and in sequence composition, underscoring their potential. Using this information, we designed de novo a DNA sequence encoding for a synthetic designer dodecahedron promoter. BioBrick design (Shetty et al. J. Biol. End. 2008) was applied by introducing DNA sequences representing endo-nuclease cleavage sites, to facilitate designed variations (and even randomization) of the amino acids representing the V-loop and the two RGD-loop regions (RGD-loop2, RGDloop2). The protomer design was optimized iteratively until a protomer was identified that would give rise to recombinant dodecahedra (ADDomer) characterized by complete BioBrick design of the above described loop regions, while maintaining the high solubility and structure integrity of wild-type human Ad3 serotype dodecahedron.

2. Engineering Hyperstable ADDomer

ADDomer is already remarkably thermostable and can be stored at 37° C. for protracted times, indicative of not requiring a cold-chain in remote areas with poor infrastructure. Inspection of the crystal coordinates of native Ad3 particles revealed a so-called 'strand-swapping' region, where segments of the protomers extended to the vicinity of the adjacent protomers resulting in juxtaposition of amino acids that were within a distance that could allow covalent bond formation. We genetically substituted these amino acids in ADDomer with cysteines, such that two cysteines each coming from distinct protomers were within the distance required for disulfide bond formation.

3. MultiBac-Based ADDomer Expression

Next, ADDomers were expressed by using the MultiBac system. The gene encoding for ADDomer was synthesized from scratch (SEQ ID NO: 63 and the encoded ADDomer is provided in SEQ ID NO: 64) and inserted by classical cloning methods (restriction/ligation) into pACEBac, a transfer plasmid of the MultiBac system. MultiBac was developed by one of the inventors (Berger) specifically for the production of complex biologics such as ADDomer. Composite MultiBac virus containing the ADDomer gene was prepared (see FIGS. 7 and 8) and insect cell cultures infected following previously described protocols (Berger I et al. J Vis Exp. (2013) (77):e50159 and Fitzgerald D J et al. Nat Methods. (2006) 3(12):1021). ADDomer protein-containing cell pellets were prepared by centrifugation as described. Cell pellets were stored at −80 degrees. Expression of ADDomer with peptide or protein epitopes inserted, and also expression of hyperstable ADDomer, all gave rise to comparable, very high yields and homogeneously structured dodecahedral particles.

3. Neutralizing Epitope

Figure 14:
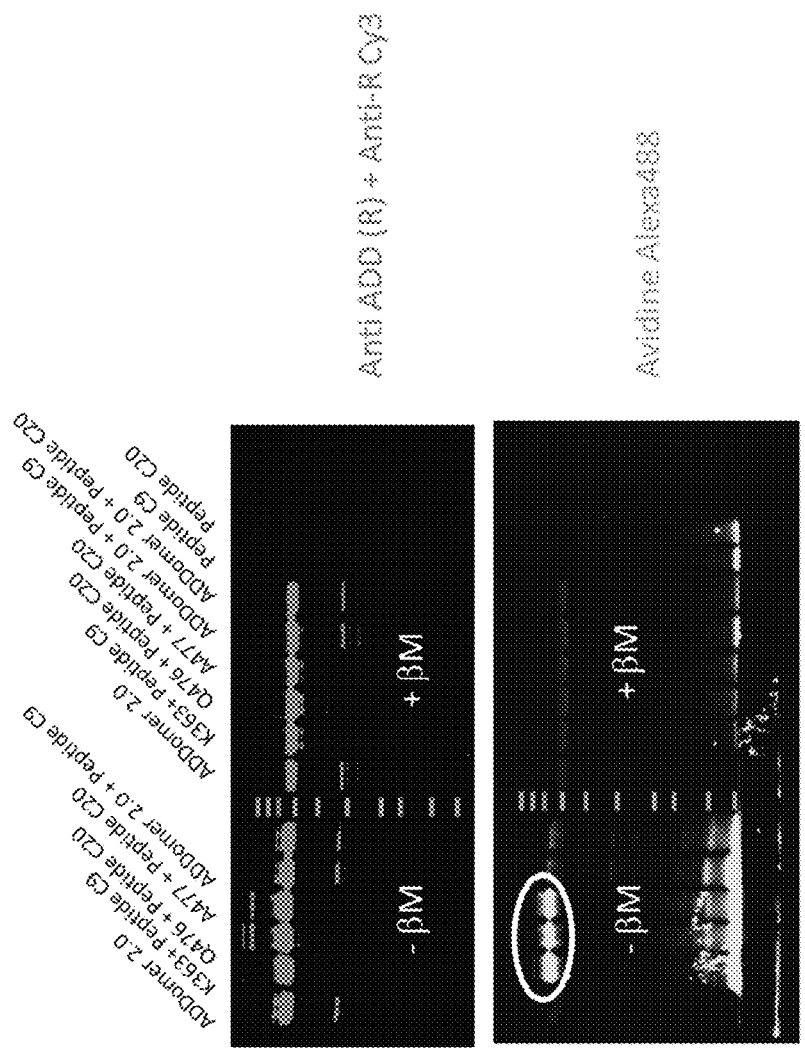

Example ADDomer-CHIKADDomer-based VLP vaccine candidate presenting multiple copies of the major neutralizing Chikungunya immune epitope HAKKQDVVVLGSQEGAM (SEQ ID NO: 55) were constructed. The major neutralizing immune epitope is part of a Chikungunya envelope protein, and is a linear peptide epitope located at the extreme N-terminus (Kam Y W et al. EMBO Mol Med. (2012); 4(4):330-4). In an overwhelming majority of patient sera, antibodies are found which react with this linear peptide epitope. ADDomer provides the means to present linear epitopes either in a constrained fashion (bot N- and C-termini covalently linked to ADDomer scaffold), or in an uncontrained fashion (N-termini liberated by cleavage with a specific protease) or a combination of constrained or unconstrained epitopes, all the while preserving structural integrity of the ADDomer scaffold. Preferred arrangements used were the following: AKRARLSTSFNPVPYEDESSTKDNFNVYKATRPYLAH (SEQ ID NO: 58), AKRARLSTSFNPVPYEDECSSTKDNFNVYKATRPYLAH (SEQ ID NO: 59) and AKRARLSTCFNPVPYEDESSTKDNFNVYKATRPYLAH (SEQ ID NO: 60). Nature-like presentation of the Chikungunya major neutralizing epitope was achieved by TEV protease-mediated cleavage of ADDomer presenting multiple copies of the epitope, each containing a specific TEV cleavage site preceding the neutralizing epitope sequence, preserving thye native N-terminus. Similar approaches can be used for any epitope or peptide or protein domain displayed by ADDomer.

4. Purification of ADDomer and Variants

Spodopterafrugiperda Sf21 insect cells pellets were lysed by freeze-thawing. Lysate was cleared by centrifugation following standard protocols for insect cells (Berger I et al. J Vis Exp. (2013) (77):e50159 and Fitzgerald D J et al. Nat Methods. 2006 3(12):1021). Cleared supernatant was loaded on a 15 to 40% sucrose gradient and centrifuged utilizing a Beckman SW41 rotor overnight. Fractions of 1.1 mL were collected from the top of the gradient and loaded on denaturing SDS polyacrylamide gels (SDS-PAGE) for analyzing protein content and identifying fractions containing ADDomers for pooling Size exclusion chromatography (SEC) and/or ion-exchange (IEX) was then carried out after dialyzing away the sucrose.

5. Validation of ADDomer by Electron Microscopy

Purified ADDomer and ADDomer variants were visualized by negative-stain electron microscopy (EM) to assess their assembly status and their structural integrity. Standard mica-carbon preparation was utilized with ADDomer at approximately 0.1 mg/ml concentration prior to deposition on the support material. Samples were stained using 1% (wt/vol) sodium silicotungstate (pH 7.0) and visualized on a JEOL electron microscope at 100 kV. Images were recorded and analysed was carried out using software supplied by Gatan.

For thermostability experiments, ADDomers were stored either frozen, at 4° C., at room temperature (RT) or at 37° C. for one week. Electron microscopy showed that storage at RT or at 37° C. resulted in correctly auto-assembled particles demonstrating their thermostability. Incubation of ADDomer (SEQ ID NO: 64) for 2H at 45° C. resulted in reversible particle disassembling which reassemble when turned back at RT. This reversible dissociation was also observed by Thermal Shift Assay (FIG. 10, see arrow) but irreversible dissociation was seen only for temperature above 50° C.

6. Design of Animal (Murine) Experiments to Assess ADDomer Immunogenicity

For murine immune analysis of ADDomer-CHIK Chikungunya ADDomer VLP vaccine candidates, six weeks old BALB/c female mice were used. Four groups of eight mice were designated per immunization with ADDomer species (e.g, in case of Chikungunya VLP vaccine candidate: i) ADDomer, ii) ADDomer CHIK unconstrained epitope, iii) ADDomer CHIK constrained epitope, iv) isolated CHIK major neutralizing peptide epitope cross-linked to KLH as positive control). Each animal was injected with 10 μg of ADDomer and ADDomer variants at 2 week intervals. IgA, IgM, total IgG, IgG1 IgG2a and anti-CHIK antibodies were titered from mouse sera by ELISA. Immune analysis of other ADDomer VLP vaccine candidates were designed in an analogous fashion. Two kind of epitope display at the ADDomer surface were tested (Constrained and Relaxed, see below: point 7). A time dependent response was observed (Week 0 to 6). The superior potential of the relaxed form of the epitope over the constrained form to trigger an anti-Chik epitope response was shown (FIG. 12).

7. Exposition of the Epitope of Interest at the ADDomer Surface

The addition of a TEV cleavage site upstream the epitope of interest enables its display under two different configurations: constrained or relaxed. Upon purification, the epitopes are naturally constrained in the ADDomer loops. By addition of the TEV (Tobacco Etch Virus) protease (1/100 w:w) for 2H at RT the epitope can be relaxed and displayed in a linear form at the scaffold surface. The cleavage efficiency is easily monitored by SDS-PAGE. Of note, the overall ADDomer scaffold is not affected by this cleavage (FIG. 11).

8. Extension of the Epitope Insertion Capacity in ADDomer

The capacity of ADDomer to carry large epitope sequence was assessed. To this end, a 200 amino acid in length artificial epitope was inserted in ADDomer (named extended ADDomer). This resulted in correctly auto-assembled ADDomer. The insertion was confirmed by both SDS-PAGE analysis and mass spectroscopy as shown in FIG. 13.

9. Covalent Linkage of Epitope at the ADDomer Surface

To widen the ADDomer potential, a system enabling the addition of extra epitopes at the ADDomer was developed. Single cysteines were inserted at specific locationd of the ADDomer sequence (either K363C or Q476C or A477C). K363C was designed to form covalent disulfide bridge with a fibre protein fragment of 20 amino acids length (peptide C20 (SEQ ID NO: 77) derived from SEQ ID NO: 59) while Q476C or A477C were designed to do the same with another fibre protein fragment (peptide C9 (SEQ ID NO: 75) derived from SEQ ID NO 60). The covalent interaction of the peptides with their corresponding Cys modified ADDomer was checked by incubating the particle with their corresponding peptide under oxidative condition (i.e. absence of beta-mercaptoethanol) or reducing condition (addition of beta-mercaptoethanol). Complexes were run on SDS-PAGE and ADDomer was detected by a specific antibody and a secondary antibody labelled with Cy3 while the biotinylated peptide was detected by Alexa488 labeled avidin. When the right Cys-ADDomer/peptide was used, the presence of peptide was detected at the ADDomer band size (circle in FIG. 14). This interaction was specific of the disulfide bridge created between the Cys-ADDomer and the peptide since the interaction was prevented under reducing conditions.

The present invention relates to the following aspects:

1. An engineered polypeptide comprising an adenovirus penton base protomer, wherein said penton base protomer comprises a first RGD-loop, a second RGD-loop, a variable loop (V loop), an adenovirus fibre protein binding cleft and/or a N-terminal domain, and comprises one or more of the following:
   (i) at least one target specific binding domain in the first, the second or both the first and the second RGD-loops, and/or in the V loop; and/or
   (ii) one or more non-adenoviral peptides in the first, the second or both the first and the second RGD-loops and/or in the V loop; and/or
   (iii) a non-adenoviral peptide at the N- and/or C-terminus of the penton base protomer; and/or
   (iv) at least one heterologous coupling residue in the first, the second, or both the first and the second RGD-loops, in the V loop and/or in the N-terminal domain of the penton base protomer, wherein the N-terminus of the N-terminal domain within the penton base protomer is defined as follows:

$$X_1\text{-}G\text{-}R\text{-}N\text{-}S\text{-}I\text{-}R \quad \text{(SEQ ID NO: 44)}$$

and the C-terminus of the N-terminal domain within the penton base protomer is defined as follows:

$$D\text{-}X_2\text{-}R\text{-}S\text{-}R\text{-}G, \quad \text{(SEQ ID NO: 45)}$$

wherein
   $X_1$ is selected from the group consisting of G and E, and
   $X_2$ is selected from the group consisting of D and E; and/or
   (v) a drug, label or polypeptide covalently or non-covalently coupled to one or more amino acids of the first, the second or both the first and the second RGD-loops and/or one or more amino acids of the V loop of the penton base protomer; and/or
   (vi) at least one heterologous coupling residue in the adenovirus fibre protein binding cleft of the penton base protomer and wherein the engineered polypeptide is preferably capable of assembling into VLPs.

2. An engineered polypeptide comprising at least one adenovirus fibre protein N-terminal fragment specifically binding to an adenovirus fibre protein binding cleft of a penton base protomer and:
   (i) a non-adenoviral peptide and/or
   (ii) is covalently or non-covalently coupled to a drug or label.

3. The engineered polypeptide according to item 1 or 2, wherein the adenovirus is a human or non-human great ape adenovirus, preferably Chimpanzee (Pan), Gorilla (Gorilla) and orangutans (Pongo), more preferably Bonobo (*Pan paniscus*) and common Chimpanzee (*Pan troglodytes*).

4. The engineered polypeptide according to item 3, wherein the adenovirus is selected from the group consisting of hAd3, hAd4, hAd5, hAd7, hAd11, hAd26, hAd35 and hAd49, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82, PanAd1, PanAd2, PanAd3, ChAd55, ChAd73, ChAd83, ChAd146, and ChAd147.

5. The engineered polypeptide according to item 1 or 3 or 4, wherein the sequence of the wild-type penton base protomer on which the engineered protein is based is selected from the group consisting of SEQ ID NO: 1 to 14.

6. The engineered polypeptide according to item 1 or 3 to 5, wherein the following sequence defines the N-terminus of the first RGD-loop within the penton base protomer:

$$X_3\text{-}X_4\text{-}X_5\text{-}X_6\text{-}X_7\text{-}X_8\text{-}X_9\text{-}X_{10}\text{-}X_{11} \quad \text{(SEQ ID NO: 15)}$$

wherein
$X_3$ is selected from the group consisting of D, E and N, and is preferably D;
$X_4$ is selected from the group consisting of V, L, and I, and is preferably V;
$X_5$ is any amino acid, is preferably selected from the group consisting of A, D, E, K, S, and T, and is more preferably T;
$X_6$ is any amino acid, is preferably selected from the group consisting of A, D, E, and K, and is more preferably A;
$X_7$ is selected from the group consisting of F, Y, and W, and is preferably Y;
$X_8$ is selected from the group consisting of A, D, E, N, and Q, is preferably E or Q, and is more preferably E;
$X_9$ is any amino acid, preferably selected from the group consisting of A, D, E, N, and K, and is more preferably E;
$X_{10}$ is selected from the group consisting of S or T, and is preferably S; and
$X_{11}$ is any amino acid and constitutes the N-terminal amino acid of the first RGD loop; and/or
the following sequence defines the C-terminus of the first RGD-loop and the N-terminus of the second RGD-loop within the penton base protomer:

$$X_{12}\text{-}X_{13}\text{-}X_{14}\text{-}X_{15}\text{-}X_{16} \quad \text{(SEQ ID NO: 16)}$$

wherein
$X_{12}$ is any amino acid and constitutes the C-terminal amino acid of the first RGD loop;
$X_{13}$ is R;
$X_{14}$ is G;
$X_{15}$ is D; and
$X_{16}$ is any amino acid and constitutes the N-terminal amino acid of the second RGD loop; and/or
the following sequence defines the C-terminus of the second RGD-loop within the penton base protomer:

$$X_{17}\text{-}X_{18}\text{-}X_{19}\text{-}X_{20}\text{-}X_{21}\text{-}X_{22}\text{-}X_{23}\text{-}X_{24};\quad \text{(SEQ ID NO: 17)}$$

wherein $X_{17}$ is any amino acid and constitutes the C-terminal amino acid of the second RGD loop;

$X_{18}$ is selected from the group consisting of I, L and V, and is preferably I;

$X_{19}$ is selected from the group consisting of D, E, K, N, Q, and V, is preferably Q or K, and is more preferably Q;

$X_{20}$ is selected from the group consisting of C, G and P, and is preferably P;

$X_{21}$ is selected from the group consisting of I, L and V, is preferably L or V and is more preferably L;

$X_{22}$ is selected from the group consisting of D, E, S and T, is preferably E or T and is more preferably E;

$X_{23}$ is selected from the group consisting of D, E, K, S and T, is preferably E, K or T, and is more preferably K; and $X_{24}$ is selected from the group consisting of D and E, and is preferably D; and/or the following sequence defines the N-terminus of the V loop:

$$X_{25}\text{-}X_{26}\text{-}X_{27}\text{-}X_{28}\text{-}X_{29}\text{-}X_{30}\text{-}X_{31}\text{-}X_{32}.\quad \text{(SEQ ID NO: 18)}$$

wherein $X_{25}$ is selected from the group consisting of F, Y, and W, and is preferably F;

$X_{26}$ is selected from the group consisting of H, K and R, and is preferably K;

$X_{27}$ is selected from the group consisting of A, V, I, and L, and is preferably A;

$X_{28}$ is selected from the group consisting of H, K and R, and is preferably R;

$X_{29}$ is selected from the group consisting of A, V, I, and L, and is preferably V;

$X_{30}$ is selected from the group consisting of A, V, I, L and M, and is preferably M;

$X_{31}$ is selected from the group consisting of A, V, I, and L, and is preferably V; and $X_{32}$ is any amino acid and constitutes the N-terminal amino acid of the V loop;

and/or the following sequence defines the C-terminus of the V loop $$X_{33}\text{-}X_{34}\text{-}X_{35}\text{-}X_{36}\text{-}X_{37}\text{-}X_{38}\text{-}X_{39}\quad \text{(SEQ ID NO: 19)}$$

wherein $X_{33}$ is any amino acid and constitutes the C-terminal amino acid of the V loop;

$X_{34}$ is selected from the group consisting of F, Y, and W, and is preferably Y;

$X_{35}$ is selected from the group consisting of D, E, S and T, is preferably E or T and is more preferably E;

$X_{36}$ is selected from the group consisting of F, Y, and W, and is preferably W;

$X_{37}$ is selected from the group consisting of A, F, V, Y, and W, is preferably F or V and is more preferably F;

$X_{38}$ is selected from the group consisting of D, E, S and T, is preferably D or E and is more preferably E; and $X_{39}$ is selected from the group consisting of F, Y, and W, and is preferably F;

and/or one or more of the following non-continuous peptides within the penton base protomer form the adenovirus fibre protein binding cleft (bold amino acids interact directly with fibre)

$$\text{M-T-I-D-L-M-N-N-A-I-}X_{40}\text{-}X_{41}\text{-}X_{42}\text{-Y-}\mathbf{L}\text{-}X_{43}\text{-}X_{44}\text{-G-}\mathbf{R}\text{-}$$
$$\text{Q-}X_{45}\text{-G-V-L-}\mathbf{E}\text{-S;}\quad \text{(SEQ ID NO: 20)}$$

$$\text{W-}\mathbf{D}\text{-P-}X_{46}\text{-T-}X_{47}\text{-}\mathbf{X_{48}}\text{-}\mathbf{P}\text{-G;}\quad \text{(SEQ ID NO: 46)}$$

$$X_{49}\text{-V-}X_{50}\text{-}X_{51}\text{-}\mathbf{Y}\text{-}X_{52}\text{-}X_{53};\quad \text{(SEQ ID NO: 47)}$$

$$X_{54}\text{-}\mathbf{X_{55}}\text{-R-5-Y;}\quad \text{(SEQ II NO: 48)}$$

and/or $$\text{L-T-}X_{56}\text{-V-F-N-R-}\mathbf{F}\text{-}\mathbf{P}\text{-}X_{57}\quad \text{(SEQ ID NO: 49)}$$

wherein $X_{40}$ is selected from the group consisting of V, I, and L;

$X_{41}$ is selected from the group consisting of E, and D;

$X_{42}$ is selected from the group consisting of H, N and Q, preferably H, and N;

$X_{43}$ is selected from the group consisting of K, E, R, Q, and A;

$X_{44}$ is selected from the group consisting of V, L, and I, preferably V, and I;

$X_{45}$ is selected from the group consisting of H, N and Q, preferably H, and N;

$X_{46}$ is selected from the group consisting of V, I, L, E, or D, preferably V, and E;

$X_{47}$ is selected from the group consisting of V, L, and I, preferably V, and I;

$X_{48}$ is selected from the group consisting of M, T and S, preferably M and T;

$X_{49}$ is selected from the group consisting of D, E, N, and Q, preferably D and N;

$X_{50}$ is any amino acid, preferably selected from the group consisting of A, D, P, K and T;

$X_{51}$ is selected from the group consisting of A, D, E, K and R, preferably A, E, and K;

$X_{52}$ is selected from the group consisting of D, E, L, I, Q, and N, preferably, E, L, and Q;

$X_{53}$ is selected from the group consisting of A, D, E, K, N, Q, and R, preferably A, E, N and K;

$X_{54}$ is selected from the group consisting of K, R, S, and T, preferably K, S and T;

$X_{55}$ is selected from the group consisting of A, D, E, G, K, N, Q, R, S, and T, preferably D, G, K, N, and S;

$X_{56}$ is selected from the group consisting of H, K, and R, preferably H and R; and $X_{57}$ is selected from the group consisting of D and E.

7. The engineered polypeptide according to item 6, wherein independently of each other the amino acid sequence of $X_3$ to $X_{10}$ is selected from the group consisting of DVTAYEES (SEQ ID NO: 21), DVDAYENS (SEQ ID NO: 22), DVAEYEKS (SEQ ID NO: 23), DVEAYEKS (SEQ ID NO: 24), DVDAYEKS (SEQ ID NO: 25), DVSKYEAS (SEQ ID NO: 26), NVKAYEDS (SEQ ID NO: 27), DVKKYENS (SEQ ID NO: 28), DVDAYQAS (SEQ ID NO: 29), and DVDAYQAS (SEQ ID NO: 30), the amino acid sequence of $X_{18}$ to $X_{24}$ is selected from the group consisting of IQPLEKD (SEQ ID NO: 31), IQPVEKD (SEQ ID NO: 32), IKPLEKD (SEQ ID NO: 33), IVPLTKD (SEQ ID NO: 34), IEPVETD (SEQ ID NO: 35) and IKPLTED (SEQ ID NO: 36), the amino acid sequence of $X_{25}$ to $X_{31}$ is selected from the group consisting of FKARVMV (SEQ ID NO: 37), FRAKLMV (SEQ ID NO: 38), and FRAKVMV (SEQ ID NO: 39), the amino acid sequence of $X_{33}$ to $X_{39}$ is selected from the group consisting of YEWFEF (SEQ ID NO: 40), YEWVEF (SEQ ID NO: 41), and YEWAEF (SEQ ID NO: 42).

8. The engineered polypeptide according to any of items 1 or 3 to 7, wherein independently of each other the target specific binding domain of the first RGD loop has a length of between 5 to 300 amino acids, preferably between 6 to 200 amino acids; the target specific binding domain of the second RGD loop has a length of between 5 to 300 amino acids, preferably between 10 to 200 amino acid; and/or the target specific binding domain in the V loop has a length of between 5 to 300 amino acids, preferably between 10 to 200 amino acid.

9. The engineered polypeptide according to any of items 1 or 3 to 8, wherein at least one of the target specific binding domain is capable of specifically binding to an immunogenic peptide, pathogen neutralizing peptide, viral peptide, bacterial peptide, immune-modulating peptide, cancer peptide, to the surface of a cell, preferably a cellular receptor, a low molecular weight tag, preferably biotin or chitin.
10. The engineered polypeptide according to any of items 1 to 9, wherein the non-adenoviral polypeptide or the polypeptide is selected from the group consisting of immunogenic peptides, pathogen neutralizing peptides, viral peptides, bacterial peptides, immune-modulating peptides, and cancer peptides.
11. The engineered polypeptide according to any of item 10, wherein the non-adenoviral peptide or the peptide comprises a protease cleavage site, preferably a sequence specific endopeptidase cleavage site, more preferably tobacco etch virus NIa protease (TEV).
12. The engineered polypeptide according to any of items 1 to 11, wherein the coupling residue is selected from the group comprising Lys, Cys, Asp, and Glu, preferably Cys.
13. The engineered polypeptide according to any of items 1 to 12, wherein the drug is selected from the group chemotherapeutic drug, antipathogenic drug, immune modulating drug, and anti-inflammatory drug.
14. The engineered polypeptide according to item 2, wherein the fibre protein fragment comprises:

$X_{58}$-F-N-P-V-Y-P-Y-$X_{59}$ (SEQ ID NO: 43)

wherein $X_{58}$ is selected from the group consisting of S, D and T, preferably S or D, and is more preferably S; and $X_{59}$ is selected from the group consisting of E, D and G, is preferably E or D, and is more preferably E.

15. The engineered polypeptide according to item 14, wherein the fibre protein fragment has a length between 9 to 20 amino acids.
16. The engineered polypeptide according to item 2 and 14 or 15, wherein at least one coupling residue in inserted into and/or positioned at the N- and/or C-terminus of the fibre protein fragment, preferably inserted into and/or positioned at the N- and/or C-terminus of SEQ ID NO: 43 or attached to an amino acid of the fibre protein fragment.
17. A nucleic acid encoding the polypeptide according to any of items 1 to 16.
18. An expression vector comprising the nucleic acid of item 17.
19. A cloning vector encoding:
    (i) a polypeptide comprising an adenovirus penton base protomer, wherein said penton base protomer comprises a first RGD-loop, a second RGD-loop, a variable loop and/or a binding site for adenovirus fibre protein adapted for introducing nucleic acids encoding non-adenoviral peptides into the nucleic acids encoding the first RGD-loop, the second RGD-loop and/or the variable loop; or
    (ii) polypeptide comprising an adenovirus fibre protein N-terminal fragment specifically binding to an adenovirus fibre protein binding cleft of a penton base protomer adapted for introducing nucleic acids encoding non-adenoviral peptides a the C- and/or N-terminus.
20. The cloning vector of item 19, wherein the adaptation comprises one or more restriction enzyme sites, preferably BamHI, KpnI, KasI, NarI, SfdI, EcoRI and RsrII, PfoI, BssHII, SalI, Sacd, XbaI, BstEII, and HindIII.
21. A recombinant host cell comprising the expression vector of item 18 or the cloning vector of item 19 or 20.
22. A pentamer comprising five engineered polypeptides comprising adenovirus penton base protomer according items 1, 3 to 13.
23. A virus-like particle (VLP) comprising 12 pentamers according to item 22.
24. The VLP according to item 23, which further comprises at least one engineered polypeptide comprising an adenovirus fibre protein N-terminal fragment specifically binding to an adenovirus fibre protein binding cleft of a penton base protomer according to items 2 to 4 and 10 to 16.
25. The VLP according to item 24, which further comprises at least one mutation in Cys in the amino acids residues such as G51C, S555C, G53C, Y64C, S54C, D114C.
26. A VLP comprising 12 pentamers each comprising five adenovirus penton base protomers and at least one engineered polypeptide comprising an adenovirus fibre protein N-terminal fragment specifically binding to an adenovirus fibre protein binding cleft of a penton base protomer according to items 2 to 4 and 10 to 16.
27. A method for producing an engineered polypeptide according to any of items 1 to 16, comprising the steps of:
    (a) providing a recombinant host cell of item 21;
    (b) expressing the engineered polypeptide; and
    (c) purifying the engineered polypeptide.
28. A method for producing a VLP according to any of items 23 to 26 comprising the steps of the method of item 27 and the further step of allowing the engineered polypeptides to assemble into a VLP.
29. The method of item 28 further comprising the step of incubating the VLP with a protease, preferably a sequence specific endopeptidase cleavage site, more preferably TEV.

30. A method for producing a VLP according to any of items 23 to 26 comprising disease and/or patient specific non-adenoviral peptides, comprising the steps of:
   (a) providing a cloning vector of item 19 and/or 20;
   (b) determining the amino acid sequence of disease or patient specific non-adenoviral peptides;
   (c) inserting nucleic acids encoding at least one of said non-adenoviral peptides into nucleic acids encoding the first RGD-loop, the second RGD-loop and/or the variable loop of the adenovirus penton base protomer, and/or at nucleic acid position preceding or subsequent to nucleic acids encoding the N- or C-terminus of the engineered polypeptide comprising an adenovirus fibre protein N-terminal fragment specifically binding to an adenovirus fibre protein binding cleft of a penton base protomer;
   (d) expressing the engineered adenovirus penton base protomer in a host cell, optionally together with the engineered polypeptide comprising an adenovirus fibre protein N-terminal fragment specifically binding to an adenovirus fibre protein binding cleft of a penton base protomer; and
   (e) purifying said VLP optionally comprising an adenovirus penton base protomer binding fibre protein fragment, or said engineered polypeptide comprising an adenovirus penton base protomer binding fibre protein fragment.

31. A method for producing a VLP according to any of items 23 to 26 comprising disease and/or patient specific non-adenoviral peptides, comprising the steps of:
   (a) providing a cloning vector of item 20;
   (b) determining the amino acid sequence of disease or patient specific non-adenoviral peptides;
   (c) inserting nucleic acids encoding at least one of said non-adenoviral peptides at nucleic acid position preceding or subsequent to nucleic acids encoding the N- or C-terminus of the engineered polypeptide comprising an adenovirus fibre protein N-terminal fragment specifically binding to an adenovirus fibre protein binding cleft of a penton base protomer;
   (d) expressing the engineered polypeptide comprising an adenovirus fibre protein N-terminal fragment specifically binding to an adenovirus fibre protein binding cleft of a penton base protomer in a host cell, optionally together with an adenovirus penton base protomer; and
   (e1) purifying said engineered polypeptide comprising an adenovirus fibre protein N-terminal fragment specifically binding to an adenovirus fibre protein binding cleft of a penton base protomer and admixing with adenovirus penton base protomers or engineered adenovirus penton base protomers of any of items 1 or 3 to 13; or
   (e2) purifying said VLP in case that the adenovirus penton base protomer was co-expressed.

32. A method for producing a VLP according to any of items 23 to 26 comprising disease and/or patient specific non-adenoviral peptides, comprising the steps of:
   (a) determining the amino acid sequence of disease or patient specific non-adenoviral peptides;
   (b) synthesizing an engineered polypeptide according to any of items 2 to 4 and 10 to 16 comprising an adenovirus fibre protein N-terminal fragment specifically binding to an adenovirus fibre protein binding cleft of a penton base protomer and at least one of said non-adenoviral peptides; and
   (c) admixing said engineered polypeptide with adenovirus penton base protomers or engineered adenovirus penton base protomers of any of items 1 or 3 to 10 with pentamers according to item 18 of with VLPs according to item 19.

33. A VLP producible by a method of any of items 28 to 32.

34. A pharmaceutical composition comprising the engineered polypeptides according to any of items 1 to 16, the nucleic acid of item 17, the expression vector of item 18 or the VLP of any of items 23 to 26 or 33, and a pharmaceutically acceptable carrier and/or suitable excipient(s).

35. An engineered polypeptide according to any of items 1 to 16, the nucleic acid of item 17, the expression vector of item 18 or the VLP of any of items 23 to 26 or 33 for treating and/or preventing an infectious disease, an immune disease or cancer.

SEQUENCE LISTING

<160> NUMBER OF SEQ ID NOS: 87

<210> SEQ ID NO 1
<211> LENGTH: 544
<212> TYPE: PRT
<213> ORGANISM: Adenovirus type B 3

<400> SEQUENCE: 1

```
Met Arg Arg Arg Ala Val Leu Gly Gly Ala Val Val Tyr Pro Glu Gly
1               5                   10                  15

Pro Pro Pro Ser Tyr Glu Ser Val Met Gln Gln Gln Ala Ala Met Ile
            20                  25                  30

Gln Pro Pro Leu Glu Ala Pro Phe Val Pro Pro Arg Tyr Leu Ala Pro
        35                  40                  45

Thr Glu Gly Arg Asn Ser Ile Arg Tyr Ser Glu Leu Ser Pro Leu Tyr
    50                  55                  60

Asp Thr Thr Lys Leu Tyr Leu Val Asp Asn Lys Ser Ala Asp Ile Ala
65                  70                  75                  80

Ser Leu Asn Tyr Gln Asn Asp His Ser Asn Phe Leu Thr Val Val
```

```
            85                  90                  95
Gln Asn Asn Asp Phe Thr Pro Thr Glu Ala Ser Thr Gln Thr Ile Asn
            100                 105                 110

Phe Asp Glu Arg Ser Arg Trp Gly Gly Gln Leu Lys Thr Ile Met His
            115                 120                 125

Thr Asn Met Pro Asn Val Asn Glu Tyr Met Phe Ser Asn Lys Phe Lys
            130                 135                 140

Ala Arg Val Met Val Ser Arg Lys Ala Pro Glu Gly Val Thr Val Asn
145                 150                 155                 160

Asp Thr Tyr Asp His Lys Glu Asp Ile Leu Lys Tyr Glu Trp Phe Glu
                165                 170                 175

Phe Ile Leu Pro Glu Gly Asn Phe Ser Ala Thr Met Thr Ile Asp Leu
                180                 185                 190

Met Asn Asn Ala Ile Ile Asp Asn Tyr Leu Glu Ile Gly Arg Gln Asn
                195                 200                 205

Gly Val Leu Glu Ser Asp Ile Gly Val Lys Phe Asp Thr Arg Asn Phe
            210                 215                 220

Arg Leu Gly Trp Asp Pro Glu Thr Lys Leu Ile Met Pro Gly Val Tyr
225                 230                 235                 240

Thr Tyr Glu Ala Phe His Pro Asp Ile Val Leu Leu Pro Gly Cys Gly
                245                 250                 255

Val Asp Phe Thr Glu Ser Arg Leu Ser Asn Leu Leu Gly Ile Arg Lys
            260                 265                 270

Arg His Pro Phe Gln Glu Gly Phe Lys Ile Met Tyr Glu Asp Leu Glu
            275                 280                 285

Gly Gly Asn Ile Pro Ala Leu Leu Asp Val Thr Ala Tyr Glu Glu Ser
            290                 295                 300

Lys Lys Asp Thr Thr Thr Glu Thr Thr Thr Leu Ala Val Ala Glu Glu
305                 310                 315                 320

Thr Ser Glu Asp Asp Ile Thr Arg Gly Asp Thr Tyr Ile Thr Glu
                325                 330                 335

Lys Gln Lys Arg Glu Ala Ala Ala Glu Val Lys Lys Glu Leu Lys
                340                 345                 350

Ile Gln Pro Leu Glu Lys Asp Ser Lys Ser Arg Ser Tyr Asn Val Leu
            355                 360                 365

Glu Asp Lys Ile Asn Thr Ala Tyr Arg Ser Trp Tyr Leu Ser Tyr Asn
            370                 375                 380

Tyr Gly Asn Pro Glu Lys Gly Ile Arg Ser Trp Thr Leu Leu Thr Thr
385                 390                 395                 400

Ser Asp Val Thr Cys Gly Ala Glu Gln Val Tyr Trp Ser Leu Pro Asp
                405                 410                 415

Met Met Gln Asp Pro Val Thr Phe Arg Ser Thr Arg Gln Val Asn Asn
                420                 425                 430

Tyr Pro Val Val Gly Ala Glu Leu Met Pro Val Phe Ser Lys Ser Phe
            435                 440                 445

Tyr Asn Glu Gln Ala Val Tyr Ser Gln Gln Leu Arg Gln Ala Thr Ser
            450                 455                 460

Leu Thr His Val Phe Asn Arg Phe Pro Glu Asn Gln Ile Leu Ile Arg
465                 470                 475                 480

Pro Pro Ala Pro Thr Ile Thr Thr Val Ser Glu Asn Val Pro Ala Leu
                485                 490                 495

Thr Asp His Gly Thr Leu Pro Leu Arg Ser Ser Ile Arg Gly Val Gln
            500                 505                 510
```

```
Arg Val Thr Val Thr Asp Ala Arg Arg Thr Cys Pro Tyr Val Tyr
            515                 520                 525

Lys Ala Leu Gly Ile Val Ala Pro Arg Val Leu Ser Ser Arg Thr Phe
    530                 535                 540
```

<210> SEQ ID NO 2
<211> LENGTH: 571
<212> TYPE: PRT
<213> ORGANISM: Adenovirus type C 2

<400> SEQUENCE: 2

```
Met Gln Arg Ala Ala Met Tyr Glu Glu Gly Pro Pro Ser Tyr Glu
1               5                   10                  15

Ser Val Val Ser Ala Ala Pro Val Ala Ala Leu Gly Ser Pro Phe
            20                  25                  30

Asp Ala Pro Leu Asp Pro Pro Phe Val Pro Pro Arg Tyr Leu Arg Pro
                35                  40                  45

Thr Gly Gly Arg Asn Ser Ile Arg Tyr Ser Glu Leu Ala Pro Leu Phe
    50                  55                  60

Asp Thr Thr Arg Val Tyr Leu Val Asp Asn Lys Ser Thr Asp Val Ala
65                  70                  75                  80

Ser Leu Asn Tyr Gln Asn Asp His Ser Asn Phe Leu Thr Thr Val Ile
                85                  90                  95

Gln Asn Asn Asp Tyr Ser Pro Gly Glu Ala Ser Thr Gln Thr Ile Asn
            100                 105                 110

Leu Asp Asp Arg Ser His Trp Gly Gly Asp Leu Lys Thr Ile Leu His
            115                 120                 125

Thr Asn Met Pro Asn Val Asn Glu Phe Met Phe Thr Asn Lys Phe Lys
    130                 135                 140

Ala Arg Val Met Val Ser Arg Ser Leu Thr Lys Asp Lys Gln Val Glu
145                 150                 155                 160

Leu Lys Tyr Glu Trp Val Glu Phe Thr Leu Pro Glu Gly Asn Tyr Ser
                165                 170                 175

Glu Thr Met Thr Ile Asp Leu Met Asn Asn Ala Ile Val Glu His Tyr
            180                 185                 190

Leu Lys Val Gly Arg Gln Asn Gly Val Leu Glu Ser Asp Ile Gly Val
            195                 200                 205

Lys Phe Asp Thr Arg Asn Phe Arg Leu Gly Phe Asp Pro Val Thr Gly
    210                 215                 220

Leu Val Met Pro Gly Val Tyr Thr Asn Glu Ala Phe His Pro Asp Ile
225                 230                 235                 240

Ile Leu Leu Pro Gly Cys Gly Val Asp Phe Thr His Ser Arg Leu Ser
                245                 250                 255

Asn Leu Leu Gly Ile Arg Lys Arg Gln Pro Phe Gln Glu Gly Phe Arg
            260                 265                 270

Ile Thr Tyr Asp Asp Leu Glu Gly Gly Asn Ile Pro Ala Leu Leu Asp
            275                 280                 285

Val Asp Ala Tyr Gln Ala Ser Leu Lys Asp Asp Thr Glu Gln Gly Gly
    290                 295                 300

Asp Gly Ala Gly Gly Gly Asn Asn Ser Gly Ser Gly Ala Glu Glu Asn
305                 310                 315                 320

Ser Asn Ala Ala Ala Ala Ala Met Gln Pro Val Glu Asp Met Asn Asp
                325                 330                 335

His Ala Ile Arg Gly Asp Thr Phe Ala Thr Arg Ala Glu Glu Lys Arg
```

```
                    340                 345                 350
Ala Glu Ala Glu Ala Ala Glu Ala Ala Pro Ala Ala Gln Pro
                355                 360                 365

Glu Val Glu Lys Pro Gln Lys Lys Pro Val Ile Lys Pro Leu Thr Glu
        370                 375                 380

Asp Ser Lys Lys Arg Ser Tyr Asn Leu Ile Ser Asn Asp Ser Thr Phe
385                 390                 395                 400

Thr Gln Tyr Arg Ser Trp Tyr Leu Ala Tyr Asn Tyr Gly Asp Pro Gln
                405                 410                 415

Thr Gly Ile Arg Ser Trp Thr Leu Leu Cys Thr Pro Asp Val Thr Cys
                420                 425                 430

Gly Ser Glu Gln Val Tyr Trp Ser Leu Pro Asp Met Met Gln Asp Pro
                435                 440                 445

Val Thr Phe Arg Ser Thr Ser Gln Ile Ser Asn Phe Pro Val Val Gly
                450                 455                 460

Ala Glu Leu Leu Pro Val His Ser Lys Ser Phe Tyr Asn Asp Gln Ala
465                 470                 475                 480

Val Tyr Ser Gln Leu Ile Arg Gln Phe Thr Ser Leu Thr His Val Phe
                485                 490                 495

Asn Arg Phe Pro Glu Asn Gln Ile Leu Ala Arg Pro Pro Ala Pro Thr
                500                 505                 510

Ile Thr Thr Val Ser Glu Asn Val Pro Ala Leu Thr Asp His Gly Thr
                515                 520                 525

Leu Pro Leu Arg Asn Ser Ile Gly Gly Val Gln Arg Val Thr Ile Thr
                530                 535                 540

Asp Ala Arg Arg Arg Thr Cys Pro Tyr Val Tyr Lys Ala Leu Gly Ile
545                 550                 555                 560

Val Ser Pro Arg Val Leu Ser Ser Arg Thr Phe
                565                 570

<210> SEQ ID NO 3
<211> LENGTH: 561
<212> TYPE: PRT
<213> ORGANISM: Adenovirus type B 35

<400> SEQUENCE: 3

Met Arg Arg Val Val Leu Gly Gly Ala Val Tyr Pro Glu Gly Pro Pro
1               5                   10                  15

Pro Pro Ser Tyr Glu Ser Val Met Gln Gln Gln Gln Ala Thr Ala Val
                20                  25                  30

Met Gln Ser Pro Leu Glu Ala Pro Phe Val Pro Pro Arg Tyr Leu Ala
            35                  40                  45

Pro Thr Glu Gly Arg Asn Ser Ile Arg Tyr Ser Glu Leu Ala Pro Gln
        50                  55                  60

Tyr Asp Thr Thr Arg Leu Tyr Leu Val Asp Asn Lys Ser Ala Asp Ile
65                  70                  75                  80

Ala Ser Leu Asn Tyr Gln Asn Asp His Ser Asn Phe Leu Thr Thr Val
                85                  90                  95

Val Gln Asn Asn Asp Phe Thr Pro Thr Glu Ala Ser Thr Gln Thr Ile
                100                 105                 110

Asn Phe Asp Glu Arg Ser Arg Trp Gly Gly Gln Leu Lys Thr Ile Met
            115                 120                 125

His Thr Asn Met Pro Asn Val Asn Glu Tyr Met Phe Ser Asn Lys Phe
        130                 135                 140
```

```
Lys Ala Arg Val Met Val Ser Arg Lys Pro Asp Gly Ala Ala Val
145                 150                 155                 160

Gly Asp Thr Tyr Asp His Lys Gln Asp Ile Leu Glu Tyr Glu Trp Phe
            165                 170                 175

Glu Phe Thr Leu Pro Glu Gly Asn Phe Ser Val Thr Met Thr Ile Asp
            180                 185                 190

Leu Met Asn Asn Ala Ile Ile Asp Asn Tyr Leu Lys Val Gly Arg Gln
            195                 200                 205

Asn Gly Val Leu Glu Ser Asp Ile Gly Val Lys Phe Asp Thr Arg Asn
    210                 215                 220

Phe Lys Leu Gly Trp Asp Pro Glu Thr Lys Leu Ile Met Pro Gly Val
225                 230                 235                 240

Tyr Thr Tyr Glu Ala Phe His Pro Asp Ile Val Leu Leu Pro Gly Cys
            245                 250                 255

Gly Val Asp Phe Thr Glu Ser Arg Leu Ser Asn Leu Leu Gly Ile Arg
            260                 265                 270

Lys Lys Gln Pro Phe Gln Glu Gly Phe Lys Ile Leu Tyr Glu Asp Leu
            275                 280                 285

Glu Gly Gly Asn Ile Pro Ala Leu Leu Asp Val Asp Ala Tyr Glu Asn
            290                 295                 300

Ser Lys Lys Glu Gln Lys Ala Lys Ile Glu Ala Ala Thr Ala Ala Ala
305                 310                 315                 320

Glu Ala Lys Ala Asn Ile Val Ala Ser Asp Ser Thr Arg Val Ala Asn
                325                 330                 335

Ala Gly Glu Val Arg Gly Asp Asn Phe Ala Pro Thr Pro Val Pro Thr
            340                 345                 350

Ala Glu Ser Leu Leu Ala Asp Val Ser Glu Gly Thr Asp Val Lys Leu
            355                 360                 365

Thr Ile Gln Pro Val Glu Lys Asp Ser Lys Asn Arg Ser Tyr Asn Val
            370                 375                 380

Leu Glu Asp Lys Ile Asn Thr Ala Tyr Arg Ser Trp Tyr Leu Ser Tyr
385                 390                 395                 400

Asn Tyr Gly Asp Pro Glu Lys Gly Val Arg Ser Trp Thr Leu Leu Thr
            405                 410                 415

Thr Ser Asp Val Thr Cys Gly Ala Glu Gln Val Tyr Trp Ser Leu Pro
            420                 425                 430

Asp Met Met Lys Asp Pro Val Thr Phe Arg Ser Thr Arg Gln Val Ser
            435                 440                 445

Asn Tyr Pro Val Val Gly Ala Glu Leu Met Pro Val Phe Ser Lys Ser
    450                 455                 460

Phe Tyr Asn Glu Gln Ala Val Tyr Ser Gln Gln Leu Arg Gln Ser Thr
465                 470                 475                 480

Ser Leu Thr His Val Phe Asn Arg Phe Pro Glu Asn Gln Ile Leu Ile
            485                 490                 495

Arg Pro Pro Ala Pro Thr Ile Thr Thr Val Ser Glu Asn Val Pro Ala
            500                 505                 510

Leu Thr Asp His Gly Thr Leu Pro Leu Arg Ser Ser Ile Arg Gly Val
            515                 520                 525

Gln Arg Val Thr Val Thr Asp Ala Arg Arg Thr Cys Pro Tyr Val
            530                 535                 540

Tyr Lys Ala Leu Gly Ile Val Ala Pro Arg Val Leu Ser Ser Arg Thr
545                 550                 555                 560

Phe
```

<210> SEQ ID NO 4
<211> LENGTH: 535
<212> TYPE: PRT
<213> ORGANISM: Adenovirus type E 4

<400> SEQUENCE: 4

```
Met Met Arg Arg Ala Tyr Pro Glu Gly Pro Pro Ser Tyr Glu Ser
1               5                   10                  15

Val Met Gln Gln Ala Met Ala Ala Ala Ile Gln Pro Pro Leu
            20                  25                  30

Glu Ala Pro Tyr Val Pro Pro Arg Tyr Leu Ala Pro Thr Glu Gly Arg
                35                  40                  45

Asn Ser Ile Arg Tyr Ser Glu Leu Thr Pro Leu Tyr Asp Thr Thr Arg
            50                  55                  60

Leu Tyr Leu Val Asp Asn Lys Ser Ala Asp Ile Ala Ser Leu Asn Tyr
65              70                  75                  80

Gln Asn Asp His Ser Asn Phe Leu Thr Thr Val Val Gln Asn Asn Asp
                85                  90                  95

Phe Thr Pro Thr Glu Ala Ser Thr Gln Thr Ile Asn Phe Asp Glu Arg
            100                 105                 110

Ser Arg Trp Gly Gly Gln Leu Lys Thr Ile Met His Thr Asn Met Pro
            115                 120                 125

Asn Val Asn Gln Phe Met Tyr Ser Asn Lys Phe Lys Ala Arg Val Met
            130                 135                 140

Val Ser Arg Lys Thr Pro Asn Gly Val Thr Val Gly Asp Asn Tyr Asp
145             150                 155                 160

Gly Ser Gln Asp Glu Leu Lys Tyr Glu Trp Val Glu Phe Glu Leu Pro
                165                 170                 175

Glu Gly Asn Phe Ser Val Thr Met Thr Ile Asp Leu Met Asn Asn Ala
            180                 185                 190

Ile Ile Asp Asn Tyr Leu Ala Val Gly Arg Gln Asn Gly Val Leu Glu
            195                 200                 205

Ser Asp Ile Gly Val Lys Phe Asp Thr Arg Asn Phe Arg Leu Gly Trp
210             215                 220

Asp Pro Val Thr Glu Leu Val Met Pro Gly Val Tyr Thr Asn Glu Ala
225             230                 235                 240

Phe His Pro Asp Ile Val Leu Leu Pro Gly Cys Gly Val Asp Phe Thr
                245                 250                 255

Glu Ser Arg Leu Ser Asn Leu Leu Gly Ile Arg Lys Arg Gln Pro Phe
            260                 265                 270

Gln Glu Gly Phe Gln Ile Met Tyr Glu Asp Leu Asp Gly Gly Asn Ile
            275                 280                 285

Pro Ala Leu Leu Asp Val Glu Ala Tyr Glu Lys Ser Lys Glu Glu Ser
            290                 295                 300

Val Ala Ala Ala Thr Thr Ala Val Ala Thr Ala Ser Thr Glu Val Arg
305             310                 315                 320

Asp Asp Asn Phe Ala Ser Ala Ala Ala Val Ala Ala Val Lys Ala Asp
                325                 330                 335

Glu Thr Lys Ser Lys Ile Val Ile Gln Pro Val Glu Lys Asp Ser Lys
            340                 345                 350

Glu Arg Ser Tyr Asn Val Leu Ser Asp Lys Lys Asn Thr Ala Tyr Arg
            355                 360                 365

Ser Trp Tyr Leu Ala Tyr Asn Tyr Gly Asp Arg Asp Lys Gly Val Arg
```

```
                    370                 375                 380
Ser Trp Thr Leu Leu Thr Thr Ser Asp Val Thr Cys Gly Val Glu Gln
385                 390                 395                 400

Val Tyr Trp Ser Leu Pro Asp Met Met Gln Asp Pro Val Thr Phe Arg
                405                 410                 415

Ser Thr His Gln Val Ser Asn Tyr Pro Val Val Gly Ala Glu Leu Leu
                420                 425                 430

Pro Val Tyr Ser Lys Ser Phe Phe Asn Glu Gln Ala Val Tyr Ser Gln
                435                 440                 445

Gln Leu Arg Ala Phe Thr Ser Leu Thr His Val Phe Asn Arg Phe Pro
            450                 455                 460

Glu Asn Gln Ile Leu Val Arg Pro Pro Ala Pro Thr Ile Thr Thr Val
465                 470                 475                 480

Ser Glu Asn Val Pro Ala Leu Thr Asp His Gly Thr Leu Pro Leu Arg
                485                 490                 495

Ser Ser Ile Arg Gly Val Gln Arg Val Thr Val Thr Asp Ala Arg Arg
                500                 505                 510

Arg Thr Cys Pro Tyr Val Tyr Lys Ala Leu Gly Ile Val Ala Pro Arg
            515                 520                 525

Val Leu Ser Ser Arg Thr Phe
        530                 535

<210> SEQ ID NO 5
<211> LENGTH: 571
<212> TYPE: PRT
<213> ORGANISM: Adenovirus type C 5

<400> SEQUENCE: 5

Met Arg Arg Ala Ala Met Tyr Glu Glu Gly Pro Pro Pro Ser Tyr Glu
1               5                   10                  15

Ser Val Val Ser Ala Ala Pro Val Ala Ala Ala Leu Gly Ser Pro Phe
                20                  25                  30

Asp Ala Pro Leu Asp Pro Pro Phe Val Pro Pro Arg Tyr Leu Arg Pro
            35                  40                  45

Thr Gly Gly Arg Asn Ser Ile Arg Tyr Ser Glu Leu Ala Pro Leu Phe
        50                  55                  60

Asp Thr Thr Arg Val Tyr Leu Val Asp Asn Lys Ser Thr Asp Val Ala
65                  70                  75                  80

Ser Leu Asn Tyr Gln Asn Asp His Ser Asn Phe Leu Thr Thr Val Ile
                85                  90                  95

Gln Asn Asn Asp Tyr Ser Pro Gly Glu Ala Ser Thr Gln Thr Ile Asn
                100                 105                 110

Leu Asp Asp Arg Ser His Trp Gly Gly Asp Leu Lys Thr Ile Leu His
            115                 120                 125

Thr Asn Met Pro Asn Val Asn Glu Phe Met Phe Thr Asn Lys Phe Lys
130                 135                 140

Ala Arg Val Met Val Ser Arg Leu Pro Thr Lys Asp Asn Gln Val Glu
145                 150                 155                 160

Leu Lys Tyr Glu Trp Val Glu Phe Thr Leu Pro Glu Gly Asn Tyr Ser
                165                 170                 175

Glu Thr Met Thr Ile Asp Leu Met Asn Asn Ala Ile Val Glu His Tyr
            180                 185                 190

Leu Lys Val Gly Arg Gln Asn Gly Val Leu Glu Ser Asp Ile Gly Val
        195                 200                 205
```

```
Lys Phe Asp Thr Arg Asn Phe Arg Leu Gly Phe Asp Pro Val Thr Gly
    210                 215                 220
Leu Val Met Pro Gly Val Tyr Thr Asn Glu Ala Phe His Pro Asp Ile
225                 230                 235                 240
Ile Leu Leu Pro Gly Cys Gly Val Asp Phe Thr His Ser Arg Leu Ser
                245                 250                 255
Asn Leu Leu Gly Ile Arg Lys Arg Gln Pro Phe Gln Glu Gly Phe Arg
            260                 265                 270
Ile Thr Tyr Asp Asp Leu Glu Gly Gly Asn Ile Pro Ala Leu Leu Asp
        275                 280                 285
Val Asp Ala Tyr Gln Ala Ser Leu Lys Asp Asp Thr Glu Gln Gly Gly
    290                 295                 300
Gly Gly Ala Gly Gly Ser Asn Ser Ser Gly Ser Gly Ala Glu Glu Asn
305                 310                 315                 320
Ser Asn Ala Ala Ala Ala Met Gln Pro Val Glu Asp Met Asn Asp
                325                 330                 335
His Ala Ile Arg Gly Asp Thr Phe Ala Thr Arg Ala Glu Glu Lys Arg
            340                 345                 350
Ala Glu Ala Glu Ala Ala Glu Ala Ala Pro Ala Ala Gln Pro
    355                 360                 365
Glu Val Glu Lys Pro Gln Lys Lys Pro Val Ile Lys Pro Leu Thr Glu
    370                 375                 380
Asp Ser Lys Lys Arg Ser Tyr Asn Leu Ile Ser Asn Asp Ser Thr Phe
385                 390                 395                 400
Thr Gln Tyr Arg Ser Trp Tyr Leu Ala Tyr Asn Tyr Gly Asp Pro Gln
                405                 410                 415
Thr Gly Ile Arg Ser Trp Thr Leu Leu Cys Thr Pro Asp Val Thr Cys
            420                 425                 430
Gly Ser Glu Gln Val Tyr Trp Ser Leu Pro Asp Met Met Gln Asp Pro
        435                 440                 445
Val Thr Phe Arg Ser Thr Arg Gln Ile Ser Asn Phe Pro Val Val Gly
    450                 455                 460
Ala Glu Leu Leu Pro Val His Ser Lys Ser Phe Tyr Asn Asp Gln Ala
465                 470                 475                 480
Val Tyr Ser Gln Leu Ile Arg Gln Phe Thr Ser Leu Thr His Val Phe
                485                 490                 495
Asn Arg Phe Pro Glu Asn Gln Ile Leu Ala Arg Pro Pro Ala Pro Thr
            500                 505                 510
Ile Thr Thr Val Ser Glu Asn Val Pro Ala Leu Thr Asp His Gly Thr
        515                 520                 525
Leu Pro Leu Arg Asn Ser Ile Gly Gly Val Gln Arg Val Thr Ile Thr
    530                 535                 540
Asp Ala Arg Arg Arg Thr Cys Pro Tyr Val Tyr Lys Ala Leu Gly Ile
545                 550                 555                 560
Val Ser Pro Arg Val Leu Ser Arg Thr Phe
                565                 570
```

<210> SEQ ID NO 6
<211> LENGTH: 532
<212> TYPE: PRT
<213> ORGANISM: Adenovirus type Y25

<400> SEQUENCE: 6

```
Met Met Arg Arg Ala Tyr Pro Glu Gly Pro Pro Ser Tyr Glu Ser
1               5                   10                  15
```

```
Val Met Gln Gln Ala Met Ala Ala Ala Ala Met Gln Pro Pro Leu
            20              25              30
Glu Ala Pro Tyr Val Pro Arg Tyr Leu Ala Pro Thr Glu Gly Arg
        35              40              45
Asn Ser Ile Arg Tyr Ser Glu Leu Ala Pro Leu Tyr Asp Thr Thr Arg
50              55              60
Leu Tyr Leu Val Asp Asn Lys Ser Ala Asp Ile Ala Ser Leu Asn Tyr
65              70              75              80
Gln Asn Asp His Ser Asn Phe Leu Thr Thr Val Val Gln Asn Asn Asp
                85              90              95
Phe Thr Pro Thr Glu Ala Ser Thr Gln Thr Ile Asn Phe Asp Glu Arg
            100             105             110
Ser Arg Trp Gly Gly Gln Leu Lys Thr Ile Met His Thr Asn Met Pro
            115             120             125
Asn Val Asn Glu Phe Met Tyr Ser Asn Lys Phe Lys Ala Arg Val Met
    130             135             140
Val Ser Arg Lys Thr Pro Asn Gly Val Thr Val Thr Asp Gly Ser Gln
145             150             155             160
Asp Ile Leu Glu Tyr Glu Trp Val Glu Phe Glu Leu Pro Glu Gly Asn
                165             170             175
Phe Ser Val Thr Met Thr Ile Asp Leu Met Asn Asn Ala Ile Ile Asp
            180             185             190
Asn Tyr Leu Ala Val Gly Arg Gln Asn Gly Val Leu Glu Ser Asp Ile
    195             200             205
Gly Val Lys Phe Asp Thr Arg Asn Phe Arg Leu Gly Trp Asp Pro Val
    210             215             220
Thr Glu Leu Val Met Pro Gly Val Tyr Thr Asn Glu Ala Phe His Pro
225             230             235             240
Asp Ile Val Leu Leu Pro Gly Cys Gly Val Asp Phe Thr Glu Ser Arg
            245             250             255
Leu Ser Asn Leu Leu Gly Ile Arg Lys Arg Gln Pro Phe Gln Glu Gly
            260             265             270
Phe Gln Ile Met Tyr Glu Asp Leu Glu Gly Gly Asn Ile Pro Ala Leu
            275             280             285
Leu Asp Val Asp Ala Tyr Glu Lys Ser Lys Glu Glu Ser Ala Ala Ala
    290             295             300
Ala Thr Ala Ala Val Ala Thr Ala Ser Thr Glu Val Arg Gly Asp Asn
305             310             315             320
Phe Ala Ser Pro Ala Ala Val Ala Ala Ala Glu Ala Glu Thr Glu
            325             330             335
Ser Lys Ile Val Ile Gln Pro Val Glu Lys Asp Ser Lys Asp Arg Ser
            340             345             350
Tyr Asn Val Leu Pro Asp Lys Ile Asn Thr Ala Tyr Arg Ser Trp Tyr
            355             360             365
Leu Ala Tyr Asn Tyr Gly Asp Pro Glu Lys Gly Val Arg Ser Trp Thr
    370             375             380
Leu Leu Thr Thr Ser Asp Val Thr Cys Gly Val Glu Gln Val Tyr Trp
385             390             395             400
Ser Leu Pro Asp Met Met Gln Asp Pro Val Thr Phe Arg Ser Thr Arg
            405             410             415
Gln Val Ser Asn Tyr Pro Val Val Gly Ala Glu Leu Leu Pro Val Tyr
            420             425             430
```

-continued

```
Ser Lys Ser Phe Phe Asn Glu Gln Ala Val Tyr Ser Gln Gln Leu Arg
        435                 440                 445

Ala Phe Thr Ser Leu Thr His Val Phe Asn Arg Phe Pro Glu Asn Gln
450                 455                 460

Ile Leu Val Arg Pro Pro Ala Pro Thr Ile Thr Thr Val Ser Glu Asn
465                 470                 475                 480

Val Pro Ala Leu Thr Asp His Gly Thr Leu Pro Leu Arg Ser Ser Ile
                485                 490                 495

Arg Gly Val Gln Arg Val Thr Val Thr Asp Ala Arg Arg Thr Cys
                500                 505                 510

Pro Tyr Val Tyr Lys Ala Leu Gly Ile Val Ala Pro Arg Val Leu Ser
            515                 520                 525

Ser Arg Thr Phe
        530

<210> SEQ ID NO 7
<211> LENGTH: 575
<212> TYPE: PRT
<213> ORGANISM: Adenovirus type B 7

<400> SEQUENCE: 7

Met Met Arg Arg Ala Val Leu Gly Gly Ala Val Val Tyr Pro Glu Gly
1               5                   10                  15

Pro Pro Pro Ser Tyr Glu Ser Val Met Gln Gln Gln Ala Ala Ala Val
            20                  25                  30

Met Gln Pro Ser Leu Glu Ala Pro Phe Val Pro Pro Arg Tyr Leu Ala
        35                  40                  45

Pro Thr Glu Gly Arg Asn Ser Ile Arg Tyr Ser Glu Leu Ala Pro Gln
50                  55                  60

Tyr Asp Thr Thr Arg Leu Tyr Leu Val Asp Asn Lys Ser Ala Asp Ile
65                  70                  75                  80

Ala Ser Leu Asn Tyr Gln Asn Asp His Ser Asn Phe Leu Thr Thr Val
                85                  90                  95

Val Gln Asn Asn Asp Phe Thr Pro Thr Glu Ala Ser Thr Gln Thr Ile
            100                 105                 110

Asn Phe Asp Glu Arg Ser Arg Trp Gly Gly Gln Leu Lys Thr Ile Met
        115                 120                 125

His Thr Asn Met Pro Asn Val Asn Glu Tyr Met Phe Ser Asn Lys Phe
    130                 135                 140

Lys Ala Arg Val Met Val Ser Arg Glu Ala Ser Lys Ile Asp Ser Glu
145                 150                 155                 160

Lys Asn Asp Arg Ser Lys Asp Thr Leu Lys Tyr Glu Trp Phe Glu Phe
                165                 170                 175

Thr Leu Pro Glu Gly Asn Phe Ser Ala Thr Met Thr Ile Asp Leu Met
            180                 185                 190

Asn Asn Ala Ile Ile Asp Asn Tyr Leu Ala Val Gly Arg Gln Asn Gly
        195                 200                 205

Val Leu Gln Ser Asp Ile Gly Val Lys Phe Asp Thr Arg Asn Phe Arg
    210                 215                 220

Leu Gly Trp Asp Pro Val Thr Lys Leu Val Met Pro Gly Val Tyr Thr
225                 230                 235                 240

Tyr Glu Ala Phe His Pro Asp Ile Val Leu Leu Pro Asp Cys Gly Val
                245                 250                 255

Asp Phe Thr Glu Ser Arg Leu Ser Asn Leu Leu Gly Ile Arg Lys Arg
            260                 265                 270
```

-continued

```
His Pro Phe Gln Glu Gly Phe Lys Ile Met Tyr Glu Asp Leu Glu Gly
            275                 280                 285

Gly Asn Ile Pro Ala Leu Leu Asp Val Ala Glu Tyr Glu Lys Ser Lys
        290                 295                 300

Lys Glu Ile Ala Ser Ser Thr Thr Thr Ala Val Thr Thr Val Ala
305                 310                 315                 320

Arg Asn Val Ala Asp Thr Ser Val Glu Ala Val Ala Val Ala Val Val
                325                 330                 335

Asp Thr Ile Lys Ala Glu Asn Asp Ser Ala Val Arg Gly Asp Asn Phe
                340                 345                 350

Gln Ser Lys Asn Asp Met Lys Ala Ser Glu Val Thr Val Val Pro
        355                 360                 365

Val Ser Pro Pro Thr Val Thr Glu Thr Glu Thr Lys Glu Pro Thr Ile
370                 375                 380

Lys Pro Leu Glu Lys Asp Thr Lys Asp Arg Ser Tyr Asn Val Ile Ser
385                 390                 395                 400

Gly Thr Asn Asp Thr Ala Tyr Arg Ser Trp Tyr Leu Ala Tyr Asn Tyr
                    405                 410                 415

Gly Asp Pro Glu Lys Gly Val Arg Ser Trp Thr Leu Thr Thr Ser
                420                 425                 430

Asp Val Thr Cys Gly Ala Glu Gln Val Tyr Trp Ser Leu Pro Asp Met
                435                 440                 445

Met Gln Asp Pro Val Thr Phe Arg Ser Thr Arg Gln Val Ser Asn Tyr
        450                 455                 460

Pro Val Val Gly Ala Glu Leu Met Pro Val Phe Ser Lys Ser Phe Tyr
465                 470                 475                 480

Asn Glu Gln Ala Val Tyr Ser Gln Gln Leu Arg Gln Thr Thr Ser Leu
                485                 490                 495

Thr His Ile Phe Asp Arg Phe Pro Glu Asn Gln Ile Leu Ile Arg Pro
                500                 505                 510

Pro Ala Pro Thr Ile Thr Thr Val Ser Glu Asn Val Pro Ala Leu Thr
            515                 520                 525

Asp His Gly Thr Leu Pro Leu Arg Ser Ser Ile Arg Gly Val Gln Arg
        530                 535                 540

Val Thr Val Thr Asp Ala Arg Arg Arg Thr Cys Pro Tyr Val Tyr Lys
545                 550                 555                 560

Ala Leu Gly Ile Val Ala Pro Arg Val Leu Ser Ser Arg Thr Phe
                565                 570                 575

<210> SEQ ID NO 8
<211> LENGTH: 503
<212> TYPE: PRT
<213> ORGANISM: Adenovirus type 52

<400> SEQUENCE: 8

Met Arg Arg Ala Val Arg Val Thr Pro Ala Ala Tyr Glu Gly Pro Pro
1               5                   10                  15

Pro Ser Tyr Glu Ser Val Met Gly Ser Ala Asn Val Pro Ala Thr Leu
            20                  25                  30

Glu Ala Pro Tyr Val Pro Pro Arg Tyr Leu Gly Pro Thr Glu Gly Arg
        35                  40                  45

Asn Ser Ile Arg Tyr Ser Glu Leu Ala Pro Leu Tyr Asp Thr Thr Lys
    50                  55                  60

Val Tyr Leu Val Asp Asn Lys Ser Ala Asp Ile Ala Ser Leu Asn Tyr
```

```
                65                  70                  75                  80
        Gln Asn Asp His Ser Asn Phe Leu Thr Thr Val Val Gln Asn Asn Asp
                                85                  90                  95

Phe Thr Pro Thr Glu Ala Gly Thr Gln Thr Ile Asn Phe Asp Glu Arg
                        100                 105                 110

Ser Arg Trp Gly Gly Gln Leu Lys Thr Ile Leu His Thr Asn Met Pro
                        115                 120                 125

Asn Ile Asn Glu Phe Met Ser Thr Asn Lys Phe Arg Ala Arg Leu Met
                130                 135                 140

Val Lys Lys Val Glu Asn Gln Pro Pro Glu Tyr Glu Trp Phe Glu Phe
        145                 150                 155                 160

Thr Ile Pro Glu Gly Asn Tyr Ser Glu Thr Met Thr Ile Asp Leu Met
                        165                 170                 175

Asn Asn Ala Ile Val Asp Asn Tyr Leu Gln Val Gly Arg Gln Asn Gly
                        180                 185                 190

Val Leu Glu Ser Asp Ile Gly Val Lys Phe Asp Thr Arg Asn Phe Arg
                        195                 200                 205

Leu Gly Trp Asp Pro Val Thr Lys Leu Val Met Pro Gly Val Tyr Thr
                        210                 215                 220

Asn Glu Ala Phe His Pro Asp Ile Val Leu Leu Pro Gly Cys Gly Val
        225                 230                 235                 240

Asp Phe Thr Gln Ser Arg Leu Ser Asn Leu Leu Gly Ile Arg Lys Arg
                        245                 250                 255

Arg Pro Phe Gln Glu Gly Phe Gln Ile Met Tyr Glu Asp Leu Glu Gly
                        260                 265                 270

Gly Asn Ile Pro Ala Leu Leu Asp Val Thr Lys Tyr Glu Gln Ser Val
                        275                 280                 285

Gln Arg Ala Lys Ala Glu Gly Arg Glu Ile Arg Gly Asp Thr Phe Ala
                        290                 295                 300

Val Ser Pro Gln Asp Leu Val Ile Glu Pro Leu Glu His Asp Ser Lys
        305                 310                 315                 320

Asn Arg Ser Tyr Asn Leu Leu Pro Asn Lys Thr Asp Thr Ala Tyr Arg
                        325                 330                 335

Ser Trp Phe Leu Ala Tyr Asn Tyr Gly Asp Pro Glu Lys Gly Val Arg
                        340                 345                 350

Ser Trp Thr Ile Leu Thr Thr Thr Asp Val Thr Cys Gly Ser Gln Gln
                        355                 360                 365

Val Tyr Trp Ser Leu Pro Asp Met Met Gln Asp Pro Val Thr Phe Arg
                        370                 375                 380

Pro Ser Thr Gln Val Ser Asn Phe Pro Val Val Gly Thr Glu Leu Leu
        385                 390                 395                 400

Pro Val His Ala Lys Ser Phe Tyr Asn Glu Gln Ala Val Tyr Ser Gln
                        405                 410                 415

Leu Ile Arg Gln Ser Thr Ala Leu Thr His Val Phe Asn Arg Phe Pro
                        420                 425                 430

Glu Asn Gln Ile Leu Val Arg Pro Pro Ala Pro Thr Ile Thr Thr Val
                        435                 440                 445

Ser Glu Asn Val Pro Ala Leu Thr Asp His Gly Thr Leu Pro Leu Arg
                        450                 455                 460

Ser Ser Ile Ser Gly Val Gln Arg Val Thr Ile Thr Asp Ala Arg Arg
        465                 470                 475                 480

Arg Thr Cys Pro Tyr Val Tyr Lys Ala Leu Gly Val Val Ala Pro Lys
                        485                 490                 495
```

```
Val Leu Ser Ser Arg Thr Phe
            500

<210> SEQ ID NO 9
<211> LENGTH: 504
<212> TYPE: PRT
<213> ORGANISM: Adenovirus type 53

<400> SEQUENCE: 9

Met Arg Arg Ala Val Arg Val Thr Pro Ala Val Tyr Ala Glu Gly Pro
1               5                   10                  15

Pro Pro Ser Tyr Glu Ser Val Met Gly Ser Ala Asn Val Pro Ala Thr
            20                  25                  30

Leu Glu Ala Pro Tyr Val Pro Pro Arg Tyr Leu Gly Pro Thr Glu Gly
        35                  40                  45

Arg Asn Ser Ile Arg Tyr Ser Glu Leu Ala Pro Leu Tyr Asp Thr Thr
    50                  55                  60

Lys Val Tyr Leu Val Asp Asn Lys Ser Ala Asp Ile Ala Ser Leu Asn
65                  70                  75                  80

Tyr Gln Asn Asp His Ser Asn Phe Leu Thr Thr Val Val Gln Asn Asn
                85                  90                  95

Asp Phe Thr Pro Thr Glu Ala Gly Thr Gln Thr Ile Asn Phe Asp Glu
            100                 105                 110

Arg Ser Arg Trp Gly Gly Gln Leu Lys Thr Ile Leu His Thr Asn Met
        115                 120                 125

Pro Asn Ile Asn Glu Phe Met Ser Thr Asn Lys Phe Arg Ala Arg Leu
    130                 135                 140

Met Val Glu Lys Thr Ser Gly Gln Pro Pro Lys Tyr Glu Trp Phe Glu
145                 150                 155                 160

Phe Thr Ile Pro Glu Gly Asn Tyr Ser Glu Thr Met Thr Ile Asp Leu
                165                 170                 175

Met Asn Asn Ala Ile Val Asp Asn Tyr Leu Gln Val Gly Arg Gln Asn
            180                 185                 190

Gly Val Leu Glu Ser Asp Ile Gly Val Lys Phe Asp Thr Arg Asn Phe
        195                 200                 205

Arg Leu Gly Trp Asp Pro Val Thr Lys Leu Val Met Pro Gly Val Tyr
    210                 215                 220

Thr Asn Glu Ala Phe His Pro Asp Ile Val Leu Leu Pro Gly Cys Gly
225                 230                 235                 240

Val Asp Phe Thr Gln Ser Arg Leu Ser Asn Leu Leu Gly Ile Arg Lys
                245                 250                 255

Arg Arg Pro Phe Gln Glu Gly Phe Gln Ile Met Tyr Glu Asp Leu Glu
            260                 265                 270

Gly Gly Asn Ile Pro Gly Leu Leu Asp Val Pro Ala Tyr Glu Gln Ser
        275                 280                 285

Leu Gln Gln Ala Gln Glu Glu Gly Arg Val Thr Arg Gly Asp Thr Phe
    290                 295                 300

Ala Thr Ala Pro Asn Glu Val Val Ile Lys Pro Leu Leu Lys Asp Ser
305                 310                 315                 320

Lys Asp Arg Ser Tyr Asn Ile Ile Thr Asp Thr Asp Thr Leu Tyr
                325                 330                 335

Arg Ser Trp Phe Leu Ala Tyr Asn Tyr Gly Asp Pro Glu Asn Gly Val
            340                 345                 350

Arg Ser Trp Thr Ile Leu Thr Thr Thr Asp Val Thr Cys Gly Ser Gln
```

```
                        355                 360                 365
Gln Val Tyr Trp Ser Leu Pro Asp Met Met Gln Asp Pro Val Thr Phe
    370                 375                 380

Arg Pro Ser Thr Gln Val Ser Asn Phe Pro Val Val Gly Thr Glu Leu
385                 390                 395                 400

Leu Pro Val His Ala Lys Ser Phe Tyr Asn Glu Gln Ala Val Tyr Ser
                405                 410                 415

Gln Leu Ile Arg Gln Ser Thr Ala Leu Thr His Val Phe Asn Arg Phe
            420                 425                 430

Pro Glu Asn Gln Ile Leu Val Arg Pro Ala Pro Thr Ile Thr Thr
                435                 440                 445

Val Ser Glu Asn Val Pro Ala Leu Thr Asp His Gly Thr Leu Pro Leu
        450                 455                 460

Arg Ser Ser Ile Ser Gly Val Gln Arg Val Thr Ile Thr Asp Ala Arg
465                 470                 475                 480

Arg Arg Thr Cys Pro Tyr Val Tyr Lys Ala Leu Gly Val Val Ala Pro
                485                 490                 495

Lys Val Leu Ser Ser Arg Thr Phe
            500

<210> SEQ ID NO 10
<211> LENGTH: 505
<212> TYPE: PRT
<213> ORGANISM: Adenovirus type 51

<400> SEQUENCE: 10

Met Arg Arg Ala Val Arg Val Thr Pro Ala Ala Tyr Glu Gly Pro Pro
1               5                   10                  15

Pro Ser Tyr Glu Ser Val Met Gly Ser Ala Asn Val Pro Ala Thr Leu
            20                  25                  30

Glu Ala Pro Tyr Val Pro Pro Arg Tyr Leu Gly Pro Thr Glu Gly Arg
        35                  40                  45

Asn Ser Ile Arg Tyr Ser Glu Leu Ala Pro Leu Tyr Asp Thr Thr Lys
    50                  55                  60

Val Tyr Leu Val Asp Asn Lys Ser Ala Asp Ile Ala Ser Leu Asn Tyr
65                  70                  75                  80

Gln Asn Asp His Ser Asn Phe Leu Thr Thr Val Val Gln Asn Asn Asp
                85                  90                  95

Phe Thr Pro Thr Glu Ala Gly Thr Gln Thr Ile Asn Phe Asp Glu Arg
            100                 105                 110

Ser Arg Trp Gly Gly Gln Leu Lys Thr Ile Leu His Thr Asn Met Pro
        115                 120                 125

Asn Ile Asn Glu Phe Met Ser Thr Asn Lys Phe Arg Ala Lys Leu Met
    130                 135                 140

Val Glu Lys Ser Asn Ala Glu Thr Arg Gln Pro Arg Tyr Glu Trp Phe
145                 150                 155                 160

Glu Phe Thr Ile Pro Glu Gly Asn Tyr Ser Glu Thr Met Thr Ile Asp
                165                 170                 175

Leu Met Asn Asn Ala Ile Val Asp Asn Tyr Leu Gln Val Gly Arg Gln
            180                 185                 190

Asn Gly Val Leu Glu Ser Asp Ile Gly Val Lys Phe Asp Thr Arg Asn
        195                 200                 205

Phe Arg Leu Gly Trp Asp Pro Val Thr Lys Leu Val Met Pro Gly Val
    210                 215                 220
```

Tyr Thr Asn Glu Ala Phe His Pro Asp Ile Val Leu Leu Pro Gly Cys
225                 230                 235                 240

Gly Val Asp Phe Thr Gln Ser Arg Leu Ser Asn Leu Leu Gly Ile Arg
            245                 250                 255

Lys Arg Arg Pro Phe Gln Glu Gly Phe Gln Ile Met Tyr Glu Asp Leu
        260                 265                 270

Glu Gly Gly Asn Ile Pro Ala Leu Leu Asp Val Ser Lys Tyr Glu Ala
    275                 280                 285

Ser Ile Gln Arg Ala Lys Ala Glu Gly Arg Glu Ile Arg Gly Asp Thr
290                 295                 300

Phe Ala Val Ala Pro Gln Asp Leu Glu Ile Val Pro Leu Thr Lys Asp
305                 310                 315                 320

Ser Lys Asp Arg Ser Tyr Asn Ile Ile Asn Asn Thr Thr Asp Thr Leu
            325                 330                 335

Tyr Arg Ser Trp Phe Leu Ala Tyr Asn Tyr Gly Asp Pro Glu Lys Gly
        340                 345                 350

Val Arg Ser Trp Thr Ile Leu Thr Thr Thr Asp Val Thr Cys Gly Ser
    355                 360                 365

Gln Gln Val Tyr Trp Ser Leu Pro Asp Met Met Gln Asp Pro Val Thr
370                 375                 380

Phe Arg Pro Ser Thr Gln Val Ser Asn Phe Pro Val Val Gly Thr Glu
385                 390                 395                 400

Leu Leu Pro Val His Ala Lys Ser Phe Tyr Asn Glu Gln Ala Val Tyr
            405                 410                 415

Ser Gln Leu Ile Arg Gln Ser Thr Ala Leu Thr His Val Phe Asn Arg
        420                 425                 430

Phe Pro Glu Asn Gln Ile Leu Val Arg Pro Pro Ala Pro Thr Ile Thr
    435                 440                 445

Thr Val Ser Glu Asn Val Pro Ala Leu Thr Asp His Gly Thr Leu Pro
450                 455                 460

Leu Arg Ser Ser Ile Ser Gly Val Gln Arg Val Thr Ile Thr Asp Ala
465                 470                 475                 480

Arg Arg Arg Thr Cys Pro Tyr Val Tyr Lys Ala Leu Gly Val Val Ala
            485                 490                 495

Pro Lys Val Leu Ser Ser Arg Thr Phe
        500                 505

<210> SEQ ID NO 11
<211> LENGTH: 508
<212> TYPE: PRT
<213> ORGANISM: Adenovirus type 18

<400> SEQUENCE: 11

Met Arg Arg Ala Val Gly Val Pro Pro Val Met Ala Tyr Ala Glu Gly
1               5                   10                  15

Pro Pro Pro Ser Tyr Glu Thr Val Met Gly Ala Ala Asp Ser Pro Ala
            20                  25                  30

Thr Leu Glu Ala Leu Tyr Val Pro Arg Tyr Leu Gly Pro Thr Glu
        35                  40                  45

Gly Arg Asn Ser Ile Arg Tyr Ser Glu Leu Ala Pro Leu Tyr Asp Thr
    50                  55                  60

Thr Arg Val Tyr Leu Val Asp Asn Lys Ser Ala Asp Ile Ala Ser Leu
65                  70                  75                  80

Asn Tyr Gln Asn Asp His Ser Asn Phe Leu Thr Thr Val Val Gln Asn
            85                  90                  95

```
Asn Asp Phe Thr Pro Val Glu Ala Gly Thr Gln Thr Ile Asn Phe Asp
            100                 105                 110

Glu Arg Ser Arg Trp Gly Gly Asp Leu Lys Thr Ile Leu Arg Thr Asn
            115                 120                 125

Met Pro Asn Ile Asn Glu Phe Met Ser Thr Asn Lys Phe Arg Ala Arg
            130                 135                 140

Leu Met Val Glu Lys Val Asn Lys Glu Thr Asn Ala Pro Arg Tyr Glu
145                 150                 155                 160

Trp Phe Glu Phe Thr Leu Pro Glu Gly Asn Tyr Ser Glu Thr Met Thr
                    165                 170                 175

Ile Asp Leu Met Asn Asn Ala Ile Val Asp Asn Tyr Leu Glu Val Gly
            180                 185                 190

Arg Gln Asn Gly Val Leu Glu Ser Asp Ile Gly Val Lys Phe Asp Thr
            195                 200                 205

Arg Asn Phe Arg Leu Gly Trp Asp Pro Val Thr Lys Leu Val Met Pro
            210                 215                 220

Gly Val Tyr Thr Asn Glu Ala Phe His Pro Asp Ile Val Leu Leu Pro
225                 230                 235                 240

Gly Cys Gly Val Asp Phe Thr Gln Ser Arg Leu Ser Asn Leu Leu Gly
                    245                 250                 255

Ile Arg Lys Arg Met Pro Phe Gln Ala Gly Phe Gln Ile Met Tyr Glu
            260                 265                 270

Asp Leu Glu Gly Gly Asn Ile Pro Ala Leu Leu Asp Val Ala Lys Tyr
            275                 280                 285

Glu Ala Ser Ile Gln Lys Ala Arg Glu Gln Gly Gln Glu Ile Arg Gly
            290                 295                 300

Asp Asn Phe Thr Val Ile Pro Arg Asp Val Glu Ile Val Pro Val Glu
305                 310                 315                 320

Lys Asp Ser Lys Asp Arg Ser Tyr Asn Leu Leu Pro Gly Asp Gln Thr
                    325                 330                 335

Asn Thr Ala Tyr Arg Ser Trp Phe Leu Ala Tyr Asn Tyr Gly Asp Pro
            340                 345                 350

Glu Lys Gly Val Arg Ser Trp Thr Leu Leu Thr Thr Asp Val Thr
            355                 360                 365

Cys Gly Ser Gln Gln Val Tyr Trp Ser Leu Pro Asp Met Met Gln Asp
370                 375                 380

Pro Val Thr Phe Arg Pro Ser Gln Val Ser Asn Tyr Pro Val Val
385                 390                 395                 400

Gly Val Glu Leu Leu Pro Val His Ala Lys Ser Phe Tyr Asn Glu Gln
                    405                 410                 415

Ala Val Tyr Ser Gln Leu Ile Arg Gln Ser Thr Ala Leu Thr His Val
            420                 425                 430

Phe Asn Arg Phe Pro Glu Asn Gln Ile Leu Val Arg Pro Pro Ala Pro
            435                 440                 445

Thr Ile Thr Thr Val Ser Glu Asn Val Pro Ala Leu Thr Asp His Gly
            450                 455                 460

Thr Leu Pro Leu Arg Ser Ser Ile Ser Gly Val Gln Arg Val Thr Ile
465                 470                 475                 480

Thr Asp Ala Arg Arg Arg Thr Cys Pro Tyr Val His Lys Ala Leu Gly
                    485                 490                 495

Ile Val Ala Pro Lys Val Leu Ser Ser Arg Thr Phe
            500                 505
```

```
<210> SEQ ID NO 12
<211> LENGTH: 511
<212> TYPE: PRT
<213> ORGANISM: Adenovirus type 49

<400> SEQUENCE: 12

Met Arg Arg Ala Val Pro Ala Ala Ile Pro Ala Thr Val Ala Tyr
1               5                   10                  15

Ala Asp Pro Pro Ser Tyr Glu Ser Val Met Ala Gly Val Pro Ala
            20                  25                  30

Thr Leu Glu Ala Pro Tyr Val Pro Arg Tyr Leu Gly Pro Thr Glu
        35                  40                  45

Gly Arg Asn Ser Ile Arg Tyr Ser Glu Leu Ala Pro Leu Tyr Asp Thr
50                  55                  60

Thr Arg Val Tyr Leu Val Asp Asn Lys Ser Ala Asp Ile Ala Ser Leu
65                  70                  75                  80

Asn Tyr Gln Asn Asp His Ser Asn Phe Leu Thr Thr Val Gln Asn
                85                  90                  95

Asn Asp Phe Thr Pro Val Glu Ala Gly Thr Gln Thr Ile Asn Phe Asp
            100                 105                 110

Glu Arg Ser Arg Trp Gly Gly Gln Leu Lys Thr Ile Leu His Thr Asn
            115                 120                 125

Met Pro Asn Val Asn Glu Phe Met Phe Thr Asn Ser Phe Arg Ala Lys
130                 135                 140

Val Met Val Ser Arg Lys Gln Asn Glu Glu Gly Gln Thr Glu Leu Glu
145                 150                 155                 160

Tyr Glu Trp Val Glu Phe Val Leu Pro Glu Gly Asn Tyr Ser Glu Thr
                165                 170                 175

Met Thr Leu Asp Leu Met Asn Asn Ala Ile Val Asp His Tyr Leu Leu
            180                 185                 190

Val Gly Arg Gln Asn Gly Val Leu Glu Ser Asp Ile Gly Val Lys Phe
            195                 200                 205

Asp Thr Arg Asn Phe Arg Leu Gly Trp Asp Pro Val Thr Lys Leu Val
210                 215                 220

Met Pro Gly Val Tyr Thr Asn Glu Ala Phe His Pro Asp Val Val Leu
225                 230                 235                 240

Leu Pro Gly Cys Gly Val Asp Phe Thr Gln Ser Arg Leu Ser Asn Leu
                245                 250                 255

Leu Gly Ile Arg Lys Arg Gln Pro Phe Gln Glu Gly Phe Arg Ile Met
            260                 265                 270

Tyr Glu Asp Leu Glu Gly Gly Asn Ile Pro Ala Leu Leu Asn Val Lys
            275                 280                 285

Ala Tyr Glu Asp Ser Ile Ala Ala Met Arg Lys His Asn Leu Pro
290                 295                 300

Leu Arg Gly Asp Val Phe Ala Val Gln Pro Gln Glu Ile Val Ile Gln
305                 310                 315                 320

Pro Val Glu Lys Asp Gly Lys Glu Arg Ser Tyr Asn Leu Leu Pro Asp
                325                 330                 335

Asp Lys Asn Asn Thr Ala Tyr Arg Ser Trp Tyr Leu Ala Tyr Asn Tyr
            340                 345                 350

Gly Asp Pro Leu Lys Gly Val Arg Ser Trp Thr Leu Leu Thr Thr Pro
            355                 360                 365

Asp Val Thr Cys Gly Ser Glu Gln Val Tyr Trp Ser Leu Pro Asp Leu
370                 375                 380
```

```
Met Gln Asp Pro Val Thr Phe Arg Pro Ser Ser Gln Val Ser Asn Tyr
385                 390                 395                 400

Pro Val Val Gly Ala Glu Leu Leu Pro Leu Gln Ala Lys Ser Phe Tyr
                405                 410                 415

Asn Glu Gln Ala Val Tyr Ser Gln Leu Ile Arg Gln Ser Thr Ala Leu
            420                 425                 430

Thr His Val Phe Asn Arg Phe Pro Glu Asn Gln Ile Leu Val Arg Pro
        435                 440                 445

Pro Ala Ala Thr Ile Thr Thr Val Ser Glu Asn Val Pro Ala Leu Thr
    450                 455                 460

Asp His Gly Thr Leu Pro Leu Arg Ser Ser Ile Ser Gly Val Gln Arg
465                 470                 475                 480

Val Thr Ile Thr Asp Ala Arg Arg Arg Thr Cys Pro Tyr Val Tyr Lys
                485                 490                 495

Ala Leu Gly Ile Val Ala Pro Arg Val Leu Ser Ser Arg Thr Phe
            500                 505                 510

<210> SEQ ID NO 13
<211> LENGTH: 512
<212> TYPE: PRT
<213> ORGANISM: Adenovirus type 20

<400> SEQUENCE: 13

Met Arg Arg Ala Val Ala Ile Pro Ser Ala Ala Val Ala Leu Gly Pro
1               5                   10                  15

Pro Pro Ser Tyr Glu Ser Val Met Ala Ser Ala Asn Leu Gln Ala Pro
            20                  25                  30

Leu Glu Asn Pro Tyr Val Pro Pro Arg Tyr Leu Glu Pro Thr Gly Gly
        35                  40                  45

Arg Asn Ser Ile Arg Tyr Ser Glu Leu Thr Pro Leu Tyr Asp Thr Thr
    50                  55                  60

Arg Leu Tyr Leu Val Asp Asn Lys Ser Ala Asp Ile Ala Thr Leu Asn
65                  70                  75                  80

Tyr Gln Asn Asp His Ser Asn Phe Leu Thr Ser Val Val Gln Asn Ser
                85                  90                  95

Asp Tyr Thr Pro Ala Glu Ala Ser Thr Gln Thr Ile Asn Leu Asp Asp
            100                 105                 110

Arg Ser Arg Trp Gly Gly Asp Leu Lys Thr Ile Leu His Thr Asn Met
        115                 120                 125

Pro Asn Val Asn Glu Phe Met Phe Thr Asn Ser Phe Arg Ala Lys Leu
    130                 135                 140

Met Val Ala His Glu Thr Asn Lys Asp Pro Val Tyr Lys Trp Val Glu
145                 150                 155                 160

Leu Thr Leu Pro Glu Gly Asn Phe Ser Glu Thr Met Thr Ile Asp Leu
                165                 170                 175

Met Asn Asn Ala Ile Val Asp His Tyr Leu Ala Val Gly Arg Gln Asn
            180                 185                 190

Gly Val Lys Glu Ser Glu Ile Gly Val Lys Phe Asp Thr Arg Asn Phe
        195                 200                 205

Arg Leu Gly Trp Asp Pro Gln Thr Glu Leu Val Met Pro Gly Val Tyr
    210                 215                 220

Thr Asn Glu Ala Phe His Pro Asp Val Leu Leu Pro Gly Cys Gly
225                 230                 235                 240

Val Asp Phe Thr Tyr Ser Arg Leu Ser Asn Leu Leu Gly Ile Arg Lys
```

```
                245                 250                 255
Arg Met Pro Phe Gln Glu Gly Phe Gln Ile Met Tyr Glu Asp Leu Val
        260                 265                 270

Gly Gly Asn Ile Pro Ala Leu Leu Asp Val Pro Ala Tyr Glu Ala Ser
275                 280                 285

Ile Thr Thr Val Ala Ala Lys Glu Val Arg Gly Asp Asn Phe Glu Ala
        290                 295                 300

Ala Ala Ala Ala Ala Thr Gly Ala Gln Pro Gln Ala Ala Pro Val
305                 310                 315                 320

Val Arg Pro Val Thr Gln Asp Ser Lys Gly Arg Ser Tyr Asn Ile Ile
                325                 330                 335

Thr Gly Thr Asn Asn Thr Ala Tyr Arg Ser Trp Tyr Leu Ala Tyr Asn
                340                 345                 350

Tyr Gly Asp Pro Glu Lys Gly Val Arg Ser Trp Thr Leu Leu Thr Thr
                355                 360                 365

Pro Asp Val Thr Cys Gly Ser Glu Gln Val Tyr Trp Ser Met Pro Asp
        370                 375                 380

Met Tyr Val Asp Pro Val Thr Phe Arg Ser Ser Gln Gln Val Ser Ser
385                 390                 395                 400

Tyr Pro Val Val Gly Ala Glu Leu Leu Pro Ile His Ser Lys Ser Phe
                405                 410                 415

Tyr Asn Glu Gln Ala Val Tyr Ser Gln Leu Ile Arg Gln Thr Ala
                420                 425                 430

Leu Thr His Val Phe Asn Arg Phe Pro Glu Asn Gln Ile Leu Val Arg
                435                 440                 445

Pro Pro Ala Pro Thr Ile Thr Thr Val Ser Glu Asn Val Pro Ala Leu
        450                 455                 460

Thr Asp His Gly Thr Leu Pro Leu Gln Asn Ser Ile Arg Gly Val Gln
465                 470                 475                 480

Arg Val Thr Ile Thr Asp Ala Arg Arg Thr Cys Pro Tyr Val Tyr
                485                 490                 495

Lys Ala Leu Gly Ile Val Ala Pro Arg Val Leu Ser Ser Arg Thr Phe
                500                 505                 510

<210> SEQ ID NO 14
<211> LENGTH: 497
<212> TYPE: PRT
<213> ORGANISM: Adenovirus type 12

<400> SEQUENCE: 14

Met Arg Arg Ala Val Glu Leu Gln Thr Val Ala Phe Pro Glu Thr Pro
1               5                   10                  15

Pro Pro Ser Tyr Glu Thr Val Met Ala Ala Pro Tyr Val Pro
                20                  25                  30

Pro Arg Tyr Leu Gly Pro Thr Glu Gly Arg Asn Ser Ile Arg Tyr Ser
                35                  40                  45

Glu Leu Ser Pro Leu Tyr Asp Thr Thr Arg Val Tyr Leu Val Asp Asn
                50                  55                  60

Lys Ser Ser Asp Ile Ala Ser Leu Asn Tyr Gln Asn Asp His Ser Asn
65                  70                  75                  80

Phe Leu Thr Thr Val Val Gln Asn Asn Asp Tyr Ser Pro Ile Glu Ala
                85                  90                  95

Gly Thr Gln Thr Ile Asn Phe Asp Glu Arg Ser Arg Trp Gly Gly Asp
                100                 105                 110
```

```
Leu Lys Thr Ile Leu His Thr Asn Met Pro Asn Val Asn Asp Phe Met
            115                 120                 125

Phe Thr Thr Lys Phe Lys Ala Arg Val Met Val Ala Arg Lys Thr Asn
130                 135                 140

Asn Glu Gly Gln Thr Ile Leu Glu Tyr Glu Trp Ala Glu Phe Val Leu
145                 150                 155                 160

Pro Glu Gly Asn Tyr Ser Glu Thr Met Thr Ile Asp Leu Met Asn Asn
                165                 170                 175

Ala Ile Ile Glu His Tyr Leu Arg Val Gly Arg Gln His Gly Val Leu
            180                 185                 190

Glu Ser Asp Ile Gly Val Lys Phe Asp Thr Arg Asn Phe Arg Leu Gly
        195                 200                 205

Trp Asp Pro Glu Thr Gln Leu Val Thr Pro Gly Val Tyr Thr Asn Glu
    210                 215                 220

Ala Phe His Pro Asp Ile Val Leu Leu Pro Gly Cys Gly Val Asp Phe
225                 230                 235                 240

Thr Glu Ser Arg Leu Ser Asn Ile Leu Gly Ile Arg Lys Arg Gln Pro
                245                 250                 255

Phe Gln Glu Gly Phe Val Ile Met Tyr Glu His Leu Glu Gly Gly Asn
            260                 265                 270

Ile Pro Ala Leu Leu Asp Val Lys Lys Tyr Glu Asn Ser Leu Gln Asp
        275                 280                 285

Gln Asn Thr Val Arg Gly Asp Asn Phe Ile Ala Leu Asn Lys Ala Ala
    290                 295                 300

Arg Ile Glu Pro Val Glu Thr Asp Pro Lys Gly Arg Ser Tyr Asn Leu
305                 310                 315                 320

Leu Pro Asp Lys Lys Asn Thr Lys Tyr Arg Ser Trp Tyr Leu Ala Tyr
                325                 330                 335

Asn Tyr Gly Asp Pro Glu Lys Gly Val Arg Ser Trp Thr Leu Leu Thr
            340                 345                 350

Thr Pro Asp Val Thr Gly Gly Ser Glu Gln Val Tyr Trp Ser Leu Pro
        355                 360                 365

Asp Met Met Gln Asp Pro Val Thr Phe Arg Ser Arg Gln Val Ser
    370                 375                 380

Asn Tyr Pro Val Val Ala Ala Glu Leu Leu Pro Val His Ala Lys Ser
385                 390                 395                 400

Phe Tyr Asn Glu Gln Ala Val Tyr Ser Gln Leu Ile Arg Gln Ser Thr
                405                 410                 415

Ala Leu Thr Arg Val Phe Asn Arg Phe Pro Glu Asn Gln Ile Leu Val
            420                 425                 430

Arg Pro Pro Ala Ala Thr Ile Thr Thr Val Ser Glu Asn Val Pro Ala
        435                 440                 445

Leu Thr Asp His Gly Thr Leu Pro Leu Arg Ser Ser Ile Ser Gly Val
    450                 455                 460

Gln Arg Val Thr Ile Thr Asp Ala Arg Arg Thr Cys Pro Tyr Val
465                 470                 475                 480

Tyr Lys Ala Leu Gly Ile Val Ser Pro Arg Val Leu Ser Ser Arg Thr
                485                 490                 495

Phe

<210> SEQ ID NO 15
<211> LENGTH: 9
<212> TYPE: PRT
<213> ORGANISM: Artificial Sequence
```

```
<220> FEATURE:
<223> OTHER INFORMATION: Consensus sequence of penton base proteins
<220> FEATURE:
<221> NAME/KEY: MISC_FEATURE
<222> LOCATION: (1)..(1)
<223> OTHER INFORMATION: Xaa is selected from the group consisting of D,
      E and N, and is preferably D
<220> FEATURE:
<221> NAME/KEY: MISC_FEATURE
<222> LOCATION: (2)..(2)
<223> OTHER INFORMATION: is selected from the group consisting of V, L,
      and I, and is preferably V
<220> FEATURE:
<221> NAME/KEY: MISC_FEATURE
<222> LOCATION: (3)..(3)
<223> OTHER INFORMATION: is any amino acid, is preferably selected from
      the group consisting of A, D, E, K, S, and T, and is more
      preferably T
<220> FEATURE:
<221> NAME/KEY: MISC_FEATURE
<222> LOCATION: (4)..(4)
<223> OTHER INFORMATION: is any amino acid, is preferably selected from
      the group consisting of A, D, E, and K, and is more preferably A
<220> FEATURE:
<221> NAME/KEY: MISC_FEATURE
<222> LOCATION: (5)..(5)
<223> OTHER INFORMATION: is selected from the group consisting of F, Y,
      and W, and is preferably Y
<220> FEATURE:
<221> NAME/KEY: MISC_FEATURE
<222> LOCATION: (6)..(6)
<223> OTHER INFORMATION: is selected from the group consisting of A, D,
      E, N, and Q, is preferably E or Q, and is more preferably E
<220> FEATURE:
<221> NAME/KEY: MISC_FEATURE
<222> LOCATION: (7)..(7)
<223> OTHER INFORMATION: is any amino acid, preferably selected from the
      group consisting of A, D, E, N, and K, and is more preferably E
<220> FEATURE:
<221> NAME/KEY: MISC_FEATURE
<222> LOCATION: (8)..(8)
<223> OTHER INFORMATION: is selected from the group consisting of S or
      T, and is preferably S
<220> FEATURE:
<221> NAME/KEY: MISC_FEATURE
<222> LOCATION: (9)..(9)
<223> OTHER INFORMATION: is any amino acid

<400> SEQUENCE: 15

Xaa Xaa Xaa Xaa Xaa Xaa Xaa Xaa Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: Consensus sequence of penton base proteins
<220> FEATURE:
<221> NAME/KEY: MISC_FEATURE
<222> LOCATION: (1)..(1)
<223> OTHER INFORMATION: is any amino acid
<220> FEATURE:
<221> NAME/KEY: MISC_FEATURE
<222> LOCATION: (2)..(2)
<223> OTHER INFORMATION: is R
<220> FEATURE:
<221> NAME/KEY: MISC_FEATURE
<222> LOCATION: (3)..(3)
<223> OTHER INFORMATION: is G
<220> FEATURE:
<221> NAME/KEY: MISC_FEATURE
<222> LOCATION: (4)..(4)
<223> OTHER INFORMATION: is D
<220> FEATURE:
<221> NAME/KEY: MISC_FEATURE
<222> LOCATION: (5)..(5)
```

```
<223> OTHER INFORMATION: is any amino acid

<400> SEQUENCE: 16

Xaa Xaa Xaa Xaa Xaa
1               5

<210> SEQ ID NO 17
<211> LENGTH: 8
<212> TYPE: PRT
<213> ORGANISM: Artificial Sequence
<220> FEATURE:
<223> OTHER INFORMATION: Consensus sequence of penton base proteins
<220> FEATURE:
<221> NAME/KEY: MISC_FEATURE
<222> LOCATION: (1)..(1)
<223> OTHER INFORMATION: is any amino acid
<220> FEATURE:
<221> NAME/KEY: MISC_FEATURE
<222> LOCATION: (2)..(2)
<223> OTHER INFORMATION: is selected from the group consisting of I, L
      and V, and is preferably I
<220> FEATURE:
<221> NAME/KEY: MISC_FEATURE
<222> LOCATION: (3)..(3)
<223> OTHER INFORMATION: is selected from the group consisting of D, E,
      K, N, Q, and V, is preferably Q or K, and is more preferably Q
<220> FEATURE:
<221> NAME/KEY: MISC_FEATURE
<222> LOCATION: (4)..(4)
<223> OTHER INFORMATION: is selected from the group consisting of C, G
      and P, and is preferably P
<220> FEATURE:
<221> NAME/KEY: MISC_FEATURE
<222> LOCATION: (5)..(5)
<223> OTHER INFORMATION: is selected from the group consisting of I, L
      and V, is preferably L or V and is more preferably L
<220> FEATURE:
<221> NAME/KEY: MISC_FEATURE
<222> LOCATION: (6)..(6)
<223> OTHER INFORMATION: is selected from the group consisting of D, E,
      S and T, is preferably E or T and is more preferably E
<220> FEATURE:
<221> NAME/KEY: MISC_FEATURE
<222> LOCATION: (7)..(7)
<223> OTHER INFORMATION: is selected from the group consisting of D, E,
      K, S and T, is preferably E, K or T, and is more preferably K
<220> FEATURE:
<221> NAME/KEY: MISC_FEATURE
<222> LOCATION: (8)..(8)
<223> OTHER INFORMATION: is selected from the group consisting of D and
      E, and is preferably D

<400> SEQUENCE: 17

Xaa Xaa Xaa Xaa Xaa Xaa Xaa Xaa
1               5

<210> SEQ ID NO 18
<211> LENGTH: 8
<212> TYPE: PRT
<213> ORGANISM: Artificial Sequence
<220> FEATURE:
<223> OTHER INFORMATION: Consensus sequence of penton base proteins
<220> FEATURE:
<221> NAME/KEY: MISC_FEATURE
<222> LOCATION: (1)..(1)
<223> OTHER INFORMATION: is selected from the group consisting of F, Y,
      and W, and is preferably F
<220> FEATURE:
<221> NAME/KEY: MISC_FEATURE
<222> LOCATION: (2)..(2)
<223> OTHER INFORMATION: is selected from the group consisting of H, K
      and R, and is preferably K
<220> FEATURE:
<221> NAME/KEY: MISC_FEATURE
<222> LOCATION: (3)..(3)
```

```
<223> OTHER INFORMATION: is selected from the group consisting of A, V,
      I, and L, and is preferably A
<220> FEATURE:
<221> NAME/KEY: MISC_FEATURE
<222> LOCATION: (4)..(4)
<223> OTHER INFORMATION: is selected from the group consisting of H, K,
      and R, and is preferably R
<220> FEATURE:
<221> NAME/KEY: MISC_FEATURE
<222> LOCATION: (5)..(5)
<223> OTHER INFORMATION: is selected from the group consisting of A, V,
      I, and L, and is preferably V
<220> FEATURE:
<221> NAME/KEY: MISC_FEATURE
<222> LOCATION: (6)..(6)
<223> OTHER INFORMATION: is selected from the group consisting of A, V,
      I, L and M, and is preferably M
<220> FEATURE:
<221> NAME/KEY: MISC_FEATURE
<222> LOCATION: (7)..(7)
<223> OTHER INFORMATION: is selected from the group consisting of A, V,
      I, and L, and is preferably V
<220> FEATURE:
<221> NAME/KEY: MISC_FEATURE
<222> LOCATION: (8)..(8)
<223> OTHER INFORMATION: is any amino acid

<400> SEQUENCE: 18

Xaa Xaa Xaa Xaa Xaa Xaa Xaa Xaa
1               5

<210> SEQ ID NO 19
<211> LENGTH: 7
<212> TYPE: PRT
<213> ORGANISM: Artificial Sequence
<220> FEATURE:
<223> OTHER INFORMATION: Consensus sequence of penton base proteins
<220> FEATURE:
<221> NAME/KEY: MISC_FEATURE
<222> LOCATION: (1)..(1)
<223> OTHER INFORMATION: is any amino acid
<220> FEATURE:
<221> NAME/KEY: MISC_FEATURE
<222> LOCATION: (2)..(2)
<223> OTHER INFORMATION: is selected from the group consisting of F, Y,
      and W, and is preferably Y
<220> FEATURE:
<221> NAME/KEY: MISC_FEATURE
<222> LOCATION: (3)..(3)
<223> OTHER INFORMATION: is selected from the group consisting of D, E,
      S and T, is preferably E or T and is more preferably E
<220> FEATURE:
<221> NAME/KEY: MISC_FEATURE
<222> LOCATION: (4)..(4)
<223> OTHER INFORMATION: is selected from the group consisting of F, Y,
      and W, and is preferably W
<220> FEATURE:
<221> NAME/KEY: MISC_FEATURE
<222> LOCATION: (5)..(5)
<223> OTHER INFORMATION: is selected from the group consisting of A, F,
      V, Y, and W, is preferably F or V and is more preferably F
<220> FEATURE:
<221> NAME/KEY: MISC_FEATURE
<222> LOCATION: (6)..(6)
<223> OTHER INFORMATION: is selected from the group consisting of D, E,
      S and T, is preferably D or E and is more preferably E
<220> FEATURE:
<221> NAME/KEY: MISC_FEATURE
<222> LOCATION: (7)..(7)
<223> OTHER INFORMATION: is selected from the group consisting of F, Y,
      and W, and is preferably F

<400> SEQUENCE: 19

Xaa Xaa Xaa Xaa Xaa Xaa Xaa
1               5
```

```
<210> SEQ ID NO 20
<211> LENGTH: 26
<212> TYPE: PRT
<213> ORGANISM: Artificial Sequence
<220> FEATURE:
<223> OTHER INFORMATION: Consensus sequence of peton base proteins
<220> FEATURE:
<221> NAME/KEY: MISC_FEATURE
<222> LOCATION: (11)..(11)
<223> OTHER INFORMATION: Xaa is selected from the group consisting of V,
      I, and L
<220> FEATURE:
<221> NAME/KEY: MISC_FEATURE
<222> LOCATION: (12)..(12)
<223> OTHER INFORMATION: Xaa is selected from the group consisting of E,
      and D
<220> FEATURE:
<221> NAME/KEY: MISC_FEATURE
<222> LOCATION: (13)..(13)
<223> OTHER INFORMATION: Xaa is selected from the group consisting of H,
      N and Q
<220> FEATURE:
<221> NAME/KEY: MISC_FEATURE
<222> LOCATION: (16)..(16)
<223> OTHER INFORMATION: Xaa is selected from the group consisting of K,
      E, R, Q, and A
<220> FEATURE:
<221> NAME/KEY: MISC_FEATURE
<222> LOCATION: (17)..(17)
<223> OTHER INFORMATION: Xaa is selected from the group consisting of V,
      L, and I
<220> FEATURE:
<221> NAME/KEY: MISC_FEATURE
<222> LOCATION: (21)..(21)
<223> OTHER INFORMATION: Xaa is selected from the group consisting of H,
      N and Q

<400> SEQUENCE: 20

Met Thr Ile Asp Leu Met Asn Asn Ala Ile Xaa Xaa Xaa Tyr Leu Xaa
1               5                   10                  15

Xaa Gly Arg Gln Xaa Gly Val Leu Glu Ser
            20                  25

<210> SEQ ID NO 21
<211> LENGTH: 8
<212> TYPE: PRT
<213> ORGANISM: Adenovirus

<400> SEQUENCE: 21

Asp Val Thr Ala Tyr Glu Glu Ser
1               5

<210> SEQ ID NO 22
<211> LENGTH: 8
<212> TYPE: PRT
<213> ORGANISM: Adenovirus

<400> SEQUENCE: 22

Asp Val Asp Ala Tyr Glu Asn Ser
1               5

<210> SEQ ID NO 23
<211> LENGTH: 8
<212> TYPE: PRT
<213> ORGANISM: Adenovirus

<400> SEQUENCE: 23

Asp Val Ala Glu Tyr Glu Lys Ser
1               5
```

<210> SEQ ID NO 24
<211> LENGTH: 8
<212> TYPE: PRT
<213> ORGANISM: Adenovirus

<400> SEQUENCE: 24

Asp Val Glu Ala Tyr Glu Lys Ser
1               5

<210> SEQ ID NO 25
<211> LENGTH: 8
<212> TYPE: PRT
<213> ORGANISM: Adenovirus

<400> SEQUENCE: 25

Asp Val Asp Ala Tyr Glu Lys Ser
1               5

<210> SEQ ID NO 26
<211> LENGTH: 8
<212> TYPE: PRT
<213> ORGANISM: Adenovirus

<400> SEQUENCE: 26

Asp Val Ser Lys Tyr Glu Ala Ser
1               5

<210> SEQ ID NO 27
<211> LENGTH: 8
<212> TYPE: PRT
<213> ORGANISM: Adenovirus

<400> SEQUENCE: 27

Asn Val Lys Ala Tyr Glu Asp Ser
1               5

<210> SEQ ID NO 28
<211> LENGTH: 8
<212> TYPE: PRT
<213> ORGANISM: Adenovirus

<400> SEQUENCE: 28

Asp Val Lys Lys Tyr Glu Asn Ser
1               5

<210> SEQ ID NO 29
<211> LENGTH: 8
<212> TYPE: PRT
<213> ORGANISM: Adenovirus

<400> SEQUENCE: 29

Asp Val Asp Ala Tyr Gln Ala Ser
1               5

<210> SEQ ID NO 30
<211> LENGTH: 8
<212> TYPE: PRT
<213> ORGANISM: Adenovirus

<400> SEQUENCE: 30

Asp Val Asp Ala Tyr Gln Ala Ser
1               5

<210> SEQ ID NO 31

```
<211> LENGTH: 7
<212> TYPE: PRT
<213> ORGANISM: Adenovirus

<400> SEQUENCE: 31

Ile Gln Pro Leu Glu Lys Asp
1               5

<210> SEQ ID NO 32
<211> LENGTH: 7
<212> TYPE: PRT
<213> ORGANISM: Adenovirus

<400> SEQUENCE: 32

Ile Gln Pro Val Glu Lys Asp
1               5

<210> SEQ ID NO 33
<211> LENGTH: 7
<212> TYPE: PRT
<213> ORGANISM: Adenovirus

<400> SEQUENCE: 33

Ile Lys Pro Leu Glu Lys Asp
1               5

<210> SEQ ID NO 34
<211> LENGTH: 7
<212> TYPE: PRT
<213> ORGANISM: Adenovirus

<400> SEQUENCE: 34

Ile Val Pro Leu Thr Lys Asp
1               5

<210> SEQ ID NO 35
<211> LENGTH: 7
<212> TYPE: PRT
<213> ORGANISM: Adenovirus

<400> SEQUENCE: 35

Ile Glu Pro Val Glu Thr Asp
1               5

<210> SEQ ID NO 36
<211> LENGTH: 7
<212> TYPE: PRT
<213> ORGANISM: Adenovirus

<400> SEQUENCE: 36

Ile Lys Pro Leu Thr Glu Asp
1               5

<210> SEQ ID NO 37
<211> LENGTH: 7
<212> TYPE: PRT
<213> ORGANISM: Adenovirus

<400> SEQUENCE: 37

Phe Lys Ala Arg Val Met Val
1               5

<210> SEQ ID NO 38
<211> LENGTH: 7
<212> TYPE: PRT
```

```
<213> ORGANISM: Adenovirus

<400> SEQUENCE: 38

Phe Arg Ala Lys Leu Met Val
1               5

<210> SEQ ID NO 39
<211> LENGTH: 7
<212> TYPE: PRT
<213> ORGANISM: Adenovirus

<400> SEQUENCE: 39

Phe Arg Ala Lys Val Met Val
1               5

<210> SEQ ID NO 40
<211> LENGTH: 6
<212> TYPE: PRT
<213> ORGANISM: Adenovirus

<400> SEQUENCE: 40

Tyr Glu Trp Phe Glu Phe
1               5

<210> SEQ ID NO 41
<211> LENGTH: 6
<212> TYPE: PRT
<213> ORGANISM: Adenovirus

<400> SEQUENCE: 41

Tyr Glu Trp Val Glu Phe
1               5

<210> SEQ ID NO 42
<211> LENGTH: 6
<212> TYPE: PRT
<213> ORGANISM: Adenovirus

<400> SEQUENCE: 42

Tyr Glu Trp Ala Glu Phe
1               5

<210> SEQ ID NO 43
<211> LENGTH: 9
<212> TYPE: PRT
<213> ORGANISM: Artificial Sequence
<220> FEATURE:
<223> OTHER INFORMATION: Adenovirus fibre protein consensus sequence
<220> FEATURE:
<221> NAME/KEY: MISC_FEATURE
<222> LOCATION: (1)..(1)
<223> OTHER INFORMATION: is selected from the group consisting of S, D
      and T, preferably S or D, and is more preferably S
<220> FEATURE:
<221> NAME/KEY: MISC_FEATURE
<222> LOCATION: (9)..(9)
<223> OTHER INFORMATION: is selected from the group consisting of E, D
      and G, is preferably E or D, and is more preferably E

<400> SEQUENCE: 43

Xaa Phe Asn Pro Val Tyr Pro Tyr Xaa
1               5

<210> SEQ ID NO 44
<211> LENGTH: 7
<212> TYPE: PRT
<213> ORGANISM: Artificial Sequence
```

```
<220> FEATURE:
<223> OTHER INFORMATION: Consensus sequence of the N-terminus of the
      N-terminal domain
<220> FEATURE:
<221> NAME/KEY: MISC_FEATURE
<222> LOCATION: (1)..(1)
<223> OTHER INFORMATION: Xaa is selected from the group consisting of G
      and E

<400> SEQUENCE: 44

Xaa Gly Arg Asn Ser Ile Arg
1               5

<210> SEQ ID NO 45
<211> LENGTH: 6
<212> TYPE: PRT
<213> ORGANISM: Artificial Sequence
<220> FEATURE:
<223> OTHER INFORMATION: C-terminalconsensus sequence of the N-terminal
      domain
<220> FEATURE:
<221> NAME/KEY: MISC_FEATURE
<222> LOCATION: (2)..(2)
<223> OTHER INFORMATION: Xaa is selected from the group consisting of D
      and E

<400> SEQUENCE: 45

Asp Xaa Arg Ser Arg Gly
1               5

<210> SEQ ID NO 46
<211> LENGTH: 9
<212> TYPE: PRT
<213> ORGANISM: Artificial Sequence
<220> FEATURE:
<223> OTHER INFORMATION: Part of the conformational epitope forming the
      fibre binding cleft of the penton base protomer
<220> FEATURE:
<221> NAME/KEY: MISC_FEATURE
<222> LOCATION: (4)..(4)
<223> OTHER INFORMATION: Xaa is selected from the group consisting of V,
      I, L, E, or D
<220> FEATURE:
<221> NAME/KEY: MISC_FEATURE
<222> LOCATION: (6)..(6)
<223> OTHER INFORMATION: Xaa is selected from the group consisting of V,
      L, and I
<220> FEATURE:
<221> NAME/KEY: MISC_FEATURE
<222> LOCATION: (7)..(7)
<223> OTHER INFORMATION: Xaa  is selected from the group consisting of
      M, T and S

<400> SEQUENCE: 46

Trp Asp Pro Xaa Thr Xaa Xaa Pro Gly
1               5

<210> SEQ ID NO 47
<211> LENGTH: 7
<212> TYPE: PRT
<213> ORGANISM: Artificial Sequence
<220> FEATURE:
<223> OTHER INFORMATION: Part of the conformational epitope forming the
      fibre binding cleft of the penton base protomer
<220> FEATURE:
<221> NAME/KEY: MISC_FEATURE
<222> LOCATION: (1)..(1)
<223> OTHER INFORMATION: Xaa is selected from the group consisting of D,
      E, N, and Q
<220> FEATURE:
<221> NAME/KEY: MISC_FEATURE
<222> LOCATION: (3)..(3)
<223> OTHER INFORMATION: Xaai s any amino acid, preferably selected from
```

```
         the group consisting of A, D, P, K and T
<220> FEATURE:
<221> NAME/KEY: MISC_FEATURE
<222> LOCATION: (4)..(4)
<223> OTHER INFORMATION: Xaa is selected from the group consisting of A,
      D, E, K and R
<220> FEATURE:
<221> NAME/KEY: MISC_FEATURE
<222> LOCATION: (6)..(6)
<223> OTHER INFORMATION: Xaa is selected from the group consisting of D,
      E, L, I, Q, and N
<220> FEATURE:
<221> NAME/KEY: MISC_FEATURE
<222> LOCATION: (7)..(7)
<223> OTHER INFORMATION: Xaa is selected from the group consisting of A,
      D, E, K, N, Q, and R

<400> SEQUENCE: 47

Xaa Val Xaa Xaa Tyr Xaa Xaa
1               5

<210> SEQ ID NO 48
<211> LENGTH: 5
<212> TYPE: PRT
<213> ORGANISM: Artificial Sequence
<220> FEATURE:
<223> OTHER INFORMATION: Part of the conformational epitope forming the
      fibre binding cleft of the penton base protomer
<220> FEATURE:
<221> NAME/KEY: MISC_FEATURE
<222> LOCATION: (1)..(1)
<223> OTHER INFORMATION: Xaa is selected from the group consisting of K,
      R, S, and T
<220> FEATURE:
<221> NAME/KEY: MISC_FEATURE
<222> LOCATION: (2)..(2)
<223> OTHER INFORMATION: Xaa is selected from the group consisting of A,
      D, E, G, K, N, Q, R, S, and T

<400> SEQUENCE: 48

Xaa Xaa Arg Ser Tyr
1               5

<210> SEQ ID NO 49
<211> LENGTH: 10
<212> TYPE: PRT
<213> ORGANISM: Artificial Sequence
<220> FEATURE:
<223> OTHER INFORMATION: Part of the conformational epitope forming the
      fibre binding cleft of the penton base protomer
<220> FEATURE:
<221> NAME/KEY: MISC_FEATURE
<222> LOCATION: (3)..(3)
<223> OTHER INFORMATION: Xaa is selected from the group consisting of H,
      K, and R
<220> FEATURE:
<221> NAME/KEY: MISC_FEATURE
<222> LOCATION: (10)..(10)
<223> OTHER INFORMATION: Xaa is selected from the group consisting of D
      and E

<400> SEQUENCE: 49

Leu Thr Xaa Val Phe Asn Arg Phe Pro Xaa
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Consensus sequence of N-terminal domain
      comprising coupling residues
<220> FEATURE:
```

```
<221> NAME/KEY: MISC_FEATURE
<222> LOCATION: (3)..(3)
<223> OTHER INFORMATION: Xaa is selected from the group consisting of G
      and E
<220> FEATURE:
<221> NAME/KEY: MISC_FEATURE
<222> LOCATION: (4)..(4)
<223> OTHER INFORMATION: Xaa is a coupling residue, preferably C; D, E,
      and K, most preferably C
<220> FEATURE:
<221> NAME/KEY: MISC_FEATURE
<222> LOCATION: (7)..(7)
<223> OTHER INFORMATION: Xaa is a coupling residue, preferably C; D, E,
      and K, most preferably C

<400> SEQUENCE: 50

Pro Thr Xaa Xaa Arg Asn Xaa Ile Arg
1               5

<210> SEQ ID NO 51
<211> LENGTH: 9
<212> TYPE: PRT
<213> ORGANISM: Artificial Sequence
<220> FEATURE:
<223> OTHER INFORMATION: Consensus sequence of N-terminal domain
      comprising coupling residues
<220> FEATURE:
<221> NAME/KEY: MISC_FEATURE
<222> LOCATION: (3)..(3)
<223> OTHER INFORMATION: Xaa is selected from the group consisting of G
      and E
<220> FEATURE:
<221> NAME/KEY: MISC_FEATURE
<222> LOCATION: (6)..(6)
<223> OTHER INFORMATION: Xaa is a coupling residue, preferably C; D, E,
      and K, most preferably C

<400> SEQUENCE: 51

Pro Thr Xaa Gly Arg Xaa Ser Ile Arg
1               5

<210> SEQ ID NO 52
<211> LENGTH: 8
<212> TYPE: PRT
<213> ORGANISM: Artificial Sequence
<220> FEATURE:
<223> OTHER INFORMATION: Consensus sequence of N-terminal domain
      comprising coupling residues
<220> FEATURE:
<221> NAME/KEY: MISC_FEATURE
<222> LOCATION: (6)..(6)
<223> OTHER INFORMATION: Xaa is selected from the group consisting of D
      and E
<220> FEATURE:
<221> NAME/KEY: MISC_FEATURE
<222> LOCATION: (7)..(7)
<223> OTHER INFORMATION: Xaa is a coupling residue, preferably C; D, E,
      and K, most preferably C
<220> FEATURE:
<221> NAME/KEY: MISC_FEATURE
<222> LOCATION: (8)..(8)
<223> OTHER INFORMATION: Xaa is selected from the group consisting of I,
      L and V

<400> SEQUENCE: 52

Thr Gln Thr Ile Asn Xaa Xaa Xaa
1               5

<210> SEQ ID NO 53
<211> LENGTH: 9
<212> TYPE: PRT
<213> ORGANISM: Artificial Sequence
<220> FEATURE:
```

```
<223> OTHER INFORMATION: Consensus sequence of N-terminal domain
      comprising coupling residues
<220> FEATURE:
<221> NAME/KEY: MISC_FEATURE
<222> LOCATION: (3)..(3)
<223> OTHER INFORMATION: Xaa is selected from the group consisting of G
      and E
<220> FEATURE:
<221> NAME/KEY: MISC_FEATURE
<222> LOCATION: (7)..(7)
<223> OTHER INFORMATION: Xaa is a coupling residue, preferably C; D, E,
      and K, most preferably C

<400> SEQUENCE: 53

Pro Thr Xaa Gly Arg Asn Xaa Ile Arg
1               5

<210> SEQ ID NO 54
<211> LENGTH: 10
<212> TYPE: PRT
<213> ORGANISM: Artificial Sequence
<220> FEATURE:
<223> OTHER INFORMATION: Consenus sequence for the locaion of a coupling
      residue in the C-terminal end of the penton base protomer
<220> FEATURE:
<221> NAME/KEY: MISC_FEATURE
<222> LOCATION: (4)..(4)
<223> OTHER INFORMATION: Xaa is a coupling residue, preferably C; D, E,
      and K, most preferably C
<220> FEATURE:
<221> NAME/KEY: MISC_FEATURE
<222> LOCATION: (6)..(6)
<223> OTHER INFORMATION: Xaa is selected from the group consisting of H
      and Y

<400> SEQUENCE: 54

Thr Cys Pro Xaa Val Xaa Lys Ala Leu Gly
1               5                   10

<210> SEQ ID NO 55
<211> LENGTH: 17
<212> TYPE: PRT
<213> ORGANISM: Dengue virus

<400> SEQUENCE: 55

His Ala Lys Lys Gln Asp Val Val Val Leu Gly Ser Gln Glu Gly Ala
1               5                   10                  15

Met

<210> SEQ ID NO 56
<211> LENGTH: 18
<212> TYPE: PRT
<213> ORGANISM: Chikungunya virus

<400> SEQUENCE: 56

Ser Thr Lys Asp Asn Phe Asn Val Tyr Lys Ala Thr Arg Pro Tyr Leu
1               5                   10                  15

Ala His

<210> SEQ ID NO 57
<211> LENGTH: 17
<212> TYPE: PRT
<213> ORGANISM: Zika virus

<400> SEQUENCE: 57

Ser Thr Lys Asp Asn Phe Asn Val Tyr Lys Ala Thr Arg Pro Leu Ala
1               5                   10                  15
```

His

<210> SEQ ID NO 58
<211> LENGTH: 37
<212> TYPE: PRT
<213> ORGANISM: Artificial Sequence
<220> FEATURE:
<223> OTHER INFORMATION: Fusion protein of Chikungunya antigenic peptide
      and STICKER

<400> SEQUENCE: 58

Ala Lys Arg Ala Arg Leu Ser Thr Ser Phe Asn Pro Val Pro Tyr Glu
1               5                   10                  15

Asp Glu Ser Ser Thr Lys Asp Asn Phe Asn Val Tyr Lys Ala Thr Arg
            20                  25                  30

Pro Tyr Leu Ala His
        35

<210> SEQ ID NO 59
<211> LENGTH: 38
<212> TYPE: PRT
<213> ORGANISM: Artificial Sequence
<220> FEATURE:
<223> OTHER INFORMATION: Fusion protein of STICKER with coupling residue
      and Chinkungunya virus antigenic peptide

<400> SEQUENCE: 59

Ala Lys Arg Ala Arg Leu Ser Thr Ser Phe Asn Pro Val Pro Tyr Glu
1               5                   10                  15

Asp Glu Cys Ser Ser Thr Lys Asp Asn Phe Asn Val Tyr Lys Ala Thr
            20                  25                  30

Arg Pro Tyr Leu Ala His
        35

<210> SEQ ID NO 60
<211> LENGTH: 37
<212> TYPE: PRT
<213> ORGANISM: Artificial Sequence
<220> FEATURE:
<223> OTHER INFORMATION: Fusion protein of STICKER with coupling residue
      and Chinkungunya virus antigenic peptide

<400> SEQUENCE: 60

Ala Lys Arg Ala Arg Leu Ser Thr Cys Phe Asn Pro Val Pro Tyr Glu
1               5                   10                  15

Asp Glu Ser Ser Thr Lys Asp Asn Phe Asn Val Tyr Lys Ala Thr Arg
            20                  25                  30

Pro Tyr Leu Ala His
        35

<210> SEQ ID NO 61
<211> LENGTH: 4453
<212> TYPE: DNA
<213> ORGANISM: Artificial Sequence
<220> FEATURE:
<223> OTHER INFORMATION: Cloning vector pACEBac-ADDomer1.0 plasmid
      sequence

<400> SEQUENCE: 61
accggttgac ttgggtcaac tgtcagacca agtttactca tatatacttt agattgattt      60
aaaacttcat ttttaattta aaaggatcta ggtgaagatc cttttgata atctcatgac     120 caaaatccct taacgtgagt tttcgttcca ctgagcgtca gaccccgtag aaaagatcaa    180

```
aggatcttct tgagatccstt tttttctgcg cgtaatctgc tgcttgcaaa caaaaaaacc    240
accgctacca gcggtggttt gtttgccgga tcaagagcta ccaactcttt ttccgaaggt    300
aactggcttc agcagagcgc agataccaaa tactgttctt ctagtgtagc cgtagttagg    360
ccaccacttc aagaactctg tagcaccgcc tacataccsc gctctgctaa tcctgttacc    420
agtggctgct gccagtggcg ataagtcgtg tcttaccggg ttggactcaa gacgatagtt    480
accggataag gcgcagcggt cgggctgaac gggggggttcg tgcacacagc ccagcttgga    540
gcgaacgacc tacaccgaac tgagatacct acagcgtgag ctatgagaaa gcgccacgct    600
tcccgaaggg agaaaggcgg acaggtatcc ggtaagcggc agggtcggaa caggagagcg    660
cacgagggag cttccagggg gaaacgcctg gtatctttat agtcctgtcg ggtttcgcca    720
cctctgactt gagcgtcgat ttttgtgatg ctcgtcaggg gggcggagcc tatgaaaaaa    780
cgccagcaac gcggccttt tacggttcct ggccttttgc tggccttttg ctcacatgtt    840
ctttcctgcg ttatccsctg attgacttgg gtcgctcttc ctgtggatgc gcagatgccc    900
tgcgtaagcg ggtgtgggcg gacaataaag tcttaaactg aacaaaatag atctaaacta    960
tgacaataaa gtcttaaact agacagaata gttgtaaact gaaatcagtc cagttatgct   1020 gtgaaaagc atactggact tttgttatgg ctaaagcaaa ctcttcattt tctgaagtgc   1080
aaattgcccg tcgtattaaa gaggggcgtg gccaagggca tgtaaagact atattcgcgg   1140
cgttgtgaca atttaccgaa caactccgcg gccgggaagc cgatctcggc ttgaacgaat   1200
tgttaggtgg cggtacttgg gtcgatatca aagtgcatca cttcttcccg tatgcccaac   1260
tttgtataga gagccactgc gggatcgtca ccgtaatctg cttgcacgta gatcacataa   1320
gcaccaagcg cgttggcctc atgcttgagg agattgatga gcgcggtggc aatgccctgc   1380
ctccggtgct cgccggagac tgcgagatca tagatataga tctcactacg cggctgctca   1440
aacttgggca gaacgtaagc cgcgagagcg ccaacaaccg cttcttggtc gaaggcagca   1500
agcgcgatga atgtcttact acggagcaag ttcccgaggt aatcggagtc cggctgatgt   1560
tgggagtagg tggctacgtc tccgaactca cgaccgaaaa gatcaagagc agcccgcatg   1620
gatttgactt ggtcagggcc gagcctacat gtgcgaatga tgcccatact tgagccacct   1680
aactttgttt tagggcgact gccctgctgc gtaacatcgt tgctgctgcg taacatcgtt   1740
gctgctccat aacatcaaac atcgacccac ggcgtaacgc gcttgctgct tggatgcccg   1800
aggcatagac tgtacaaaaa aacagtcata acaagccatg aaaaccgcca ctgcgccgtt   1860
accaccgctg cgttcggtca aggttctgga ccagttgcgt gagcgcatac gctacttgca   1920
ttacagttta cgaaccgaac aggcttatgt caactgggtt cgtgccttca tccgtttcca   1980
cggtgtgcgt cacccggcaa ccttgggcag cagcgaagtc gccataactt cgtatagcat   2040
acattatacg aagttatctg taactataac ggtcctaagg tagcgagttt aaacactagt   2100
atcgattcgc gacctactcc ggaatattaa tagatcatgg agataattaa aatgataacc   2160
atctcgcaaa taaataagta ttttactgtt ttcgtaacag ttttgtaata aaaaaaccta   2220
taaatattcc ggattattca taccgtccca ccatcgggcg cggatccatg aggagacgag   2280
ccgtgctagg cggagcggtg gtgtatccgg agggtcctcc tccttcttac gagagcgtga   2340
tgcagcaaca ggcggcgatg atacagcccc cactggaggc tcccttcgta ccccacggt   2400 acctggcgcc tacggaaggg agaaacagca ttcgttactc ggagctgtcg cccctgtacg   2460
ataccaccaa gttgtatctg gtggacaaca agtcggcgga catcgcctcc ctgaactatc   2520
agaacgacca cagcaacttc ctgaccacgg tggtgcagaa caatgacttt acccccacgg   2580
```

```
aggctagcac ccagaccatc aactttgacg agcggtcgcg atggggcggt cagctgaaga   2640
ccatcatgca caccaacatg cccaacgtga acgagtacac gttcagcaac aagttcaagg   2700
cgagggtgat ggtgtccaga aaagctcctg aaggtgttac agtaaatgac acctatgatc   2760
ataaagagga tatcttgaag tatgagtggt ttgagttcat tttaccagaa ggcaactttt   2820
cagccaccat gacgatcgac ctgatgaaca atgccatcat tgacaactac ctggaaattg   2880
gcagacagaa tggagtgctg gaaagtgaca ttggtgttaa gtttgacact agaaatttca   2940
ggctcgggtg ggaccccgaa actaagttga ttatgccagg tgtctacact tatgaggcat   3000
tccatcctga cattgtattg ctgcctggtt gcggggtaga ctttactgaa gccgactta   3060 gcaacttgct tggcatcagg aagagacatc cattccagga gggtttcaaa atcatgtatg   3120
aagatcttga aggggtaat attcctgccc ttttggatgt cactgcctat gaggaaagca   3180
aaaaggatac cactactgaa acaaccacac tggctgttgc agaggaaact agtgaagatg   3240
atgatataac tagaggagat acctatataa ctgaaaaaca aaaacgtgaa gctgcagctg   3300
ctgaagttaa aaaagagtta aagatccaac ctctagaaaa agacagcaag agtagaagct   3360
acaatgtctt ggaagacaaa atcaacacag cctaccgcag ttggtacctg tcctacaatt   3420
acggtaaccc tgagaaagga ataaggtctt ggacactgct caccacttca gatgtcacct   3480
gtggggcaga gcaggtctac tggtcgctcc ctgacatgat gcaagaccca gtcaccttcc   3540
gctccacaag acaagtcaac aactacccag tggtgggtgc agagcttatg cccgtcttct   3600
caaagagttt ctacaatgag caagccgtgt actctcagca gctccgacag gccacttcgc   3660
tcacgcacgt cttcaaccgc ttccctgaga accagatcct catccgcccg ccggcgccca   3720
caattaccac cgtcagtgaa aacgttcctg ctctcacaga tcacgggacc ctgccgttac   3780
gcagcagtat ccggggagtc cagcgcgtga ccgttactga cgccagacgc cgcacctgtc   3840
cctacgttta caaggccctg gcatagtcg cgccgcgcgt tctttcaagc cgcactttct   3900
gataagcttg tcgagaagta ctagaggatc ataatcagcc ataccacatt tgtagaggtt   3960
ttacttgctt taaaaaacct cccacacctc cccctgaacc tgaaacataa aatgaatgca   4020
attgttgttg ttaacttgtt tattgcagct tataatggtt acaaataaag caatagcatc   4080
acaaatttca caaataaagc atttttttca ctgcattcta gttgtggttt gtccaaactc   4140
atcaatgtat cttatcatgt ctggatctga tcactgcttg agcctagaag atccggctgc   4200
taacaaagcc cgaaaggaag ctgagttggc tgctgccacc gctgagcaat aactatcata   4260 accctaggg tatacccatc taattggaac cagataagtg aaatctagtt ccaaactatt   4320
ttgtcatttt taattttcgt attagcttac gacgctacac ccagttccca tctattttgt   4380
cactcttccc taaataatcc ttaaaaactc catttccacc cctcccagtt cccaactatt   4440
ttgtccgccc aca                                                     4453

<210> SEQ ID NO 62
<211> LENGTH: 4614
<212> TYPE: DNA
<213> ORGANISM: Artificial Sequence
<220> FEATURE:
<223> OTHER INFORMATION: Cloning vector pACEBac-ADDOMER2.0 plasmid
      sequence

<400> SEQUENCE: 62
accggttgac ttgggtcaac tgtcagacca agtttactca tatatacttt agattgattt     60
aaaacttcat ttttaattta aaaggatcta ggtgaagatc cttttttgata atctcatgac    120
```

```
caaaatccct taacgtgagt tttcgttcca ctgagcgtca gacccgtag aaaagatcaa     180 aggatcttct tgagatcctt tttttctgcg cgtaatctgc tgcttgcaaa caaaaaaacc    240
accgctacca gcggtggttt gtttgccgga tcaagagcta ccaactcttt ttccgaaggt    300
aactggcttc agcagagcgc agataccaaa tactgttctt ctagtgtagc cgtagttagg    360
ccaccacttc aagaactctg tagcaccgcc tacatacctc gctctgctaa tcctgttacc    420
agtggctgct gccagtggcg ataagtcgtg tcttaccggg ttggactcaa gacgatagtt    480
accggataag gcgcagcggt cgggctgaac gggggggttcg tgcacacagc ccagcttgga   540
gcgaacgacc tacaccgaac tgagatacct acagcgtgag ctatgagaaa gcgccacgct    600
tcccgaaggg agaaaggcgg acaggtatcc ggtaagcggc agggtcggaa caggagagcg    660
cacgagggag cttccagggg gaaacgcctg gtatctttat agtcctgtcg ggtttcgcca    720
cctctgactt gagcgtcgat ttttgtgatg ctcgtcaggg gggcggagcc tatggaaaaa    780
cgccagcaac gcggccttt tacggttcct ggccttttgc tggccttttg ctcacatgtt     840
ctttcctgcg ttatccctg attgacttgg gtcgctcttc ctgtggatgc gcagatgccc     900
tgcgtaagcg ggtgtgggcg gacaataaag tcttaaactg aacaaaatag atctaaacta    960
tgacaataaa gtcttaaact agacagaata gttgtaaact gaaatcagtc cagttatgct    1020 gtgaaaagc atactggact tttgttatgg ctaaagcaaa ctcttcattt tctgaagtgc     1080
aaattgcccg tcgtattaaa gaggggcgtg gccaagggca tgtaaagact atattcgcgg    1140
cgttgtgaca atttaccgaa caactccgcg gccgggaagc cgatctcggc ttgaacgaat    1200
tgttaggtgg cggtacttgg gtcgatatca aagtgcatca cttcttcccg tatgcccaac    1260
tttgtataga gagccactgc gggatcgtca ccgtaatctg cttgcacgta gatcacataa    1320
gcaccaagcg cgttggcctc atgcttgagg agattgatga gcgcggtggc aatgccctgc    1380
ctccggtgct cgccggagac tgcgagatca tagatataga tctcactacg cggctgctca    1440
aacttgggca gaacgtaagc cgcgagagcg ccaacaaccg cttcttggtc gaaggcagca    1500
agcgcgatga atgtcttact acggagcaag ttcccgaggt aatcggagtc cggctgatgt    1560
tgggagtagg tggctacgtc tccgaactca cgaccgaaaa gatcaagagc agcccgcatg    1620
gatttgactt ggtcagggcc gagcctacat gtgcgaatga tgcccatact tgagccacct    1680
aactttgttt tagggcgact gccctgctgc gtaacatcgt tgctgctgcg taacatcgtt    1740
gctgctccat aacatcaaac atcgacccac ggcgtaacgc gcttgctgct tggatgcccg    1800
aggcatagac tgtacaaaaa aacagtcata acaagccatg aaaaccgcca ctgcgccgtt    1860
accaccgctg cgttcggtca aggttctgga ccagttgcgt gagcgcatac gctacttgca    1920
ttacagttta cgaaccgaac aggcttatgt caactgggtt cgtgccttca tccgtttcca    1980
cggtgtgcgt cacccggcaa ccttgggcag cagcgaagtc gccataactt cgtatagcat    2040
acattatacg aagttatctg taactataac ggtcctaagg tagcgagttt aaacactagt    2100
atcgattcgc gacctactcc ggaatattaa tagatcatgg agataattaa aatgataacc    2160
atctcgcaaa taataagta ttttactgtt ttcgtaacag ttttgtaata aaaaaaccta    2220
taaatattcc ggattattca taccgtccca ccatcgggcg cggatccatg aggagacgag    2280
ccgtgctagg cggagcggtg gtgtatccgg agggtcctcc tccttcttac gagagcgtga    2340
tgcagcaaca ggcggcgatg atacagcccc cactggaggc tcccttcgta cccccacggt    2400
acctggcgcc tacggaaggg agaaacagca ttcgttactc ggagctgtcg cccctgtacg    2460
```

| | |
|---|---|
| ataccaccaa gttgtatctg gtggacaaca agtcggcgga catcgcctcc ctgaactatc | 2520 |
| agaacgacca cagcaacttc ctgaccacgg tggtgcagaa caatgacttt accccacgg | 2580 |
| aggctagcac ccagaccatc aactttgacg agcggtcgcg atggggcggt cagctgaaga | 2640 |
| ccatcatgca caccaacatg cccaacgtga acgagtacat gttcagcaac aagttcaagg | 2700 |
| cgagggtgat ggtgtccaga aaagctcctg aaggtgaatt cgttacagtc aatgacggtc | 2760 |
| cggtcaatga cacctatgat cataaagagg atatcttgaa gtatgagtgg tttgagttca | 2820 |
| ttttaccaga aggcaacttt tcagccacca tgacgatcga cctgatgaac aatgccatca | 2880 |
| ttgacaacta cctggaaatt ggcagacaga atggagtgct ggaaagtgac attggtgtta | 2940 |
| agtttgacac tagaaatttc aggctcgggt gggaccccga aactaagttg attatgccag | 3000 |
| gtgtctacac ttatgaggca ttccatcctg acattgtatt gctgcctggt tgcggggtag | 3060 |
| actttactga aagccgactt agcaacttgc ttggcatcag gaagagacat ccattccagg | 3120 |
| agggtttcaa aatcatgtat gaagatcttg aaggggtaa tattcctgcc cttttggatg | 3180 |
| tcactgccta tgaggaaagc aaaaaggata ccactactgc gcgcgaaaca accacactgg | 3240 |
| ctgttgcaga ggaaactagt gaagatgtcg acgatgatat aactagagga gatacctata | 3300 |
| taactgagct cgaaaacaa aaacgtgaag ctgctgctgc tgaagtttct agaaaaaaag | 3360 |
| agttaaagat ccaacctctg gaaaagaca gcaagagtag aagctacaat gtcttggaag | 3420 |
| acaaaatcaa cacagcctac cgcagttggt atctgtccta caattacggt aaccctgaga | 3480 |
| aaggaataag gtcttggaca ctgctcacca cttcagatgt cacctgtggg gcagagcagg | 3540 |
| tctactggtc gctccctgac atgatgcaag acccagtcac cttccgctcc acaagacaag | 3600 |
| tcaacaacta cccagtggtg ggtgcagagc ttatgcccgt cttctcaaag agtttctaca | 3660 |
| atgagcaagc cgtgtactct cagcagctcc gacaggccac ttcgctcacg cacgtcttca | 3720 |
| accgcttccc tgagaaccag atcctcatcc gcccgccggc acccacaatt accaccgtca | 3780 |
| gtgaaaacgt tcctgctctc acagatcacg ggaccctgcc gttacgcagc agtatccggg | 3840 |
| gagtccagcg cgtgaccgtt actgacgcca gacgccgcac ctgtccctac gtttacaagg | 3900 |
| ccctgggcat agtcgcgccg cgcgttcttt caagccgcac tttctgataa gcttccatca | 3960 |
| actttgacga gcggtcgcga tggggcggtc agctgaagac catcatgcac accaacatgc | 4020 |
| ccaacgtgaa cgagtacatg ttcagcaaca agttcaaggc gagggagctt gtcgagaagt | 4080 |
| actagaggat cataatcagc cataccacat tgtagaggt tttacttgct ttaaaaaacc | 4140 |
| tcccacacct cccctgaac ctgaaacata aatgaatgc aattgttgtt gttaacttgt | 4200 |
| ttattgcagc ttataatggt tacaaataaa gcaatagcat cacaaatttc acaaataaag | 4260 |
| cattttttc actgcattct agttgtggtt tgtccaaact catcaatgta tcttatcatg | 4320 |
| tctggatctg atcactgctt gagcctagaa gatccggctg ctaacaaagc ccgaaggaa | 4380 |
| gctgagttgg ctgctgccac cgctgagcaa taactatcat aacccctagg gtatacccat | 4440 |
| ctaattggaa ccagataagt gaaatctagt tccaaactat tttgtcattt ttaattttcg | 4500 |
| tattagctta cgacgctaca cccagttccc atctattttg tcactcttcc ctaaataatc | 4560 |
| cttaaaaact ccatttccac ccctcccagt tcccaactat tttgtccgcc caca | 4614 |

<210> SEQ ID NO 63
<211> LENGTH: 1683
<212> TYPE: DNA
<213> ORGANISM: Artificial Sequence
<220> FEATURE:
<223> OTHER INFORMATION: ADDomere 1 engineered penton base protomer nucleic acid sequence ready for insertion of heterologous
polypeptides

<400> SEQUENCE: 63

```
atgaggagac gagccgtgct aggcggagcg gtggtgtatc cggagggtcc tcctccttct      60
tacgagagcg tgatgcagca acaggcggcg atgatacagc ccccactgga ggctcccttc     120
gtaccccac ggtacctggc gcctacggaa gggagaaaca gcattcgtta ctcggagctg      180
tcgcccctgt acgataccac caagttgtat ctggtggaca caagtcggc ggacatcgcc      240
tccctgaact atcagaacga ccacagcaac ttcctgacca cggtggtgca gaacaatgac     300
tttaccccca cggaggctag cacccagacc atcaactttg acgagcggtc gcgatggggc     360
ggtcagctga agaccatcat gcacaccaac atgcccaacg tgaacgagta catgttcagc     420
aacaagttca aggcgagggt gatggtgtcc agaaaagctc tgaaggtgaa attcgttaca     480
gtcaatgacg gtccggtcaa tgacacctat gatcataaag aggatatctt gaagtatgag     540
tggtttgagt tcattttacc agaaggcaac ttttcagcca ccatgacgat cgacctgatg     600
aacaatgcca tcattgacaa ctacctggaa attggcagac agaatggagt gctggaaagt     660
gacattggtg ttaagtttga cactagaaat ttcaggctcg ggtgggaccc cgaaactaag     720
ttgattatgc caggtgtcta cacttatgag gcattccatc ctgacattgt attgctgcct     780
ggttgcgggg tagactttac tgaaagccga cttagcaact tgcttggcat caggaagaga     840
catccattcc aggagggttt caaaatcatg tatgaagatc ttgaaggggg taatattcct     900
gcccttttgg atgtcactgc ctatgaggaa agcaaaaagg ataccactac tgcgcgcgaa     960
acaaccacac tggctgttgc agaggaaact agtgaagatg tcgacgatga tataactaga    1020
ggagatacct atataactga gctcgaaaaa caaaaacgtg aagctgctgc tgctgaagtt    1080
tctagaaaaa aagagttaaa gatccaacct ctggaaaaag acagcaagag tagaagctac    1140
aatgtcttgg aagacaaaat caacacagcc taccgcagtt ggtatctgtc ctacaattac    1200
ggtaaccctg agaaaggaat aaggtcttgg acactgctca ccacttcaga tgtcacctgt    1260
ggggcagagc aggtctactg gtcgctccct gacatgatgc aagacccagt caccttccgc    1320
tccacaagac aagtcaacaa ctacccagtg gtgggtgcag agcttatgcc cgtcttctca    1380
aagagtttct acaatgagca agccgtgtac tctcagcagc tccgacaggc cacttcgctc    1440
acgcacgtct tcaaccgctt ccctgagaac cagatcctca tccgcccgcc ggcacccaca    1500
attaccaccg tcagtgaaaa cgttcctgct ctcacagatc acgggaccct gccgttacgc    1560
agcagtatcc ggggagtcca gcgcgtgacc gttactgacg ccagacgccg cacctgtccc    1620
tacgtttaca aggccctggg catagtcgcg ccgcgcgttc tttcaagccg cactttctga    1680
taa                                                                  1683
```

<210> SEQ ID NO 64
<211> LENGTH: 559
<212> TYPE: PRT
<213> ORGANISM: Artificial Sequence
<220> FEATURE:
<223> OTHER INFORMATION: ADDomere 1.0 protein sequence ready for
      insertion of heterologous polypeptides

<400> SEQUENCE: 64

Met Arg Arg Arg Ala Val Leu Gly Gly Ala Val Val Tyr Pro Glu Gly
1               5                   10                  15

Pro Pro Pro Ser Tyr Glu Ser Val Met Gln Gln Gln Ala Ala Met Ile
            20                  25                  30

```
Gln Pro Pro Leu Glu Ala Pro Phe Val Pro Pro Arg Tyr Leu Ala Pro
         35                  40                  45

Thr Glu Gly Arg Asn Ser Ile Arg Tyr Ser Glu Leu Ser Pro Leu Tyr
 50                  55                  60

Asp Thr Thr Lys Leu Tyr Leu Val Asp Asn Lys Ser Ala Asp Ile Ala
 65                  70                  75                  80

Ser Leu Asn Tyr Gln Asn Asp His Ser Asn Phe Leu Thr Thr Val Val
                 85                  90                  95

Gln Asn Asn Asp Phe Thr Pro Thr Glu Ala Ser Thr Gln Thr Ile Asn
                100                 105                 110

Phe Asp Glu Arg Ser Arg Trp Gly Gly Gln Leu Lys Thr Ile Met His
            115                 120                 125

Thr Asn Met Pro Asn Val Asn Glu Tyr Met Phe Ser Asn Lys Phe Lys
130                 135                 140

Ala Arg Val Met Val Ser Arg Lys Ala Pro Glu Gly Glu Phe Val Thr
145                 150                 155                 160

Val Asn Asp Gly Pro Val Asn Asp Thr Tyr Asp His Lys Glu Asp Ile
                165                 170                 175

Leu Lys Tyr Glu Trp Phe Glu Phe Ile Leu Pro Glu Gly Asn Phe Ser
            180                 185                 190

Ala Thr Met Thr Ile Asp Leu Met Asn Asn Ala Ile Ile Asp Asn Tyr
            195                 200                 205

Leu Glu Ile Gly Arg Gln Asn Gly Val Leu Glu Ser Asp Ile Gly Val
    210                 215                 220

Lys Phe Asp Thr Arg Asn Phe Arg Leu Gly Trp Asp Pro Glu Thr Lys
225                 230                 235                 240

Leu Ile Met Pro Gly Val Tyr Thr Tyr Glu Ala Phe His Pro Asp Ile
                245                 250                 255

Val Leu Leu Pro Gly Cys Gly Val Asp Phe Thr Glu Ser Arg Leu Ser
                260                 265                 270

Asn Leu Leu Gly Ile Arg Lys Arg His Pro Phe Gln Glu Gly Phe Lys
            275                 280                 285

Ile Met Tyr Glu Asp Leu Glu Gly Gly Asn Ile Pro Ala Leu Leu Asp
            290                 295                 300

Val Thr Ala Tyr Glu Glu Ser Lys Lys Asp Thr Thr Thr Ala Arg Glu
305                 310                 315                 320

Thr Thr Thr Leu Ala Val Ala Glu Glu Thr Ser Glu Asp Val Asp Asp
                325                 330                 335

Asp Ile Thr Arg Gly Asp Thr Tyr Ile Thr Glu Leu Glu Lys Gln Lys
            340                 345                 350

Arg Glu Ala Ala Ala Glu Val Ser Arg Lys Lys Glu Leu Lys Ile
            355                 360                 365

Gln Pro Leu Glu Lys Asp Ser Lys Ser Arg Ser Tyr Asn Val Leu Glu
    370                 375                 380

Asp Lys Ile Asn Thr Ala Tyr Arg Ser Trp Tyr Leu Ser Tyr Asn Tyr
385                 390                 395                 400

Gly Asn Pro Glu Lys Gly Ile Arg Ser Trp Thr Leu Leu Thr Thr Ser
                405                 410                 415

Asp Val Thr Cys Gly Ala Glu Gln Val Tyr Trp Ser Leu Pro Asp Met
            420                 425                 430

Met Gln Asp Pro Val Thr Phe Arg Ser Thr Arg Gln Val Asn Asn Tyr
            435                 440                 445
```

```
Pro Val Val Gly Ala Glu Leu Met Pro Val Phe Ser Lys Ser Phe Tyr
450                 455                 460

Asn Glu Gln Ala Val Tyr Ser Gln Gln Leu Arg Gln Ala Thr Ser Leu
465                 470                 475                 480

Thr His Val Phe Asn Arg Phe Pro Glu Asn Gln Ile Leu Ile Arg Pro
                    485                 490                 495

Pro Ala Pro Thr Ile Thr Thr Val Ser Glu Asn Val Pro Ala Leu Thr
                500                 505                 510

Asp His Gly Thr Leu Pro Leu Arg Ser Ser Ile Arg Gly Val Gln Arg
                515                 520                 525

Val Thr Val Thr Asp Ala Arg Arg Arg Thr Cys Pro Tyr Val Tyr Lys
530                 535                 540

Ala Leu Gly Ile Val Ala Pro Arg Val Leu Ser Ser Arg Thr Phe
545                 550                 555

<210> SEQ ID NO 65
<211> LENGTH: 559
<212> TYPE: PRT
<213> ORGANISM: Artificial Sequence
<220> FEATURE:
<223> OTHER INFORMATION: ADDomere 2.0 protein sequence with coupling
      residues at position 51 and 54

<400> SEQUENCE: 65

Met Arg Arg Arg Ala Val Leu Gly Gly Ala Val Val Tyr Pro Glu Gly
1               5                   10                  15

Pro Pro Pro Ser Tyr Glu Ser Val Met Gln Gln Gln Ala Ala Met Ile
                20                  25                  30

Gln Pro Pro Leu Glu Ala Pro Phe Val Pro Pro Arg Tyr Leu Ala Pro
                35                  40                  45

Thr Glu Cys Arg Asn Cys Ile Arg Tyr Ser Glu Leu Ser Pro Leu Tyr
                50                  55                  60

Asp Thr Thr Lys Leu Tyr Leu Val Asp Asn Lys Ser Ala Asp Ile Ala
65                  70                  75                  80

Ser Leu Asn Tyr Gln Asn Asp His Ser Asn Phe Leu Thr Thr Val Val
                85                  90                  95

Gln Asn Asn Asp Phe Thr Pro Thr Glu Ala Ser Thr Gln Thr Ile Asn
                100                 105                 110

Phe Asp Glu Arg Ser Arg Trp Gly Gly Gln Leu Lys Thr Ile Met His
                115                 120                 125

Thr Asn Met Pro Asn Val Asn Glu Tyr Met Phe Ser Asn Lys Phe Lys
130                 135                 140

Ala Arg Val Met Val Ser Arg Lys Ala Pro Glu Gly Glu Phe Val Thr
145                 150                 155                 160

Val Asn Asp Gly Pro Val Asn Asp Thr Tyr Asp His Lys Glu Asp Ile
                165                 170                 175

Leu Lys Tyr Glu Trp Phe Glu Phe Ile Leu Pro Glu Gly Asn Phe Ser
                180                 185                 190

Ala Thr Met Thr Ile Asp Leu Met Asn Asn Ala Ile Ile Asp Asn Tyr
                195                 200                 205

Leu Glu Ile Gly Arg Gln Asn Gly Val Leu Glu Ser Asp Ile Gly Val
                210                 215                 220

Lys Phe Asp Thr Arg Asn Phe Arg Leu Gly Trp Asp Pro Glu Thr Lys
225                 230                 235                 240

Leu Ile Met Pro Gly Val Tyr Thr Tyr Glu Ala Phe His Pro Asp Ile
                245                 250                 255
```

Val Leu Leu Pro Gly Cys Gly Val Asp Phe Thr Glu Ser Arg Leu Ser
            260                 265                 270

Asn Leu Leu Gly Ile Arg Lys Arg His Pro Phe Gln Glu Gly Phe Lys
            275                 280                 285

Ile Met Tyr Glu Asp Leu Glu Gly Gly Asn Ile Pro Ala Leu Leu Asp
        290                 295                 300

Val Thr Ala Tyr Glu Glu Ser Lys Lys Asp Thr Thr Ala Arg Glu
305                 310                 315                 320

Thr Thr Thr Leu Ala Val Ala Glu Glu Thr Ser Glu Asp Val Asp Asp
                325                 330                 335

Asp Ile Thr Arg Gly Asp Thr Tyr Ile Thr Glu Leu Glu Lys Gln Lys
            340                 345                 350

Arg Glu Ala Ala Ala Glu Val Ser Arg Lys Lys Glu Leu Lys Ile
            355                 360                 365

Gln Pro Leu Glu Lys Asp Ser Lys Ser Arg Ser Tyr Asn Val Leu Glu
        370                 375                 380

Asp Lys Ile Asn Thr Ala Tyr Arg Ser Trp Tyr Leu Ser Tyr Asn Tyr
385                 390                 395                 400

Gly Asn Pro Glu Lys Gly Ile Arg Ser Trp Thr Leu Leu Thr Thr Ser
                405                 410                 415

Asp Val Thr Cys Gly Ala Glu Gln Val Tyr Trp Ser Leu Pro Asp Met
            420                 425                 430

Met Gln Asp Pro Val Thr Phe Arg Ser Thr Arg Gln Val Asn Asn Tyr
            435                 440                 445

Pro Val Val Gly Ala Glu Leu Met Pro Val Phe Ser Lys Ser Phe Tyr
        450                 455                 460

Asn Glu Gln Ala Val Tyr Ser Gln Gln Leu Arg Gln Ala Thr Ser Leu
465                 470                 475                 480

Thr His Val Phe Asn Arg Phe Pro Glu Asn Gln Ile Leu Ile Arg Pro
                485                 490                 495

Pro Ala Pro Thr Ile Thr Thr Val Ser Glu Asn Val Pro Ala Leu Thr
            500                 505                 510

Asp His Gly Thr Leu Pro Leu Arg Ser Ser Ile Arg Gly Val Gln Arg
            515                 520                 525

Val Thr Val Thr Asp Ala Arg Arg Arg Thr Cys Pro Tyr Val Tyr Lys
        530                 535                 540

Ala Leu Gly Ile Val Ala Pro Arg Val Leu Ser Ser Arg Thr Phe
545                 550                 555

<210> SEQ ID NO 66
<211> LENGTH: 559
<212> TYPE: PRT
<213> ORGANISM: Artificial Sequence
<220> FEATURE:
<223> OTHER INFORMATION: ADDomere 2.0 protein sequence with coupling
      residues at position 51 and 114

<400> SEQUENCE: 66

Met Arg Arg Arg Ala Val Leu Gly Gly Ala Val Val Tyr Pro Glu Gly
1               5                   10                  15

Pro Pro Pro Ser Tyr Glu Ser Val Met Gln Gln Ala Ala Met Ile
            20                  25                  30

Gln Pro Pro Leu Glu Ala Pro Phe Val Pro Arg Tyr Leu Ala Pro
        35                  40                  45

Thr Glu Gly Arg Asn Cys Ile Arg Tyr Ser Glu Leu Ser Pro Leu Tyr

```
            50                  55                  60
Asp Thr Thr Lys Leu Tyr Leu Val Asp Asn Lys Ser Ala Asp Ile Ala
65                  70                  75                  80

Ser Leu Asn Tyr Gln Asn Asp His Ser Asn Phe Leu Thr Thr Val Val
                85                  90                  95

Gln Asn Asn Asp Phe Thr Pro Thr Glu Ala Ser Thr Gln Thr Ile Asn
            100                 105                 110

Phe Cys Glu Arg Ser Arg Trp Gly Gly Gln Leu Lys Thr Ile Met His
        115                 120                 125

Thr Asn Met Pro Asn Val Asn Glu Tyr Met Phe Ser Asn Lys Phe Lys
    130                 135                 140

Ala Arg Val Met Val Ser Arg Lys Ala Pro Glu Gly Glu Phe Val Thr
145                 150                 155                 160

Val Asn Asp Gly Pro Val Asn Asp Thr Tyr Asp His Lys Glu Asp Ile
                165                 170                 175

Leu Lys Tyr Glu Trp Phe Glu Phe Ile Leu Pro Glu Gly Asn Phe Ser
            180                 185                 190

Ala Thr Met Thr Ile Asp Leu Met Asn Asn Ala Ile Ile Asp Asn Tyr
        195                 200                 205

Leu Glu Ile Gly Arg Gln Asn Gly Val Leu Glu Ser Asp Ile Gly Val
    210                 215                 220

Lys Phe Asp Thr Arg Asn Phe Arg Leu Gly Trp Asp Pro Glu Thr Lys
225                 230                 235                 240

Leu Ile Met Pro Gly Val Tyr Thr Tyr Glu Ala Phe His Pro Asp Ile
                245                 250                 255

Val Leu Leu Pro Gly Cys Gly Val Asp Phe Thr Glu Ser Arg Leu Ser
            260                 265                 270

Asn Leu Leu Gly Ile Arg Lys Arg His Pro Phe Gln Glu Gly Phe Lys
        275                 280                 285

Ile Met Tyr Glu Asp Leu Glu Gly Gly Asn Ile Pro Ala Leu Leu Asp
    290                 295                 300

Val Thr Ala Tyr Glu Glu Ser Lys Lys Asp Thr Thr Ala Arg Glu
305                 310                 315                 320

Thr Thr Thr Leu Ala Val Ala Glu Glu Thr Ser Glu Asp Val Asp Asp
            325                 330                 335

Asp Ile Thr Arg Gly Asp Thr Tyr Ile Thr Glu Leu Glu Lys Gln Lys
        340                 345                 350

Arg Glu Ala Ala Ala Glu Val Ser Arg Lys Glu Leu Lys Ile
    355                 360                 365

Gln Pro Leu Glu Lys Asp Ser Lys Ser Arg Ser Tyr Asn Val Leu Glu
370                 375                 380

Asp Lys Ile Asn Thr Ala Tyr Arg Ser Trp Tyr Leu Ser Tyr Asn Tyr
385                 390                 395                 400

Gly Asn Pro Glu Lys Gly Ile Arg Ser Trp Thr Leu Leu Thr Thr Ser
            405                 410                 415

Asp Val Thr Cys Gly Ala Glu Gln Val Tyr Trp Ser Leu Pro Asp Met
        420                 425                 430

Met Gln Asp Pro Val Thr Phe Arg Ser Thr Arg Gln Val Asn Asn Tyr
    435                 440                 445

Pro Val Val Gly Ala Glu Leu Met Pro Val Phe Ser Lys Ser Phe Tyr
450                 455                 460

Asn Glu Gln Ala Val Tyr Ser Gln Gln Leu Arg Gln Ala Thr Ser Leu
465                 470                 475                 480
```

```
Thr His Val Phe Asn Arg Phe Pro Glu Asn Gln Ile Leu Ile Arg Pro
            485                 490                 495

Pro Ala Pro Thr Ile Thr Thr Val Ser Glu Asn Val Pro Ala Leu Thr
            500                 505                 510

Asp His Gly Thr Leu Pro Leu Arg Ser Ser Ile Arg Gly Val Gln Arg
            515                 520                 525

Val Thr Val Thr Asp Ala Arg Arg Thr Cys Pro Tyr Val Tyr Lys
        530                 535                 540

Ala Leu Gly Ile Val Ala Pro Arg Val Leu Ser Ser Arg Thr Phe
545                 550                 555

<210> SEQ ID NO 67
<211> LENGTH: 559
<212> TYPE: PRT
<213> ORGANISM: Artificial Sequence
<220> FEATURE:
<223> OTHER INFORMATION: ADDomere 2.0 protein sequence with coupling
      residues at position 51 and 541

<400> SEQUENCE: 67

Met Arg Arg Arg Ala Val Leu Gly Gly Ala Val Val Tyr Pro Glu Gly
1               5                   10                  15

Pro Pro Pro Ser Tyr Glu Ser Val Met Gln Gln Gln Ala Ala Met Ile
            20                  25                  30

Gln Pro Pro Leu Glu Ala Pro Phe Val Pro Pro Arg Tyr Leu Ala Pro
            35                  40                  45

Thr Glu Gly Arg Cys Ser Ile Arg Tyr Ser Glu Leu Ser Pro Leu Tyr
50                  55                  60

Asp Thr Thr Lys Leu Tyr Leu Val Asp Asn Lys Ser Ala Asp Ile Ala
65                  70                  75                  80

Ser Leu Asn Tyr Gln Asn Asp His Ser Asn Phe Leu Thr Thr Val Val
                85                  90                  95

Gln Asn Asn Asp Phe Thr Pro Thr Glu Ala Ser Thr Gln Thr Ile Asn
            100                 105                 110

Phe Asp Glu Arg Ser Arg Trp Gly Gly Gln Leu Lys Thr Ile Met His
            115                 120                 125

Thr Asn Met Pro Asn Val Asn Glu Tyr Met Phe Ser Asn Lys Phe Lys
130                 135                 140

Ala Arg Val Met Val Ser Arg Lys Ala Pro Glu Gly Glu Phe Val Thr
145                 150                 155                 160

Val Asn Asp Gly Pro Val Asn Asp Thr Tyr Asp His Lys Glu Asp Ile
                165                 170                 175

Leu Lys Tyr Glu Trp Phe Glu Phe Ile Leu Pro Glu Gly Asn Phe Ser
            180                 185                 190

Ala Thr Met Thr Ile Asp Leu Met Asn Asn Ala Ile Ile Asp Asn Tyr
            195                 200                 205

Leu Glu Ile Gly Arg Gln Asn Gly Val Leu Glu Ser Asp Ile Gly Val
            210                 215                 220

Lys Phe Asp Thr Arg Asn Phe Arg Leu Gly Trp Asp Pro Glu Thr Lys
225                 230                 235                 240

Leu Ile Met Pro Gly Val Tyr Thr Tyr Glu Ala Phe His Pro Asp Ile
                245                 250                 255

Val Leu Leu Pro Gly Cys Gly Val Asp Phe Thr Glu Ser Arg Leu Ser
            260                 265                 270

Asn Leu Leu Gly Ile Arg Lys Arg His Pro Phe Gln Glu Gly Phe Lys
```

```
                275                 280                 285
Ile Met Tyr Glu Asp Leu Glu Gly Gly Asn Ile Pro Ala Leu Leu Asp
    290                 295                 300

Val Thr Ala Tyr Glu Glu Ser Lys Lys Asp Thr Thr Ala Arg Glu
305                 310                 315                 320

Thr Thr Thr Leu Ala Val Ala Glu Thr Ser Glu Asp Val Asp Asp
                325                 330                 335

Asp Ile Thr Arg Gly Asp Thr Tyr Ile Thr Glu Leu Glu Lys Gln Lys
            340                 345                 350

Arg Glu Ala Ala Ala Glu Val Ser Arg Lys Lys Glu Leu Lys Ile
            355                 360                 365

Gln Pro Leu Glu Lys Asp Ser Lys Ser Arg Ser Tyr Asn Val Leu Glu
            370                 375                 380

Asp Lys Ile Asn Thr Ala Tyr Arg Ser Trp Tyr Leu Ser Tyr Asn Tyr
385                 390                 395                 400

Gly Asn Pro Glu Lys Gly Ile Arg Ser Trp Thr Leu Leu Thr Thr Ser
                405                 410                 415

Asp Val Thr Cys Gly Ala Glu Gln Val Tyr Trp Ser Leu Pro Asp Met
            420                 425                 430

Met Gln Asp Pro Val Thr Phe Arg Ser Thr Arg Gln Val Asn Asn Tyr
            435                 440                 445

Pro Val Val Gly Ala Glu Leu Met Pro Val Phe Ser Lys Ser Phe Tyr
450                 455                 460

Asn Glu Gln Ala Val Tyr Ser Gln Gln Leu Arg Gln Ala Thr Ser Leu
465                 470                 475                 480

Thr His Val Phe Asn Arg Phe Pro Glu Asn Gln Ile Leu Ile Arg Pro
                485                 490                 495

Pro Ala Pro Thr Ile Thr Thr Val Ser Glu Asn Val Pro Ala Leu Thr
                500                 505                 510

Asp His Gly Thr Leu Pro Leu Arg Ser Ser Ile Arg Gly Val Gln Arg
            515                 520                 525

Val Thr Val Thr Asp Ala Arg Arg Thr Cys Pro Cys Val Tyr Lys
530                 535                 540

Ala Leu Gly Ile Val Ala Pro Arg Val Leu Ser Ser Arg Thr Phe
545                 550                 555
```

<210> SEQ ID NO 68
<211> LENGTH: 10
<212> TYPE: PRT
<213> ORGANISM: Artificial Sequence
<220> FEATURE:
<223> OTHER INFORMATION: Consenus sequence of penton base protomer in
      the STICKER binding cleft
<220> FEATURE:
<221> NAME/KEY: MISC_FEATURE
<222> LOCATION: (4)..(4)
<223> OTHER INFORMATION: Xaa is selected from the group consisting of Y
      and F
<220> FEATURE:
<221> NAME/KEY: MISC_FEATURE
<222> LOCATION: (6)..(6)
<223> OTHER INFORMATION: Xaa is selected from the group consisting of D,
      E and a coupling residue, preferably Cys
<220> FEATURE:
<221> NAME/KEY: MISC_FEATURE
<222> LOCATION: (7)..(7)
<223> OTHER INFORMATION: Xaa is selected from the group consisting of L,
      Q and a coupling residue, preferably Cys

<400> SEQUENCE: 68

Lys Ser Phe Xaa Asn Xaa Xaa Ala Val Tyr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: STICKER N-terminal fragment of fibre comprising
      acoupling residue
<220> FEATURE:
<221> NAME/KEY: MISC_FEATURE
<222> LOCATION: (1)..(1)
<223> OTHER INFORMATION: Xaa is selected from the group consisting of S,
      D and T
<220> FEATURE:
<221> NAME/KEY: MISC_FEATURE
<222> LOCATION: (9)..(9)
<223> OTHER INFORMATION: Xaa is selected from the group consisting of E,
      D and G
<220> FEATURE:
<221> NAME/KEY: MISC_FEATURE
<222> LOCATION: (10)..(10)
<223> OTHER INFORMATION: Xaa is in each case independently any amino
      acid, preferably those naturally occurring in fibre proteins at
      this or these positions
<220> FEATURE:
<221> NAME/KEY: MISC_FEATURE
<222> LOCATION: (11)..(11)
<223> OTHER INFORMATION: Xaa is a coupling residue, preferably Cys
<220> FEATURE:
<221> NAME/KEY: misc_feature
<222> LOCATION: (12)..(12)
<223> OTHER INFORMATION: Xaa can be any naturally occurring amino acid

<400> SEQUENCE: 69

Xaa Phe Asn Pro Val Tyr Pro Tyr Xaa Xaa Asn Xaa
1               5                   10

<210> SEQ ID NO 70
<211> LENGTH: 9
<212> TYPE: PRT
<213> ORGANISM: Artificial Sequence
<220> FEATURE:
<223> OTHER INFORMATION: STICKER N-terminal fragment of fibre comprising
      a coupling residue
<220> FEATURE:
<221> NAME/KEY: MISC_FEATURE
<222> LOCATION: (1)..(1)
<223> OTHER INFORMATION: Xaa is a coupling residue, preferably Cys
<220> FEATURE:
<221> NAME/KEY: MISC_FEATURE
<222> LOCATION: (9)..(9)
<223> OTHER INFORMATION: Xaa is selected from the group consisting of E,
      D and G

<400> SEQUENCE: 70

Xaa Phe Asn Pro Val Tyr Pro Tyr Xaa
1               5

<210> SEQ ID NO 71
<211> LENGTH: 4692
<212> TYPE: DNA
<213> ORGANISM: Artificial Sequence
<220> FEATURE:
<223> OTHER INFORMATION: pACEBac-ADDomer2.0TevChik plasmid sequence

<400> SEQUENCE: 71
accggttgac ttgggtcaac tgtcagacca agtttactca tatatacttt agattgattt      60
aaaacttcat ttttaattta aaaggatcta ggtgaagatc cttttttgata atctcatgac    120 caaaatccct taacgtgagt tttcgttcca ctgagcgtca gaccccgtag aaaagatcaa    180

```
aggatcttct tgagatcctt tttttctgcg cgtaatctgc tgcttgcaaa caaaaaaacc    240
accgctacca gcggtggttt gtttgccgga tcaagagcta ccaactcttt ttccgaaggt    300
aactggcttc agcagagcgc agataccaaa tactgttctt ctagtgtagc cgtagttagg    360
ccaccacttc aagaactctg tagcaccgcc tacatacctc gctctgctaa tcctgttacc    420
agtggctgct gccagtggcg ataagtcgtg tcttaccggg ttggactcaa gacgatagtt    480
accggataag cgcagcggt cgggctgaac gggggttcg tgcacacagc ccagcttgga    540
gcgaacgacc tacaccgaac tgagatacct acagcgtgag ctatgagaaa gcgccacgct    600
tcccgaaggg agaaaggcgg acaggtatcc ggtaagcggc agggtcggaa caggagagcg    660
cacgagggag cttccagggg gaaacgcctg gtatctttat agtcctgtcg ggtttcgcca    720
cctctgactt gagcgtcgat ttttgtgatg ctcgtcaggg gggcggagcc tatgaaaaa    780 cgccagcaac gcggccttt tacggttcct ggccttttgc tggccttttg ctcacatgtt    840
ctttcctgcg ttatccctg attgacttgg gtcgctcttc ctgtggatgc gcagatgccc    900
tgcgtaagcg ggtgtgggcg gacaataaag tcttaaactg aacaaaatag atctaaacta    960
tgacaataaa gtcttaaact agacagaata gttgtaaact gaaatcagtc cagttatgct   1020
gtgaaaaagc atactggact tttgttatgg ctaaagcaaa ctcttcattt tctgaagtgc   1080
aaattgcccg tcgtattaaa gaggggcgtg gccaagggca tgtaaagact atattcgcgg   1140
cgttgtgaca atttaccgaa caactccgcg gccgggaagc cgatctcggc ttgaacgaat   1200
tgttaggtgg cggtacttgg gtcgatatca aagtgcatca cttcttcccg tatgcccaac   1260
tttgtataga gagccactgc gggatcgtca ccgtaatctg cttgcacgta gatcacataa   1320
gcaccaagcg cgttggcctc atgcttgagg agattgatga gcgcgtggc aatgccctgc   1380 ctccggtgct cgccggagac tgcgagatca tagatataga tctcactacg cggctgctca   1440
aacttgggca gaacgtaagc cgcgagagcg ccaacaaccg cttcttggtc gaaggcagca   1500
agcgcgatga atgtcttact acggagcaag ttcccgaggt aatcggagtc cggctgatgt   1560
tgggagtagg tggctacgtc tccgaactca cgaccgaaaa gatcaagagc agcccgcatg   1620
gatttgactt ggtcagggcc gagcctacat gtgcgaatga tgcccatact tgagccacct   1680
aactttgttt tagggcgact gccctgctgc gtaacatcgt tgctgctgcg taacatcgtt   1740
gctgctccat aacatcaaac atcgacccac ggcgtaacgc gcttgctgct tggatgcccg   1800
aggcatagac tgtacaaaaa aacagtcata acaagccatg aaaaccgcca ctgcgccgtt   1860
accaccgctg cgttcggtca aggttctgga ccagttgcgt gagcgcatac gctacttgca   1920
ttacagttta cgaaccgaac aggcttatgt caactgggtt cgtgccttca tccgtttcca   1980
cggtgtgcgt caccggcaa ccttgggcag cagcgaagtc gccataactt cgtatagcat   2040
acattatacg aagttatctg taactataac ggtcctaagg tagcgagttt aaacactagt   2100
atcgattcgc gacctactcc ggaatattaa tagatcatgg agataattaa aatgataacc   2160
atctcgcaaa taaataagta tttttactgtt ttcgtaacag ttttgtaata aaaaaaccta   2220
taaatattcc ggattattca taccgtccca ccatcgggcg cggatccatg aggagacgag   2280
ccgtgctagg cggagcggtg gtgtatccgg agggtcctcc tccttcttac gagagcgtga   2340
tgcagcaaca ggcggcgatg atacagcccc cactggaggc tcccttcgta ccccacggt    2400 acctggcgcc tacggaaggg agaaacagca ttcgttactc ggagctgtcg cccctgtacg   2460
ataccaccaa gttgtatctg gtggacaaca agtcggcgga catcgcctcc ctgaactatc   2520
```

```
agaacgacca cagcaacttc ctgaccacgg tggtgcagaa caatgacttt acccccacgg      2580
aggctagcac ccagaccatc aactttgacg agcggtcgcg atggggcggt cagctgaaga      2640
ccatcatgca caccaacatg cccaacgtga acgagtacat gttcagcaac aagttcaagg      2700
cgagggtgat ggtgtccaga aaagctcctg aaggtgaatt cggcagcggt ggcgaaaacc      2760
tgtattttca gagcaccaaa gataaccttta acgtgtataa agcgacccgc ccgtatctgg      2820
cgcatggtgg cagcggtccg gtcaatgaca cctatgatca taagaggat atcttgaagt       2880 atgagtggtt tgagttcatt ttaccagaag gcaacttttc agccaccatg acgatcgacc      2940
tgatgaacaa tgccatcatt gacaactacc tggaaattgg cagacagaat ggagtgctgg      3000
aaagtgacat tggtgttaag tttgacacta gaaatttcag gctcgggtgg gaccccgaaa      3060
ctaagttgat tatgccaggt gtctacactt atgaggcatt ccatcctgac attgtattgc      3120
tgcctggttg cggggtagac tttactgaaa gccgactttag caacttgctt ggcatcagga     3180
agagacatcc attccaggag ggtttcaaaa tcatgtatga agatcttgaa gggggtaata      3240
ttcctgccct tttggatgtc actgcctatg aggaaagcaa aaaggatacc actactgcgc      3300
gcgaaacaac cacactggct gttgcagagg aaactagtga agatgtcgac gatgatataa      3360
ctagaggaga tacctatata actgagctcg aaaaacaaaa acgtgaagct gctgctgctg      3420
aagtttctag aaaaaaagag ttaaagatcc aacctctgga aaaagacagc aagagtagaa      3480
gctacaatgt cttggaagac aaaatcaaca cagcctaccg cagttggtat ctgtcctaca      3540
attacggtaa ccctgagaaa ggaataaggt cttggacact gctcaccact tcagatgtca      3600
cctgtggggc agagcaggtc tactggtcgc tccctgacat gatgcaagac ccagtcacct      3660
tccgctccac aagacaagtc aacaactacc cagtggtggg tgcagagctt atgcccgtct      3720
tctcaaagag tttctacaat gagcaagccg tgtactctca gcagctccga caggccactt      3780
cgctcacgca cgtcttcaac cgcttccctg agaaccagat cctcatccgc ccgccggcac      3840
ccacaattac caccgtcagt gaaaacgttc ctgctctcac agatcacggg accctgccgt      3900
tacgcagcag tatccgggga gtccagcgcg tgaccgttac tgacgccaga cgccgcacct      3960
gtccctacgt ttacaaggcc ctgggcatag tcgcgccgcg cgttctttca gccgcacttt      4020
tctgataagc ttccatcaac tttgacgagc ggtcgcgatg gggcggtcag ctgaagacca      4080
tcatgcacac caacatgccc aacgtgaacg agtacatgtt cagcaacaag ttcaaggcga      4140
gggagcttgt cgagaagtac tagaggatca taatcagcca taccacattt gtagaggttt      4200
tacttgcttt aaaaaacctc ccacacctcc ccctgaacct gaaacataaa atgaatgcaa      4260
ttgttgttgt taacttgttt attgcagctt ataatggtta caaataaagc aatagcatca      4320
caaatttcac aaataaagca tttttttcac tgcattctag ttgtggtttg tccaaactca      4380
tcaatgtatc ttatcatgtc tggatctgat cactgcttga gcctagaaga tccggctgct      4440
aacaaagccc gaaaggaagc tgagttggct gctgccaccg ctgagcaata actatcataa      4500
cccctagggt atacccatct aattggaacc agataagtga aatctagttc caaactattt      4560
tgtcattttt aattttcgta ttagcttacg acgctacacc cagttcccat ctattttgtc      4620
actcttccct aaataatcct taaaaactcc atttccaccc ctcccagttc ccaactattt      4680
tgtccgccca ca                                                         4692
```

<210> SEQ ID NO 72
<211> LENGTH: 4788
<212> TYPE: DNA
<213> ORGANISM: Artificial Sequence
<220> FEATURE:
<223> OTHER INFORMATION: pACEBac-ADDOmer2.0-[TevCHIK]2 plasmid sequence

<400> SEQUENCE: 72

| | | | | | |
|---|---|---|---|---|---|
| accggttgac | ttgggtcaac | tgtcagacca | agtttactca | tatatacttt | agattgattt | 60 |
| aaaacttcat | ttttaattta | aaaggatcta | ggtgaagatc | cttttgata | atctcatgac | 120 |
| caaaatccct | taacgtgagt | tttcgttcca | ctgagcgtca | gaccccgtag | aaaagatcaa | 180 |
| aggatcttct | tgagatcctt | tttttctgcg | cgtaatctgc | tgcttgcaaa | caaaaaaacc | 240 |
| accgctacca | gcggtggttt | gtttgccgga | tcaagagcta | ccaactcttt | ttccgaaggt | 300 |
| aactggcttc | agcagagcgc | agataccaaa | tactgttctt | ctagtgtagc | cgtagttagg | 360 |
| ccaccacttc | aagaactctg | tagcaccgcc | tacatacctc | gctctgctaa | tcctgttacc | 420 |
| agtggctgct | gccagtggcg | ataagtcgtg | tcttaccggg | ttggactcaa | gacgatagtt | 480 |
| accggataag | gcgcagcggt | cgggctgaac | ggggggttcg | tgcacacagc | ccagcttgga | 540 |
| gcgaacgacc | tacaccgaac | tgagatacct | acagcgtgag | ctatgagaaa | gcgccacgct | 600 |
| tcccgaaggg | agaaaggcgg | acaggtatcc | ggtaagcggc | agggtcggaa | caggagagcg | 660 |
| cacgagggag | cttccagggg | gaaacgcctg | gtatctttat | agtcctgtcg | ggtttcgcca | 720 |
| cctctgactt | gagcgtcgat | ttttgtgatg | ctcgtcaggg | gggcggagcc | tatggaaaaa | 780 |
| cgccagcaac | gcggccttttt | tacgttcct | ggccttttgc | tggccttttg | ctcacatgtt | 840 |
| ctttcctgcg | ttatcccctg | attgacttgg | gtcgctcttc | ctgtggatgc | gcagatgccc | 900 |
| tgcgtaagcg | ggtgtgggcg | gacaataaag | tcttaaactg | aacaaaatag | atctaaacta | 960 |
| tgacaataaa | gtcttaaact | agacagaata | gttgtaaact | gaaatcagtc | cagttatgct | 1020 |
| gtgaaaaagc | atactggact | tttgttatgg | ctaaagcaaa | ctcttcattt | tctgaagtgc | 1080 |
| aaattgcccg | tcgtattaaa | gagggggcgtg | gccaagggca | tgtaaagact | atattcgcgg | 1140 |
| cgttgtgaca | atttaccgaa | caactccgcg | gccgggaagc | cgatctcggc | ttgaacgaat | 1200 |
| tgttaggtgg | cggtacttgg | gtcgatatca | aagtgcatca | cttcttcccg | tatgcccaac | 1260 |
| tttgtataga | gagccactgc | gggatcgtca | ccgtaatctg | cttgcacgta | gatcacataa | 1320 |
| gcaccaagcg | cgttggcctc | atgcttgagg | agattgatga | gcgcggtggc | aatgccctgc | 1380 |
| ctccggtgct | cgccggagac | tgcgagatca | tagatataga | tctcactacg | cggctgctca | 1440 |
| aacttgggca | gaacgtaagc | cgcgagagcg | ccaacaaccg | cttcttggtc | gaaggcagca | 1500 |
| agcgcgatga | atgtcttact | acggagcaag | ttcccgaggt | aatcggagtc | cggctgatgt | 1560 |
| tgggagtagg | tggctacgtc | tccgaactca | cgaccgaaaa | gatcaagagc | agcccgcatg | 1620 |
| gatttgactt | ggtcagggcc | gagcctacat | gtgcgaatga | tgcccatact | tgagccacct | 1680 |
| aactttgttt | tagggcgact | gccctgctgc | gtaacatcgt | tgctgctgcg | taacatcgtt | 1740 |
| gctgctccat | aacatcaaac | atcgacccac | ggcgtaacgc | gcttgctgct | tggatgcccg | 1800 |
| aggcatagac | tgtacaaaaa | aacagtcata | acaagccatg | aaaaccgcca | ctgcgccgtt | 1860 |
| accaccgctg | cgttcggtca | aggttctgga | ccagttgcgt | gagcgcatac | gctacttgca | 1920 |
| ttacagttta | cgaaccgaac | aggcttatgt | caactgggtt | cgtgccttca | tccgtttcca | 1980 |
| cggtgtgcgt | cacccggcaa | ccttgggcag | cagcgaagtc | gccataactt | cgtatagcat | 2040 |
| acattatacg | aagttatctg | taactataac | ggtcctaagg | tagcgagttt | aaacactagt | 2100 |
| atcgattcgc | gacctactcc | ggaatattaa | tagatcatgg | agataattaa | aatgataacc | 2160 |
| atctcgcaaa | taaataagta | ttttactgtt | ttcgtaacag | ttttgtaata | aaaaaaccta | 2220 |

```
taaatattcc ggattattca taccgtccca ccatcgggcg cggatccatg aggagacgag    2280
ccgtgctagg cggagcggtg gtgtatccgg agggtcctcc tccttcttac gagagcgtga    2340
tgcagcaaca ggcggcgatg atacagcccc cactggaggc tcccttcgta ccccacggt     2400
acctggcgcc tacggaaggg agaaacagca ttcgttactc ggagctgtcg ccctgtacg     2460
ataccaccaa gttgtatctg gtggacaaca agtcggcgga catcgcctcc ctgaactatc    2520
agaacgacca cagcaacttc ctgaccacgg tggtgcagaa caatgacttt accccacgg     2580
aggctagcac ccagaccatc aactttgacg agcggtcgcg atggggcggt cagctgaaga    2640
ccatcatgca caccaacatg cccaacgtga acgagtacat gttcagcaac aagttcaagg    2700
cgagggtgat ggtgtccaga aaagctcctg aaggtgaatt cggcagcggt ggcgaaaacc    2760
tgtattttca gagcaccaaa gataacttta acgtgtataa agcgacccgc cgtatctgg    2820
cgcatggtgg cagcggtccg gtcaatgaca cctatgatca taaagaggat atcttgaagt    2880
atgagtggtt tgagttcatt ttaccagaag gcaacttttc agccaccatg acgatcgacc    2940
tgatgaacaa tgccatcatt gacaactacc tggaaattgg cagacagaat ggagtgctgg    3000
aaagtgacat tggtgttaag tttgacacta gaaatttcag gctcgggtgg gaccccgaaa    3060
ctaagttgat tatgccaggt gtctacactt atgaggcatt ccatcctgac attgtattgc    3120
tgcctggttg cggggtagac tttactgaaa gccgacttag caacttgctt ggcatcagga    3180
agagacatcc attccaggag ggtttcaaaa tcatgtatga agatcttgaa gggggtaata    3240
ttcctgccct tttggatgtc actgcctatg aggaaagcaa aaaggatacc actactgcgc    3300
gcgaaacaac cacactggct gttgcagagg aaactagtga agatgtcgac gatgatataa    3360
ctagaggaga tacctatata actgagctcg gcagcggtgg cgaaaacctg tatttcaga     3420
gcaccaaaga taactttaac gtgtataaag cgacccgccc gtatctggcg catggtggca    3480
gcggtgaaaa acaaaaacgt gaagctgctg ctgctgaagt ttctagaaaa aaagagttaa    3540
agatccaacc tctggaaaaa gacagcaaga gtagaagcta caatgtcttg gaagacaaaa    3600
tcaacacagc ctaccgcagt tggtatctgt cctacaatta cggtaaccct gagaaaggaa    3660
taaggtcttg gacactgctc accacttcag atgtcacctg tggggcagag caggtctact    3720
ggtcgctccc tgacatgatg caagacccag tcaccttccg ctccacaaga caagtcaaca    3780
actacccagt ggtgggtgca gagcttatgc ccgtcttctc aaagagtttc tacaatgagc    3840
aagccgtgta ctctcagcag ctccgacagg ccacttcgct cacgcacgtc ttcaaccgct    3900
tccctgagaa ccagatcctc atccgcccgc cggcacccac aattaccacc gtcagtgaaa    3960
acgttcctgc tctcacagat cacgggaccc tgccgttacg cagcagtatc cggggagtcc    4020
agcgcgtgac cgttactgac gccagacgcc gcacctgtcc ctacgtttac aaggccctgg    4080
gcatagtcgc gccgcgcgtt cttttcaagc cgcactttctg ataagcttcc atcaactttg    4140
acgagcggtc gcgatggggc ggtcagctga agaccatcat gcacaccaac atgcccaacg    4200
tgaacgagta catgttcagc aacaagttca aggcgaggga gcttgtcgag aagtactaga    4260
ggatcataat cagccatacc acatttgtag aggttttact tgcttttaaaa aacctcccac    4320
acctcccect gaacctgaaa cataaaatga atgcaattgt tgttgttaac ttgtttattg    4380
cagcttataa tggttacaaa taaagcaata gcatcacaaa tttcacaaat aaagcatttt    4440
tttcactgca ttctagttgt ggtttgtcca aactcatcaa tgtatcttat catgtctgga    4500
tctgatcact gcttgagcct agaagatccg gctgctaaca aagcccgaaa ggaagctgag    4560
ttggctgctg ccaccgctga gcaataacta tcataacccc tagggtatac ccatctaatt    4620
```

```
ggaaccagat aagtgaaatc tagttccaaa ctattttgtc attttaatt ttcgtattag    4680 cttacgacgc tacacccagt tcccatctat tttgtcactc ttccctaaat aatccttaaa    4740
aactccattt ccaccctcc cagttcccaa ctattttgtc cgcccaca                 4788
```

<210> SEQ ID NO 73  
<211> LENGTH: 6  
<212> TYPE: PRT  
<213> ORGANISM: Artificial Sequence  
<220> FEATURE:  
<223> OTHER INFORMATION: Consenus sequence of penton base protomer in the STICKER binding cleft  
<220> FEATURE:  
<221> NAME/KEY: MISC_FEATURE  
<222> LOCATION: (1)..(1)  
<223> OTHER INFORMATION: Xaa is a coupling residue, preferably C, D, E, and K, most preferably C  
<220> FEATURE:  
<221> NAME/KEY: MISC_FEATURE  
<222> LOCATION: (2)..(2)  
<223> OTHER INFORMATION: Xaa is any amino acid, is preferably selected from the group consisting of D, E, G, K, N, or S, more preferably S or N

<400> SEQUENCE: 73

Xaa Xaa Arg Ser Tyr Asn  
1               5

<210> SEQ ID NO 74  
<211> LENGTH: 20  
<212> TYPE: PRT  
<213> ORGANISM: Artificial Sequence  
<220> FEATURE:  
<223> OTHER INFORMATION: STICKER N-terminal fragment of fibre comprising acoupling residue  
<220> FEATURE:  
<221> NAME/KEY: MISC_FEATURE  
<222> LOCATION: (9)..(9)  
<223> OTHER INFORMATION: Xaa is a coupling residue selected from the group comprising K, C, D or E, preferably C  
<220> FEATURE:  
<221> NAME/KEY: MISC_FEATURE  
<222> LOCATION: (16)..(16)  
<223> OTHER INFORMATION: Xaa is selected from the group consisting of E, D and G, is preferably E or D, and is more preferably E  
<220> FEATURE:  
<221> NAME/KEY: misc_feature  
<222> LOCATION: (17)..(17)  
<223> OTHER INFORMATION: Xaa can be any naturally occurring amino acid

<400> SEQUENCE: 74

Ala Lys Arg Ala Arg Leu Ser Thr Xaa Phe Asn Pro Val Tyr Pro Tyr  
1               5                   10                  15

Xaa Asp Glu Ser  
            20

<210> SEQ ID NO 75  
<211> LENGTH: 20  
<212> TYPE: PRT  
<213> ORGANISM: Artificial Sequence  
<220> FEATURE:  
<223> OTHER INFORMATION: STICKER N-terminal fragment of fibre comprising acoupling residue

<400> SEQUENCE: 75

Ala Lys Arg Ala Arg Leu Ser Thr Cys Phe Asn Pro Val Tyr Pro Tyr  
1               5                   10                  15

Glu Asp Glu Ser  
            20

```
<210> SEQ ID NO 76
<211> LENGTH: 20
<212> TYPE: PRT
<213> ORGANISM: Artificial Sequence
<220> FEATURE:
<223> OTHER INFORMATION: STICKER N-terminal fragment of fibre comprising
      acoupling residue
<220> FEATURE:
<221> NAME/KEY: MISC_FEATURE
<222> LOCATION: (9)..(9)
<223> OTHER INFORMATION: Xaa is selected from the group consisting of S,
      D and T, preferably S or D, and is more preferably S
<220> FEATURE:
<221> NAME/KEY: MISC_FEATURE
<222> LOCATION: (16)..(16)
<223> OTHER INFORMATION: Xaa is selected from the group consisting of E,
      D and G, is preferably E or D, and is more preferably E
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: Xaa is a coupling residue, preferably C, D, E,
      and K, most preferably C

<400> SEQUENCE: 76

Ala Lys Arg Ala Arg Leu Ser Thr Xaa Phe Asn Pro Val Tyr Pro Tyr
1               5                   10                  15

Xaa Asp Glu Xaa
            20

<210> SEQ ID NO 77
<211> LENGTH: 20
<212> TYPE: PRT
<213> ORGANISM: Artificial Sequence
<220> FEATURE:
<223> OTHER INFORMATION: STICKER N-terminal fragment of fibre comprising
      acoupling residue

<400> SEQUENCE: 77

Ala Lys Arg Ala Arg Leu Ser Thr Ser Phe Asn Pro Val Tyr Pro Tyr
1               5                   10                  15

Glu Asp Glu Cys
            20

<210> SEQ ID NO 78
<211> LENGTH: 32
<212> TYPE: PRT
<213> ORGANISM: Artificial Sequence
<220> FEATURE:
<223> OTHER INFORMATION: Chikunguny epitope construct inserted into
      penton base protomer

<400> SEQUENCE: 78

Gly Ser Gly Gly Glu Asn Leu Tyr Phe Gln Ser Thr Lys Asp Asn Phe
1               5                   10                  15

Asn Val Tyr Lys Ala Thr Arg Pro Tyr Leu Ala His Gly Gly Ser Gly
                20                  25                  30

<210> SEQ ID NO 79
<211> LENGTH: 571
<212> TYPE: PRT
<213> ORGANISM: Adenovirus Subgroup C Ad2

<400> SEQUENCE: 79
```

```
Met Gln Arg Ala Ala Met Tyr Glu Glu Gly Pro Pro Ser Tyr Glu
1               5                   10                  15

Ser Val Val Ser Ala Ala Pro Val Ala Ala Leu Gly Ser Pro Phe
            20                  25                  30

Asp Ala Pro Leu Asp Pro Pro Phe Val Pro Pro Arg Tyr Leu Arg Pro
            35                  40                  45

Thr Gly Gly Arg Asn Ser Ile Arg Tyr Ser Glu Leu Ala Pro Leu Phe
50                      55                  60

Asp Thr Thr Arg Val Tyr Leu Val Asp Asn Lys Ser Thr Asp Val Ala
65                      70                  75                  80

Ser Leu Asn Tyr Gln Asn Asp His Ser Asn Phe Leu Thr Thr Val Ile
                85                  90                  95

Gln Asn Asn Asp Tyr Ser Pro Gly Glu Ala Ser Thr Gln Thr Ile Asn
                100                 105                 110

Leu Asp Asp Arg Ser His Trp Gly Gly Asp Leu Lys Thr Ile Leu His
                115                 120                 125

Thr Asn Met Pro Asn Val Asn Glu Phe Met Phe Thr Asn Lys Phe Lys
        130                 135                 140

Ala Arg Val Met Val Ser Arg Ser Leu Thr Lys Asp Lys Gln Val Glu
145                 150                 155                 160

Leu Lys Tyr Glu Trp Val Glu Phe Thr Leu Pro Glu Gly Asn Tyr Ser
                165                 170                 175

Glu Thr Met Thr Ile Asp Leu Met Asn Asn Ala Ile Val Glu His Tyr
            180                 185                 190

Leu Lys Val Gly Arg Gln Asn Gly Val Leu Glu Ser Asp Ile Gly Val
        195                 200                 205

Lys Phe Asp Thr Arg Asn Phe Arg Leu Gly Phe Asp Pro Val Thr Gly
210                 215                 220

Leu Val Met Pro Gly Val Tyr Thr Asn Glu Ala Phe His Pro Asp Ile
225                 230                 235                 240

Ile Leu Leu Pro Gly Cys Gly Val Asp Phe Thr His Ser Arg Leu Ser
                245                 250                 255

Asn Leu Leu Gly Ile Arg Lys Arg Gln Pro Phe Gln Glu Gly Phe Arg
            260                 265                 270

Ile Thr Tyr Asp Asp Leu Glu Gly Gly Asn Ile Pro Ala Leu Leu Asp
            275                 280                 285

Val Asp Ala Tyr Gln Ala Ser Leu Lys Asp Asp Thr Glu Gln Gly Gly
        290                 295                 300

Asp Gly Ala Gly Gly Asn Asn Ser Gly Ser Gly Ala Glu Glu Asn
305                 310                 315                 320

Ser Asn Ala Ala Ala Ala Met Gln Pro Val Glu Asp Met Asn Asp
                325                 330                 335

His Ala Ile Arg Gly Asp Thr Phe Ala Thr Arg Ala Glu Glu Lys Arg
            340                 345                 350

Ala Glu Ala Glu Ala Ala Glu Ala Ala Pro Ala Ala Gln Pro
            355                 360                 365

Glu Val Glu Lys Pro Gln Lys Lys Pro Val Ile Lys Pro Leu Thr Glu
        370                 375                 380

Asp Ser Lys Lys Arg Ser Tyr Asn Leu Ile Ser Asn Asp Ser Thr Phe
385                 390                 395                 400

Thr Gln Tyr Arg Ser Trp Tyr Leu Ala Tyr Asn Tyr Gly Asp Pro Gln
        405                 410                 415

Thr Gly Ile Arg Ser Trp Thr Leu Leu Cys Thr Pro Asp Val Thr Cys
```

```
              420             425             430
Gly Ser Glu Gln Val Tyr Trp Ser Leu Pro Asp Met Met Gln Asp Pro
            435                 440                 445

Val Thr Phe Arg Ser Thr Ser Gln Ile Ser Asn Phe Pro Val Val Gly
            450                 455                 460

Ala Glu Leu Leu Pro Val His Ser Lys Ser Phe Tyr Asn Asp Gln Ala
465                 470                 475                 480

Val Tyr Ser Gln Leu Ile Arg Gln Phe Thr Ser Leu Thr His Val Phe
                485                 490                 495

Asn Arg Phe Pro Glu Asn Gln Ile Leu Ala Arg Pro Pro Ala Pro Thr
            500                 505                 510

Ile Thr Thr Val Ser Glu Asn Val Pro Ala Leu Thr Asp His Gly Thr
            515                 520                 525

Leu Pro Leu Arg Asn Ser Ile Gly Gly Val Gln Arg Val Thr Ile Thr
            530                 535                 540

Asp Ala Arg Arg Thr Cys Pro Tyr Val Tyr Lys Ala Leu Gly Ile
545                 550                 555                 560

Val Ser Pro Arg Val Leu Ser Ser Arg Thr Phe
                565                 570

<210> SEQ ID NO 80
<211> LENGTH: 544
<212> TYPE: PRT
<213> ORGANISM: Adenovirus subgroup B Ad3

<400> SEQUENCE: 80

Met Arg Arg Arg Ala Val Leu Gly Gly Ala Val Val Tyr Pro Glu Gly
1               5                   10                  15

Pro Pro Pro Ser Tyr Glu Ser Val Met Gln Gln Gln Ala Ala Met Ile
            20                  25                  30

Gln Pro Pro Leu Glu Ala Pro Phe Val Pro Pro Arg Tyr Leu Ala Pro
            35                  40                  45

Thr Glu Gly Arg Asn Ser Ile Arg Tyr Ser Glu Leu Ser Pro Leu Tyr
        50                  55                  60

Asp Thr Thr Lys Leu Tyr Leu Val Asp Asn Lys Ser Ala Asp Ile Ala
65                  70                  75                  80

Ser Leu Asn Tyr Gln Asn Asp His Ser Asn Phe Leu Thr Thr Val Val
                85                  90                  95

Gln Asn Asn Asp Phe Thr Pro Thr Glu Ala Ser Thr Gln Thr Ile Asn
            100                 105                 110

Phe Asp Glu Arg Ser Arg Trp Gly Gly Gln Leu Lys Thr Ile Met His
            115                 120                 125

Thr Asn Met Pro Asn Val Asn Glu Tyr Met Phe Ser Asn Lys Phe Lys
        130                 135                 140

Ala Arg Val Met Val Ser Arg Lys Ala Pro Glu Gly Val Thr Val Asn
145                 150                 155                 160

Asp Thr Tyr Asp His Lys Glu Asp Ile Leu Lys Tyr Glu Trp Phe Glu
                165                 170                 175

Phe Ile Leu Pro Glu Gly Asn Phe Ser Ala Thr Met Thr Ile Asp Leu
            180                 185                 190

Met Asn Asn Ala Ile Ile Asp Asn Tyr Leu Glu Ile Gly Arg Gln Asn
        195                 200                 205

Gly Val Leu Glu Ser Asp Ile Gly Val Lys Phe Asp Thr Arg Asn Phe
    210                 215                 220
```

```
Arg Leu Gly Trp Asp Pro Glu Thr Lys Leu Ile Met Pro Gly Val Tyr
225                 230                 235                 240

Thr Tyr Glu Ala Phe His Pro Asp Ile Val Leu Leu Pro Gly Cys Gly
            245                 250                 255

Val Asp Phe Thr Glu Ser Arg Leu Ser Asn Leu Leu Gly Ile Arg Lys
        260                 265                 270

Arg His Pro Phe Gln Glu Gly Phe Lys Ile Met Tyr Glu Asp Leu Glu
    275                 280                 285

Gly Gly Asn Ile Pro Ala Leu Leu Asp Val Thr Ala Tyr Glu Glu Ser
290                 295                 300

Lys Lys Asp Thr Thr Thr Glu Thr Thr Thr Leu Ala Val Ala Glu Glu
305                 310                 315                 320

Thr Ser Glu Asp Asp Asp Ile Thr Arg Gly Asp Thr Tyr Ile Thr Glu
            325                 330                 335

Lys Gln Lys Arg Glu Ala Ala Ala Glu Val Lys Lys Glu Leu Lys
        340                 345                 350

Ile Gln Pro Leu Glu Lys Asp Ser Lys Ser Arg Ser Tyr Asn Val Leu
    355                 360                 365

Glu Asp Lys Ile Asn Thr Ala Tyr Arg Ser Trp Tyr Leu Ser Tyr Asn
370                 375                 380

Tyr Gly Asn Pro Glu Lys Gly Ile Arg Ser Trp Thr Leu Leu Thr Thr
385                 390                 395                 400

Ser Asp Val Thr Cys Gly Ala Glu Gln Val Tyr Trp Ser Leu Pro Asp
            405                 410                 415

Met Met Gln Asp Pro Val Thr Phe Arg Ser Thr Arg Gln Val Asn Asn
        420                 425                 430

Tyr Pro Val Val Gly Ala Glu Leu Met Pro Val Phe Ser Lys Ser Phe
    435                 440                 445

Tyr Asn Glu Gln Ala Val Tyr Ser Gln Gln Leu Arg Gln Ala Thr Ser
450                 455                 460

Leu Thr His Val Phe Asn Arg Phe Pro Glu Asn Gln Ile Leu Ile Arg
465                 470                 475                 480

Pro Pro Ala Pro Thr Ile Thr Thr Val Ser Glu Asn Val Pro Ala Leu
            485                 490                 495

Thr Asp His Gly Thr Leu Pro Leu Arg Ser Ser Ile Arg Gly Val Gln
        500                 505                 510

Arg Val Thr Val Thr Asp Ala Arg Arg Thr Cys Pro Tyr Val Tyr
    515                 520                 525

Lys Ala Leu Gly Ile Val Ala Pro Arg Val Leu Ser Ser Arg Thr Phe
530                 535                 540

<210> SEQ ID NO 81
<211> LENGTH: 513
<212> TYPE: PRT
<213> ORGANISM: Adenovirus subgroup B Ad7

<400> SEQUENCE: 81

Met Arg Arg Arg Ala Val Leu Gly Gly Ala Val Val Tyr Pro Glu Gly
1               5                   10                  15

Pro Pro Pro Ser Tyr Glu Ser Val Met Gln Gln Gln Ala Ala Met Leu
            20                  25                  30

Gln Pro Pro Leu Glu Ala Pro Phe Val Pro Arg Tyr Leu Ala Pro
        35                  40                  45

Thr Glu Gly Arg Asn Ser Ile Arg Tyr Ser Glu Leu Ser Pro Leu Tyr
50                  55                  60
```

```
Asp Thr Thr Lys Leu Tyr Leu Val Asp Asn Lys Ser Ala Asp Ile Ala
 65                  70                  75                  80

Ser Leu Asn Tyr Gln Asn Asp His Ser Asn Phe Leu Thr Thr Val Val
             85                  90                  95

Gln Asn Asn Asp Phe Thr Pro Thr Glu Ala Ser Thr Gln Thr Ile Asn
            100                 105                 110

Phe Asp Glu Arg Ser Arg Trp Gly Gly Gln Leu Lys Thr Ile Met His
        115                 120                 125

Thr Asn Met Pro Asn Val Asn Glu Tyr Met Phe Ser Asn Lys Phe Lys
    130                 135                 140

Ala Arg Val Met Val Ser Arg Lys Ala Pro Glu Gly Val Ile Val Asn
145                 150                 155                 160

Asp Thr Tyr Asp His Lys Glu Asp Ile Leu Lys Tyr Glu Trp Phe Glu
                165                 170                 175

Phe Thr Leu Pro Glu Gly Asn Phe Ser Ala Thr Met Thr Ile Asp Leu
            180                 185                 190

Met Asn Asn Ala Ile Ile Asp Asn Tyr Leu Glu Ile Gly Arg Gln Asn
        195                 200                 205

Gly Val Leu Glu Ser Asp Ile Gly Val Lys Phe Asp Thr Arg Asn Phe
    210                 215                 220

Arg Leu Gly Trp Asp Pro Glu Thr Lys Leu Ile Met Pro Gly Val Tyr
225                 230                 235                 240

Thr Tyr Glu Ala Phe His Pro Asp Ile Val Leu Leu Pro Gly Cys Gly
                245                 250                 255

Val Asp Phe Thr Glu Ser Arg Leu Ser Asn Leu Leu Gly Ile Arg Lys
            260                 265                 270

Arg His Pro Phe Gln Glu Gly Phe Lys Ile Met Tyr Glu Asp Leu Glu
        275                 280                 285

Gly Gly Asn Ile Pro Ala Leu Leu Asp Val Thr Ala Tyr Glu Glu Ser
    290                 295                 300

Lys Lys Asp Thr Thr Thr Glu Thr Thr Thr Leu Ala Val Ala Glu Glu
305                 310                 315                 320

Thr Ser Glu Asp Asn Asn Ile Thr Arg Gly Asp Thr Tyr Ile Thr Glu
                325                 330                 335

Lys Gln Lys Arg Glu Ala Ala Ala Glu Val Lys Lys Glu Leu Lys
        340                 345                 350

Ile Gln Pro Leu Glu Lys Asp Ser Lys Ser Arg Ser Tyr Asn Val Leu
    355                 360                 365

Glu Asp Lys Ile Asn Thr Ala Tyr Arg Ser Trp Tyr Leu Ser Tyr Asn
    370                 375                 380

Tyr Gly Asn Pro Glu Lys Gly Ile Arg Ser Trp Thr Leu Leu Thr Thr
385                 390                 395                 400

Ser Asp Val Thr Cys Gly Ala Glu Gln Val Tyr Trp Ser Leu Pro Asp
                405                 410                 415

Met Met Gln Asp Pro Val Thr Phe Arg Ser Thr Arg Gln Ala Thr Thr
            420                 425                 430

Thr Gln Trp Trp Val Gln Ser Leu Cys Pro Ser Ser Gln Arg Val Ser
        435                 440                 445

Thr Met Ser Lys Pro Cys Thr Leu Ser Ser Ser Asp Arg Pro Leu Arg
    450                 455                 460

Ser Arg Thr Ser Ser Thr Ala Ser Leu Arg Thr Arg Ser Ser Ser Ala
465                 470                 475                 480
```

Arg Arg Arg Pro Gln Leu Pro Pro Ser Val Lys Thr Phe Leu Leu Ser
            485                 490                 495

Gln Ile Thr Gly Pro Cys Arg Tyr Ala Ala Val Ser Gly Glu Ser Ser
            500                 505                 510

Ala

<210> SEQ ID NO 82
<211> LENGTH: 561
<212> TYPE: PRT
<213> ORGANISM: Adenovirus subgroup B Ad11

<400> SEQUENCE: 82

Met Arg Arg Val Val Leu Gly Gly Ala Val Val Tyr Pro Glu Gly Pro
1               5                   10                  15

Pro Pro Ser Tyr Glu Ser Val Met Gln Gln Gln Ala Thr Ala Val
            20                  25                  30

Met Gln Ser Pro Leu Glu Ala Pro Phe Val Pro Arg Tyr Leu Ala
            35                  40                  45

Pro Thr Glu Gly Arg Asn Ser Ile Arg Tyr Ser Glu Leu Ala Pro Gln
    50                  55                  60

Tyr Asp Thr Thr Arg Leu Tyr Leu Val Asp Asn Lys Ser Ala Asp Ile
65                  70                  75                  80

Ala Ser Leu Asn Tyr Gln Asn Asp His Ser Asn Phe Leu Thr Val
            85                  90                  95

Val Gln Asn Asn Asp Phe Thr Pro Thr Glu Ala Ser Thr Gln Thr Ile
            100                 105                 110

Asn Phe Asp Glu Arg Ser Arg Trp Gly Gly Gln Leu Lys Thr Ile Met
            115                 120                 125

His Thr Asn Met Pro Asn Val Asn Glu Tyr Met Phe Ser Asn Lys Phe
    130                 135                 140

Lys Ala Arg Val Met Val Ser Arg Lys Pro Pro Asp Gly Ala Ala Val
145                 150                 155                 160

Gly Asp Thr Tyr Asp His Lys Gln Asp Ile Leu Lys Tyr Glu Trp Phe
            165                 170                 175

Glu Phe Thr Leu Pro Glu Gly Asn Phe Ser Val Thr Met Thr Ile Asp
            180                 185                 190

Leu Met Asn Asn Ala Ile Ile Asp Asn Tyr Leu Lys Val Gly Arg Gln
            195                 200                 205

Asn Gly Val Leu Glu Ser Asp Ile Gly Val Lys Phe Asp Thr Arg Asn
    210                 215                 220

Phe Lys Leu Gly Trp Asp Pro Glu Thr Lys Leu Ile Met Pro Gly Val
225                 230                 235                 240

Tyr Thr Tyr Glu Ala Phe His Pro Asp Ile Val Leu Leu Pro Gly Cys
            245                 250                 255

Gly Val Asp Phe Thr Glu Ser Arg Leu Ser Asn Leu Leu Gly Ile Arg
            260                 265                 270

Lys Lys Gln Pro Phe Gln Glu Gly Phe Lys Ile Leu Tyr Glu Asp Leu
            275                 280                 285

Glu Gly Gly Asn Ile Pro Ala Leu Leu Asp Val Asp Ala Tyr Glu Asn
    290                 295                 300

Ser Lys Lys Glu Gln Lys Ala Lys Ile Glu Ala Ala Thr Ala Ala Ala
305                 310                 315                 320

Glu Ala Lys Ala Asn Ile Val Ala Ser Asp Ser Thr Arg Val Ala Asn
            325                 330                 335

```
Ala Gly Glu Val Arg Gly Asp Asn Phe Ala Pro Thr Pro Val Pro Thr
            340                 345                 350

Ala Glu Ser Leu Leu Ala Asp Val Ser Glu Gly Thr Asp Val Lys Leu
        355                 360                 365

Thr Ile Gln Pro Val Glu Lys Asp Ser Lys Asn Arg Ser Tyr Asn Val
370                 375                 380

Leu Glu Asp Lys Ile Asn Thr Ala Tyr Arg Ser Trp Tyr Leu Ser Tyr
385                 390                 395                 400

Asn Tyr Gly Asp Pro Glu Lys Gly Val Arg Ser Trp Thr Leu Leu Thr
                405                 410                 415

Thr Ser Asp Val Thr Cys Gly Ala Glu Gln Val Tyr Trp Ser Leu Pro
            420                 425                 430

Asp Met Met Lys Asp Pro Val Thr Phe Arg Ser Thr Arg Gln Val Ser
        435                 440                 445

Asn Tyr Pro Val Val Gly Ala Glu Leu Met Pro Val Phe Ser Lys Ser
450                 455                 460

Phe Tyr Asn Glu Gln Ala Val Tyr Ser Gln Gln Leu Arg Gln Ser Thr
465                 470                 475                 480

Ser Leu Thr His Val Phe Asn Arg Phe Pro Glu Asn Gln Ile Leu Ile
                485                 490                 495

Arg Pro Pro Ala Pro Thr Ile Thr Thr Val Ser Glu Asn Val Pro Ala
            500                 505                 510

Leu Thr Asp His Gly Thr Leu Pro Leu Arg Ser Ser Ile Arg Gly Val
        515                 520                 525

Gln Arg Val Thr Val Thr Asp Ala Arg Arg Thr Cys Pro Tyr Val
530                 535                 540

Tyr Lys Ala Leu Gly Ile Val Ala Pro Arg Val Leu Ser Ser Arg Thr
545                 550                 555                 560

Phe

<210> SEQ ID NO 83
<211> LENGTH: 508
<212> TYPE: PRT
<213> ORGANISM: Adenovirus subgroup F Ad41

<400> SEQUENCE: 83

Met Arg Arg Ala Val Gly Val Pro Pro Val Met Ala Tyr Ala Glu Gly
1               5                   10                  15

Pro Pro Pro Ser Tyr Glu Ser Val Met Gly Ser Ala Asp Ser Pro Ala
            20                  25                  30

Thr Leu Glu Ala Leu Tyr Val Pro Arg Tyr Leu Gly Pro Thr Glu
        35                  40                  45

Gly Arg Asn Ser Ile Arg Tyr Ser Glu Leu Ala Pro Leu Tyr Asp Thr
    50                  55                  60

Thr Arg Val Tyr Leu Val Asp Asn Lys Ser Ala Asp Ile Ala Ser Leu
65                  70                  75                  80

Asn Tyr Gln Asn Asp His Ser Asn Phe Gln Thr Val Val Gln Asn
                85                  90                  95

Asn Asp Phe Thr Pro Ala Glu Ala Gly Thr Gln Thr Ile Asn Phe Asp
            100                 105                 110

Glu Arg Ser Arg Trp Gly Ala Asp Leu Lys Thr Ile Leu Arg Thr Asn
        115                 120                 125

Met Pro Asn Ile Asn Glu Phe Met Ser Thr Asn Lys Phe Lys Ala Arg
    130                 135                 140
```

Leu Met Val Glu Lys Lys Asn Lys Glu Thr Gly Leu Pro Arg Tyr Glu
145                 150                 155                 160

Trp Phe Glu Phe Thr Leu Pro Glu Gly Asn Tyr Ser Glu Thr Met Thr
                165                 170                 175

Ile Asp Leu Met Asn Asn Ala Ile Val Asp Asn Tyr Leu Glu Val Gly
            180                 185                 190

Arg Gln Asn Gly Val Leu Glu Ser Asp Ile Gly Val Lys Phe Asp Thr
        195                 200                 205

Arg Asn Phe Arg Leu Gly Trp Asp Pro Val Thr Lys Leu Val Met Pro
    210                 215                 220

Gly Val Tyr Thr Asn Glu Ala Phe His Pro Asp Ile Val Leu Leu Pro
225                 230                 235                 240

Gly Cys Gly Val Asp Phe Thr Gln Ser Arg Leu Ser Asn Leu Leu Gly
                245                 250                 255

Ile Arg Lys Arg Leu Pro Phe Gln Glu Gly Phe Gln Ile Met Tyr Glu
            260                 265                 270

Asp Leu Glu Gly Gly Asn Ile Pro Ala Leu Leu Asp Val Ala Lys Tyr
        275                 280                 285

Glu Ala Ser Ile Gln Lys Ala Lys Glu Glu Gly Lys Glu Ile Gly Asp
    290                 295                 300

Asp Thr Phe Ala Thr Arg Pro Gln Asp Leu Val Ile Glu Pro Val Ala
305                 310                 315                 320

Lys Asp Ser Lys Asn Arg Ser Tyr Asn Leu Leu Pro Asn Asp Gln Asn
                325                 330                 335

Asn Thr Ala Tyr Arg Ser Trp Phe Leu Ala Tyr Asn Tyr Gly Asp Pro
            340                 345                 350

Lys Lys Gly Val Gln Ser Trp Thr Leu Leu Thr Thr Ala Asp Val Thr
        355                 360                 365

Cys Gly Ser Gln Gln Val Tyr Trp Ser Leu Pro Asp Met Met Gln Asp
    370                 375                 380

Pro Val Thr Phe Arg Pro Ser Thr Gln Val Ser Asn Tyr Pro Val Val
385                 390                 395                 400

Gly Val Glu Leu Leu Pro Val His Ala Lys Ser Phe Tyr Asn Glu Gln
                405                 410                 415

Ala Val Tyr Ser Gln Leu Ile Arg Gln Ser Thr Ala Leu Thr His Val
            420                 425                 430

Phe Asn Arg Phe Pro Glu Asn Gln Ile Leu Val Arg Pro Pro Ala Pro
        435                 440                 445

Thr Ile Thr Thr Val Ser Glu Asn Val Pro Ala Leu Thr Asp His Gly
450                 455                 460

Thr Leu Pro Leu Arg Ser Ser Ile Ser Gly Val Gln Arg Val Thr Ile
465                 470                 475                 480

Thr Asp Ala Arg Arg Arg Thr Cys Pro Tyr Val His Lys Ala Leu Gly
                485                 490                 495

Ile Val Ala Pro Lys Val Leu Ser Ser Arg Thr Phe
            500                 505

<210> SEQ ID NO 84
<211> LENGTH: 497
<212> TYPE: PRT
<213> ORGANISM: Adenovirus subgroup A Ad12

<400> SEQUENCE: 84

Met Arg Arg Ala Val Glu Leu Gln Thr Val Ala Phe Pro Glu Thr Pro
1                   5                   10                  15

-continued

```
Pro Pro Ser Tyr Glu Thr Val Met Ala Ala Pro Pro Tyr Val Pro
         20                  25                  30

Pro Arg Tyr Leu Gly Pro Thr Glu Gly Arg Asn Ser Ile Arg Tyr Ser
         35                  40                  45

Glu Leu Ser Pro Leu Tyr Asp Thr Thr Arg Val Tyr Leu Val Asp Asn
 50                  55                  60

Lys Ser Ser Asp Ile Ala Ser Leu Asn Tyr Gln Asn Asp His Ser Asn
 65                  70                  75                  80

Phe Leu Thr Thr Val Val Gln Asn Asn Asp Tyr Ser Pro Ile Glu Ala
                 85                  90                  95

Gly Thr Gln Thr Ile Asn Phe Asp Glu Arg Ser Arg Trp Gly Gly Asp
             100                 105                 110

Leu Lys Thr Ile Leu His Thr Asn Met Pro Asn Val Asn Asp Phe Met
             115                 120                 125

Phe Thr Thr Lys Phe Lys Ala Arg Val Met Val Ala Arg Lys Thr Asn
 130                 135                 140

Asn Glu Gly Gln Thr Ile Leu Glu Tyr Glu Trp Ala Glu Phe Val Leu
145                 150                 155                 160

Pro Glu Gly Asn Tyr Ser Glu Thr Met Thr Ile Asp Leu Met Asn Asn
                 165                 170                 175

Ala Ile Ile Glu His Tyr Leu Arg Val Gly Arg Gln His Gly Val Leu
             180                 185                 190

Glu Ser Asp Ile Gly Val Lys Phe Asp Thr Arg Asn Phe Arg Leu Gly
             195                 200                 205

Trp Asp Pro Glu Thr Gln Leu Val Thr Pro Gly Val Tyr Thr Asn Glu
 210                 215                 220

Ala Phe His Pro Asp Ile Val Leu Leu Pro Gly Cys Gly Val Asp Phe
225                 230                 235                 240

Thr Glu Ser Arg Leu Ser Asn Ile Leu Gly Ile Arg Lys Arg Gln Pro
                 245                 250                 255

Phe Gln Glu Gly Phe Val Ile Met Tyr Glu His Leu Glu Gly Gly Asn
             260                 265                 270

Ile Pro Ala Leu Leu Asp Val Lys Lys Tyr Glu Asn Ser Leu Gln Asp
             275                 280                 285

Gln Asn Thr Val Arg Gly Asp Asn Phe Ile Ala Leu Asn Lys Ala Ala
 290                 295                 300

Arg Ile Glu Pro Val Glu Thr Asp Pro Lys Gly Arg Ser Tyr Asn Leu
305                 310                 315                 320

Leu Pro Asp Lys Lys Asn Thr Lys Tyr Arg Ser Trp Tyr Leu Ala Tyr
                 325                 330                 335

Asn Tyr Gly Asp Pro Glu Lys Gly Val Arg Ser Trp Thr Leu Leu Thr
             340                 345                 350

Thr Pro Asp Val Thr Gly Gly Ser Glu Gln Val Tyr Trp Ser Leu Pro
             355                 360                 365

Asp Met Met Gln Asp Pro Val Thr Phe Arg Ser Ser Arg Gln Val Ser
             370                 375                 380

Asn Tyr Pro Val Val Ala Ala Glu Leu Leu Pro Val His Ala Lys Ser
385                 390                 395                 400

Phe Tyr Asn Glu Gln Ala Val Tyr Ser Gln Leu Ile Arg Gln Ser Thr
                 405                 410                 415

Ala Leu Thr Arg Val Phe Asn Arg Phe Pro Glu Asn Gln Ile Leu Val
             420                 425                 430
```

```
Arg Pro Pro Ala Ala Thr Ile Thr Val Ser Glu Asn Val Pro Ala
        435                 440                 445

Leu Thr Asp His Gly Thr Leu Pro Leu Arg Ser Ile Ser Gly Val
    450                 455                 460

Gln Arg Val Thr Ile Thr Asp Ala Arg Arg Thr Cys Pro Tyr Val
465                 470                 475                 480

Tyr Lys Ala Leu Gly Ile Val Ser Pro Arg Val Leu Ser Ser Arg Thr
                485                 490                 495

Phe

<210> SEQ ID NO 85
<211> LENGTH: 517
<212> TYPE: PRT
<213> ORGANISM: Adenovirus subgroup D Ad17

<400> SEQUENCE: 85

Met Arg Arg Ala Val Ser Ser Pro Pro Ser Tyr Glu Ser
1               5                   10              15

Val Met Ala Gln Ala Thr Leu Glu Val Pro Phe Val Pro Pro Arg Tyr
                20                  25                  30

Met Ala Pro Thr Glu Gly Arg Asn Ser Ile Arg Tyr Ser Glu Leu Ala
            35                  40                  45

Pro Leu Tyr Asp Thr Thr Arg Val Tyr Leu Val Asp Asn Lys Ser Ala
50                  55                  60

Asp Ile Ala Ser Leu Asn Tyr Gln Asn Asp His Ser Asn Phe Leu Thr
65                  70                  75                  80

Thr Val Val Gln Asn Asn Asp Phe Thr Pro Ala Glu Ala Ser Thr Gln
                85                  90                  95

Thr Ile Asn Phe Asp Glu Arg Ser Arg Trp Gly Gly Asp Leu Lys Thr
            100                 105                 110

Ile Leu His Thr Asn Met Pro Asn Val Asn Glu Tyr Met Phe Thr Ser
        115                 120                 125

Lys Phe Lys Ala Arg Val Met Val Ala Arg Lys His Pro Gln Gly Val
130                 135                 140

Glu Ala Thr Asp Leu Ser Lys Asp Ile Leu Glu Tyr Glu Trp Phe Glu
145                 150                 155                 160

Phe Thr Leu Pro Glu Gly Asn Phe Ser Glu Thr Met Thr Ile Asp Leu
                165                 170                 175

Met Asn Asn Ala Ile Leu Glu Asn Tyr Leu Gln Val Gly Arg Gln Asn
            180                 185                 190

Gly Val Leu Glu Ser Asp Ile Gly Val Lys Phe Asp Ser Arg Asn Phe
        195                 200                 205

Lys Leu Gly Trp Asp Pro Val Thr Lys Leu Val Met Pro Gly Val Tyr
210                 215                 220

Thr Tyr Glu Ala Phe His Pro Asp Val Val Leu Leu Pro Gly Cys Gly
225                 230                 235                 240

Val Asp Phe Thr Glu Ser Arg Leu Ser Asn Leu Leu Gly Ile Arg Lys
                245                 250                 255

Lys Gln Pro Phe Gln Glu Gly Phe Arg Ile Met Tyr Glu Asp Leu Glu
            260                 265                 270

Gly Gly Asn Ile Pro Ala Leu Leu Asp Val Pro Lys Tyr Leu Glu Ser
        275                 280                 285

Lys Lys Lys Leu Glu Glu Ala Leu Glu Asn Ala Ala Lys Ala Asn Gly
    290                 295                 300
```

```
Pro Ala Arg Gly Asp Ser Ser Val Ser Arg Glu Val Glu Lys Ala Ala
305                 310                 315                 320

Glu Lys Glu Leu Val Ile Glu Pro Ile Lys Gln Asp Asp Ser Lys Arg
            325                 330                 335

Ser Tyr Asn Leu Ile Glu Gly Thr Met Asp Thr Leu Tyr Arg Ser Trp
            340                 345                 350

Tyr Leu Ser Tyr Thr Tyr Gly Asp Pro Glu Lys Gly Val Gln Ser Trp
            355                 360                 365

Thr Leu Leu Thr Thr Pro Asp Val Thr Cys Gly Ala Glu Gln Val Tyr
370                 375                 380

Trp Ser Leu Pro Asp Leu Met Gln Asp Pro Val Thr Phe Arg Ser Thr
385                 390                 395                 400

Gln Gln Val Ser Asn Tyr Pro Val Val Gly Ala Glu Leu Met Pro Phe
            405                 410                 415

Arg Ala Lys Ser Phe Tyr Asn Asp Leu Ala Val Tyr Ser Gln Leu Ile
            420                 425                 430

Arg Ser Tyr Thr Ser Leu Thr His Val Phe Asn Arg Phe Pro Asp Asn
            435                 440                 445

Gln Ile Leu Cys Arg Pro Pro Ala Pro Thr Ile Thr Thr Val Ser Glu
450                 455                 460

Asn Val Pro Ala Leu Thr Asp His Gly Thr Leu Pro Leu Arg Ser Ser
465                 470                 475                 480

Ile Arg Gly Val Gln Arg Val Thr Val Thr Asp Ala Arg Arg Arg Thr
            485                 490                 495

Cys Pro Tyr Val Tyr Lys Ala Leu Gly Ile Val Ala Pro Arg Val Leu
            500                 505                 510

Ser Ser Arg Thr Phe
            515

<210> SEQ ID NO 86
<211> LENGTH: 520
<212> TYPE: PRT
<213> ORGANISM: Adenovirus subgroup E Ad25

<400> SEQUENCE: 86

Met Arg Arg Ala Val Val Ser Ser Ser Pro Pro Ser Tyr Glu Ser
1               5                   10                  15

Val Met Ala Gln Ala Thr Leu Glu Val Pro Phe Val Pro Arg Tyr
            20                  25                  30

Met Ala Pro Thr Glu Gly Arg Asn Ser Ile Arg Tyr Ser Glu Leu Ala
            35                  40                  45

Pro Gln Tyr Asp Thr Thr Arg Val Tyr Leu Val Asp Asn Lys Ser Ala
50                  55                  60

Asp Ile Ala Ser Leu Asn Tyr Gln Asn Asp His Ser Asn Phe Leu Thr
65                  70                  75                  80

Thr Val Val Gln Asn Asn Asp Phe Thr Pro Ala Glu Ala Ser Thr Gln
            85                  90                  95

Thr Ile Asn Phe Asp Glu Arg Ser Arg Trp Gly Gly Asp Leu Lys Thr
            100                 105                 110

Ile Leu His Thr Asn Met Pro Asn Val Asn Glu Tyr Met Phe Thr Ser
            115                 120                 125

Lys Phe Lys Ala Arg Val Met Val Ala Arg Lys His Pro Glu Asn Val
            130                 135                 140

Asp Lys Thr Asp Leu Ser Gln Asp Lys Leu Glu Tyr Glu Trp Phe Glu
145                 150                 155                 160
```

Phe Thr Leu Pro Glu Gly Asn Phe Ser Glu Thr Met Thr Ile Asp Leu
                165                 170                 175

Met Asn Asn Ala Ile Leu Glu Asn Tyr Leu Gln Val Gly Arg Gln Asn
            180                 185                 190

Gly Val Leu Glu Ser Asp Ile Gly Val Lys Phe Asp Ser Arg Asn Phe
        195                 200                 205

Lys Leu Gly Trp Asp Pro Val Thr Lys Leu Val Met Pro Gly Val Tyr
    210                 215                 220

Thr Tyr Glu Ala Phe His Pro Asp Val Val Leu Leu Pro Gly Cys Gly
225                 230                 235                 240

Val Asp Phe Thr Glu Ser Arg Leu Ser Asn Leu Leu Gly Ile Arg Lys
                245                 250                 255

Lys Gln Pro Phe Gln Glu Gly Phe Arg Ile Met Tyr Glu Asp Leu Glu
            260                 265                 270

Gly Gly Asn Ile Pro Ala Leu Leu Asp Thr Lys Lys Tyr Leu Asp Ser
        275                 280                 285

Lys Lys Glu Leu Glu Asp Ala Ala Lys Glu Ala Ala Lys Gln Gln Gly
    290                 295                 300

Asp Gly Ala Val Thr Arg Gly Asp Thr His Leu Thr Val Ala Gln Glu
305                 310                 315                 320

Lys Ala Ala Glu Lys Glu Leu Val Ile Val Pro Ile Glu Lys Asp Glu
                325                 330                 335

Ser Asn Arg Ser Tyr Asn Leu Ile Lys Asp Thr His Asp Thr Met Tyr
            340                 345                 350

Arg Ser Trp Tyr Leu Ser Tyr Thr Tyr Gly Asp Pro Glu Lys Gly Val
        355                 360                 365

Gln Ser Trp Thr Leu Leu Thr Thr Pro Asp Val Thr Cys Gly Ala Glu
    370                 375                 380

Gln Val Tyr Trp Ser Leu Pro Asp Leu Met Gln Asp Pro Val Thr Phe
385                 390                 395                 400

Arg Ser Thr Gln Gln Val Ser Asn Tyr Pro Val Val Gly Ala Glu Leu
                405                 410                 415

Met Pro Phe Arg Ala Lys Ser Phe Tyr Asn Asp Leu Ala Val Tyr Ser
            420                 425                 430

Gln Leu Ile Arg Ser Tyr Thr Ser Leu Thr His Val Phe Asn Arg Phe
        435                 440                 445

Pro Asp Asn Gln Ile Leu Cys Arg Pro Pro Ala Pro Thr Ile Thr Thr
    450                 455                 460

Val Ser Glu Asn Val Pro Ala Leu Thr Asp His Gly Thr Leu Pro Leu
465                 470                 475                 480

Arg Ser Ser Ile Arg Gly Val Gln Arg Val Thr Val Thr Asp Ala Arg
                485                 490                 495

Arg Arg Thr Cys Pro Tyr Val Tyr Lys Ala Leu Gly Ile Val Ala Pro
            500                 505                 510

Arg Val Leu Ser Ser Arg Thr Phe
        515                 520

<210> SEQ ID NO 87
<211> LENGTH: 519
<212> TYPE: PRT
<213> ORGANISM: Adenovirus   subgroup D Ad37

<400> SEQUENCE: 87

Met Arg Arg Ala Val Val Ser Ser Ser Pro Pro Pro Ser Tyr Glu Ser

-continued

```
1               5                   10                  15
Val Met Ala Gln Ala Thr Leu Glu Val Pro Phe Val Pro Arg Tyr
            20                  25                  30
Met Ala Pro Thr Glu Gly Arg Asn Ser Ile Arg Tyr Ser Glu Leu Ala
            35                  40                  45
Pro Leu Tyr Asp Thr Thr Arg Val Tyr Leu Val Asp Asn Lys Ser Ala
    50                  55                  60
Asp Ile Ala Ser Leu Asn Tyr Gln Asn Asp His Ser Asn Phe Leu Thr
65                  70                  75                  80
Thr Val Val Gln Asn Asn Asp Phe Thr Pro Ala Glu Ala Ser Thr Gln
                85                  90                  95
Thr Ile Asn Phe Asp Glu Arg Ser Arg Trp Gly Gly Asp Leu Lys Thr
            100                 105                 110
Ile Leu His Thr Asn Met Pro Asn Val Asn Glu Tyr Met Phe Thr Ser
            115                 120                 125
Lys Phe Lys Ala Arg Val Met Val Ala Arg Lys Lys Ala Glu Gly Ala
        130                 135                 140
Asp Ala Asn Asp Arg Ser Lys Asp Ile Leu Glu Tyr Gln Trp Phe Glu
145                 150                 155                 160
Phe Thr Leu Pro Glu Gly Asn Phe Ser Glu Thr Met Thr Ile Asp Leu
                165                 170                 175
Met Asn Asn Ala Ile Leu Glu Asn Tyr Leu Gln Val Gly Arg Gln Asn
            180                 185                 190
Gly Val Leu Glu Ser Asp Ile Gly Val Lys Phe Asp Ser Arg Asn Phe
        195                 200                 205
Lys Leu Gly Trp Asp Pro Val Thr Lys Leu Val Met Pro Gly Val Tyr
    210                 215                 220
Thr Tyr Glu Ala Phe His Pro Asp Val Val Leu Leu Pro Gly Cys Gly
225                 230                 235                 240
Val Asp Phe Thr Glu Ser Arg Leu Ser Asn Leu Leu Gly Ile Arg Lys
                245                 250                 255
Lys Gln Pro Phe Gln Glu Gly Phe Arg Ile Met Tyr Glu Asp Leu Val
            260                 265                 270
Gly Gly Asn Ile Pro Ala Leu Leu Asn Val Lys Glu Tyr Leu Lys Asp
        275                 280                 285
Lys Glu Glu Ala Gly Lys Ala Asp Ala Asn Thr Ile Lys Ala Gln Asn
    290                 295                 300
Asp Ala Val Pro Arg Gly Asp Asn Tyr Ala Ser Ala Ala Glu Ala Lys
305                 310                 315                 320
Ala Ala Gly Lys Glu Ile Glu Leu Lys Ala Ile Leu Lys Asp Asp Ser
                325                 330                 335
Asp Arg Ser Tyr Asn Val Ile Glu Gly Thr Thr Asp Thr Leu Tyr Arg
            340                 345                 350
Ser Trp Tyr Leu Ser Tyr Thr Tyr Gly Asp Pro Glu Lys Gly Val Gln
        355                 360                 365
Ser Trp Thr Leu Leu Thr Thr Pro Asp Val Thr Cys Gly Ala Glu Gln
    370                 375                 380
Val Tyr Trp Ser Leu Pro Asp Leu Met Gln Asp Pro Val Thr Phe Arg
385                 390                 395                 400
Ser Thr Gln Gln Val Ser Asn Tyr Pro Val Val Gly Ala Glu Leu Met
                405                 410                 415
Pro Phe Arg Ala Lys Ser Phe Tyr Asn Asp Leu Ala Val Tyr Ser Gln
            420                 425                 430
```

```
Leu Ile Arg Ser Tyr Thr Ser Leu Thr His Val Phe Asn Arg Phe Pro
        435             440             445

Asp Asn Gln Ile Leu Cys Arg Pro Pro Ala Pro Thr Ile Thr Thr Val
    450             455             460

Ser Glu Asn Val Pro Ala Leu Thr Asp His Gly Thr Leu Pro Leu Arg
465             470             475             480

Ser Ser Ile Arg Gly Val Gln Arg Val Thr Val Thr Asp Ala Arg Arg
            485             490             495

Arg Thr Cys Pro Tyr Val Tyr Lys Ala Leu Gly Ile Val Ala Pro Arg
            500             505             510

Val Leu Ser Ser Arg Thr Phe
        515
```

We claim:

1. A virus-like particle (VLP) comprising 12 pentamers each comprising five adenovirus penton base protomers and at least one engineered polypeptide comprising at least one adenovirus fibre protein N-terminal fragment specifically binding to an adenovirus fibre protein binding cleft of a penton base protomer and:
   (i) a non-adenoviral peptide, optionally linked to the fibre protein fragment via peptide linker, and/or
   (ii) a drug or label that is covalently or non-covalently coupled to said adenovirus fibre protein N-terminal fragment.

2. The VLP of claim 1, wherein the fibre protein fragment comprises:
   $X_{58}$-F-N-P-V-Y-P-Y-$X_{59}$ (SEQ ID NO: 43) wherein
   $X_{58}$ is selected from the group consisting of S, D and T; and
   $X_{59}$ is selected from the group consisting of E, D and G.

3. The VLP of claim 1, wherein the non-adenoviral polypeptide is selected from the group consisting of immunogenic peptides, pathogen neutralizing peptides, non-adenovirus viral peptides, bacterial peptides, immune-modulating peptides, and cancer peptides.

4. The VLP of claim 3, wherein the non-adenovirus viral peptide is selected from the group consisting of SEQ ID NOs: 55 to 60.

5. The VLP of claim 1, wherein the engineered polypeptide comprises a protease cleavage site.

6. The VLP of claim 5, wherein the protease cleavage site is a sequence specific endopeptidase site.

7. The VLP of claim 6, wherein the sequence specific endopeptidase site is a tobacco etch virus Nia protease (TEV) cleavage site.

8. The VLP of claim 1, wherein the drug is selected from the group consisting of a chemotherapeutic drug, an antipathogenic drug, an immune modulating drug and an anti-inflammatory drug.

9. The VLP of claim 1, wherein the engineered polypeptide comprises 2, 3, 4, 5, 6, 7 or 8 repeats of the adenovirus fibre protein N-terminal fragment.

10. The VLP of claim 1, wherein the engineered polypeptide comprises 2 or 3 consecutive repeats of the adenovirus fibre protein N-terminal fragment.

11. The VLP of claim 10, wherein the adenovirus fibre protein N-terminal fragment repeats are arranged in a head-to-tail orientation.

12. The VLP of claim 1, wherein the adenovirus fibre protein N-terminal fragment has a length of 50 contiguous amino acids or less of N-terminal fibre sequence.

13. The VLP of claim 12, wherein the adenovirus fibre protein N-terminal fragment has a length of 20 contiguous amino acids or less of N-terminal fibre sequence.

14. The VLP of claim 1, wherein the adenovirus fibre protein N-terminal fragment is located N-terminally to the non-adenoviral polypeptide.

15. The VLP of claim 1, wherein the engineered polypeptide comprises a peptide linker between the non-adenoviral polypeptide and the adenovirus fibre protein N-terminal fragment.

16. The VLP of claim 1, wherein the engineered polypeptide comprises a coupling residue.

17. The VLP of claim 16, wherein the coupling residue is inserted and/or positioned at the N- and/or C-terminus of the adenovirus fibre protein N-terminal fragment.

18. The VLP of claim 17, wherein the adenovirus fibre protein N-terminal fragment has the following sequence:
    $X_{58}$-F-N-P-V-Y-P-Y-$X_{59}$-$(X_{63})$n-Xc (SEQ ID NO: 69) wherein
    $X_{58}$ is selected from the group consisting of S, D and T; and
    $X_{59}$ is selected from the group consisting of E, D and G;
    $X_{63}$ is in each case independently any amino acid;
    Xc is a coupling residue; and
    n is an integer between 0 to 10.

19. The VLP of claim 17, wherein the adenovirus fibre protein N-terminal fragment has the following sequence:
    A-K-R-A-R-L-S-T-$X_{58}$-F-N-P-V-Y-P-Y-$X_{59}$-D-E-$X_c$ (SEQ ID NO: 76) wherein
    $X_{58}$ is selected from the group consisting of S, D and T;
    $X_{59}$ is selected from the group consisting of E, D and G; and
    $X_c$ is a coupling residue.

20. The VLP of claim 17, wherein the fibre protein N-terminal fragment has the sequence of SEQ ID NO: 77.

21. The VLP of claim 16, wherein the coupling residue is selected from the group consisting of Lys, Cys, Asp and Glu.

22. The VLP of claim 1, comprising 2 to 60 of the engineered polypeptides each binding to an adenovirus fibre binding cleft of an adenovirus penton base protomer.

23. The VLP of claim 1, wherein each adenovirus penton base protomer is an engineered polypeptide comprising a first RGD-loop, a second RGD-loop, a variable loop (V loop), an adenovirus fibre protein binding cleft and/or a N-terminal domain, and comprises one or more non-adenoviral peptide in the first, the second or both the first and the second RGD-loops and/or in the V loop, wherein each engineered adenovirus penton base promoter is capable of assembling into VLPs.

24. The VLP of claim 23, wherein the engineered adenovirus penton base protomer comprises
at least one target specific binding domain in the first, the second or both the first and the second RGD-loops, and/or in the V loop.

25. The VLP of claim 23, wherein the engineered adenovirus penton base protomer comprises a non-adenoviral peptide at the N- and/or C-terminus of the penton base protomer.

26. The VLP of claim 23, wherein the engineered adenovirus penton base protomer comprises at least one heterologous coupling residue in the first, the second, or both the first and the second RGD-loops, in the V loop and/or in the N-terminal domain of the penton base protomer, wherein the N-terminus of the N-terminal domain of the penton base protomer is defined as follows:

$X_1$-G-R-N-S-I-R, (SEQ ID NO: 44)

and the C-terminus of the N-terminal domain of the penton base protomer is defined as follows:

D-$X_2$-R-S-R-G, (SEQ ID NO: 45)

wherein
$X_1$ is selected from the group consisting of G and E, and
$X_2$ is selected from the group consisting of D and E.

27. The VLP of claim 23, wherein the engineered adenovirus penton base protomer comprises a drug, label or polypeptide covalently or non-covalently coupled to one or more amino acids of the first, the second or both the first and the second RGD-loops and/or one or more amino acids of the V loop of the penton base protomer.

28. The VLP of claim 23, wherein the engineered adenovirus penton base protomer comprises at least one heterologous coupling residue in the adenovirus fibre protein binding cleft of the penton base protomer.

29. A method for producing the VLP of claim 1 comprising a step of admixing the engineered polypeptides with the adenovirus penton base protomers.

30. A method for producing the VLP of claim 1, wherein said VLPs comprise disease and/or patient specific non-adeno viral peptides, the method comprising the steps of: (a) determining the amino acid sequence of disease or patient specific non-adenoviral peptides; (b) synthesizing the engineered polypeptide comprising an adenovirus fibre protein N-terminal fragment specifically binding to an adenovirus fibre protein binding cleft of a penton base protomer and at least one of said non-adenoviral peptides; and (c) admixing said engineered polypeptide with the adenovirus penton base protomers".

31. A pharmaceutical composition comprising the VLP of claim 1.

32. The VLP of claim 2, wherein $X_{58}$ is S.
33. The VLP of claim 2, wherein $X_{58}$ is T.
34. The VLP of claim 2, wherein $X_{59}$ E.
35. The VLP of claim 2, wherein $X_{59}$ is D.
36. The VLP of claim 19, wherein $X_{58}$ is S.
37. The VLP of claim 19, wherein $X_{58}$ is T.
38. The VLP of claim 19, wherein $X_{59}$ E.
39. The VLP of claim 19, wherein $X_{59}$ is D.

* * * * *

UNITED STATES PATENT AND TRADEMARK OFFICE
CERTIFICATE OF CORRECTION

PATENT NO. : 12,122,806 B2
APPLICATION NO. : 17/590444
DATED : October 22, 2024
INVENTOR(S) : Imre Berger et al.

Page 1 of 1

It is certified that error appears in the above-identified patent and that said Letters Patent is hereby corrected as shown below:

In the Claims

In Claim 30, Column 174, Line 24, remove """".

In Claim 34, Column 174, Line 29, insert --is-- before "E".

In Claim 38, Column 174, Line 33, insert --is-- before "E".

Signed and Sealed this
Twenty-fourth Day of December, 2024

Derrick Brent
*Acting Director of the United States Patent and Trademark Office*